US007943580B2

(12) United States Patent
Kangawa et al.

(10) Patent No.: US 7,943,580 B2
(45) Date of Patent: May 17, 2011

(54) POLYPEPTIDE AND THE USE THEREOF

(75) Inventors: Kenji Kangawa, Minoo (JP); Kenji Mori, Minoo (JP); Mikiya Miyazato, Kyotanabe (JP); Masayasu Kojima, Kurume (JP)

(73) Assignees: National Cerebral and Cardiovascular Center, Suita (JP); Takeda Pharmaceutical Company Limited, Osaka (JP)

( * ) Notice: Subject to any disclaimer, the term of this patent is extended or adjusted under 35 U.S.C. 154(b) by 785 days.

(21) Appl. No.: 11/793,760

(22) PCT Filed: Dec. 22, 2005

(86) PCT No.: PCT/JP2005/024188
§ 371 (c)(1),
(2), (4) Date: Jun. 21, 2007

(87) PCT Pub. No.: WO2006/068326
PCT Pub. Date: Jun. 29, 2006

(65) Prior Publication Data
US 2008/0124335 A1 May 29, 2008

(30) Foreign Application Priority Data
Dec. 24, 2004 (JP) .................. 2004-374029

(51) Int. Cl.
*A61K 38/16* (2006.01)
*A61K 51/08* (2006.01)
(52) U.S. Cl. .................. 514/21.3; 530/325; 424/1.69
(58) Field of Classification Search .................. None
See application file for complete search history.

(56) References Cited

U.S. PATENT DOCUMENTS
2004/0152136 A1    8/2004  Hinuma et al.
2006/0293232 A1*  12/2006  Levy et al. .................. 514/12

FOREIGN PATENT DOCUMENTS
| EP | 1 237 001 |    | 9/2002 |
| EP | 1 237 001 | A1 * | 9/2002 |
| EP | 1237001 | A1 * | 9/2002 |
| WO | 98/58962 |    | 12/1998 |
| WO | 01/40797 |    | 6/2001 |
| WO | 01/57524 |    | 8/2001 |
| WO | 01/81418 |    | 11/2001 |

OTHER PUBLICATIONS

Mori, 2005, The EMBO Journal, 24, 325-335.*
P. L. Brighton et al., "Neuromedin U and its Receptors: Structure, Function, and Physiological Roles", Pharmacological Reviews, vol. 56, No. 2, pp. 231-248,2004.
N. Minamino et al.,"Novel Uterus Stimulating and Hypertensive Peptides Identified in Porcine Spinal Cord", Biochemical and Biophysical Research Communications, vol. 130, No. 3, pp. 1078-1085, Aug. 15, 1985.
A. D. Howard et al., "Identification of Receptors for Neuromedin U and its Role in Feeding", Nature, vol. 406, pp. 70-74, Jul. 2000.
R. Hanada et al., "Neuromedin U has a Novel Anorexigenic Effect Independent of the Leptin Signaling Pathway", Nature Medicine, vol. 10, No. 10, pp. 1067-1073, Oct. 2004.
C. Austin et al., "Cloning and Characterization of the cDNA Encoding the Human Neuromedin U (NmU) Precursor: NmU Expression in the Human Gastrointestinal Tract", Journal of Molecular Endocrinology, vol. 14, pp. 157-169, 1995.
G. Lo et al., "Characterization of Complementary DNA Encoding the Rat Neuromedin U Precursor", Molecular Endocrinology, vol. 6, No. 10, pp. 1538-1544, 1992.
K. Mori et al., "Identification of Neuromedin S and its Possible Role in the Mammalian Circadian Oscillatory System", The EMBO Journal, vol. 24, No. 2, pp. 325-335, 2005.
T. Ida et al., "Neuromedin S is a Novel Anorexigenic Hormone", Endocrinology, vol. 146, No. 10, pp. 4217-4223, 2005.
Supplementary European Search Report issued Jun. 11, 2008 in connection with EP 05 82 2348 corresponding to the present U.S. application.
Miyazato, M. et al., *Identification and functional analysis of a novel ligand for G protein-coupled receptor, Neuromedin S.*, Regulatory Peptides, vol. 145 (2008), pp. 37-41, XP022396507.
Abiko, T. et al., *Syntheses of two neuromedin U (NMU) analogues and their comparative reducing food intake effects in rats*, Amino Acids, vol. 25 (2003), pp. 107-110, XP002448906.

* cited by examiner

*Primary Examiner* — Andrew D Kosar
*Assistant Examiner* — Satyanarayana R Gudibande
(74) *Attorney, Agent, or Firm* — Wenderoth, Lind & Ponack, L.L.P.

(57) ABSTRACT

The present invention provides a variety of useful polypeptides. In particular, a polypeptide comprising the same or substantially the same amino acid sequence as the amino acid sequence represented by SEQ ID NO: 1, SEQ ID NO: 2 or SEQ ID NO: 3, its amide, or a salt thereof can be used as an agent for preventing/treating hypotension; an agent for preventing/treating obesity, hyperphagia, etc.; an agent for preventing/treating lethargy, time-zone change syndrome (jet lag), etc.; an agent for preventing/treating sterility, etc. A compound or its salt that promotes the activity of a polypeptide comprising the same or substantially the same amino acid sequence as the amino acid sequence represented by any of SEQ ID NOS: 7 to 12 and 37 to 42, its partial peptide, or a salt thereof is useful as an agent for preventing/treating, e.g., menopausal symptoms or hyperthyroidism. A compound or its salt that inhibits the activity of said polypeptide is useful as an agent for preventing/treating, e.g., sterility or hypothyroidism.

8 Claims, No Drawings

POLYPEPTIDE AND THE USE THEREOF

This application is a U.S. national stage of International Application No. PCT/JP2005/024188 filed Dec. 22, 2005.

TECHNICAL FIELD

The present invention relates to a novel polypeptide or its salt, a polynucleotide encoding the same, use thereof, and so on.

BACKGROUND ART

Neuromedin U is a peptide isolated and purified from porcine spinal cords, based on its activity to contract smooth-muscle in rat uterus. Two neuromedins U, namely, neuromedin U-8 composed of 8 amino acid residues and neuromedin U-25 composed of 25 amino acid residues are first reported (Minamino, N. et al., Biochem. Biophys. Res. Commun., 130, 1078-1085, 1985). The sequence of neuromedin U-8 is identical to the C-terminal sequence of neuromedin U-25 and the upstream region contains a basic amino acid pair often observed in the cleavage site for processing, and the two neuromedins U are thus expected to be derived from a common precursor. Also, other physiological functions besides the smooth muscle contraction activity are widely known. Such functions reportedly include, for example, an increase in blood pressure (Minamino. N. et al.), a decrease in splanchnic blood flow (Sumi, S. et al., Life Sci., 41, 1585-1590, 1987), adjustment of ion transportation in intestine (Brown, D. R. and Quito, F. L., Eur. J. Pharmacol. 155, 159-162, 1998) and an increase in ACTH and a subsequent increase in corticosterone after subcutaneous administration of neuromedin U (Malendowicz, L. K. et al., In Vivo, 7, 419-422, 1993). Furthermore, TGR1 (WO 01/57524) and FM-3 (WO 00/02918) are hitherto reported as receptors for neuromedin U.

DISCLOSURE OF THE INVENTION

Currently, some preventive/therapeutic agents for hypotension, obesity, lethargy, time zone change syndrome, menopausal symptoms, hyperthyroidism, sterility, hypothyroidism, etc. However, it is desired to provide more excellent agents for preventing/treating hypotension, obesity, lethargy, time zone change syndrome, menopausal symptoms, hyperthyroidism, sterility, hypothyroidism, etc.

The present inventors made intensive studies to solve the foregoing problems and found, as an endogenous ligand for TGR1 and FM-3, a polypeptide comprising the amino acid sequence represented by SEQ ID NO: 1, SEQ ID NO: 2, SEQ ID NO: 3, SEQ ID NO: 7, SEQ ID NO: 8, SEQ ID NO: 9, SEQ ID NO: 10, SEQ ID NO: 11 or SEQ ID NO: 12 and also found that these polypeptides have specific cell stimulating activities. Based on these findings, further investigations were continued. As a result, the inventors have come to accomplish the present invention.

That is, the present invention provides the following features, and so on.
(1) A polypeptide, which comprises the same or substantially the same amino acid sequence as the amino acid sequence represented by SEQ ID NO: 1, SEQ ID NO: 2 or SEQ ID NO: 3, or its amide, or a salt thereof.
(2) A polypeptide, which consists of the amino acid sequence represented by SEQ ID NO: 1, or its amide, or a salt thereof.
(3) A polypeptide, which consists of the amino acid sequence represented by SEQ ID NO: 2, or its amide, or a salt thereof.
(4) A polypeptide, which consists of the amino acid sequence represented by SEQ ID NO: 3, or its amide, or a salt thereof.
(5) A partial peptide of the polypeptide according to (1) above, its amide, or a salt thereof.
(6) A polynucleotide, which comprises a polynucleotide encoding the polypeptide according to (1) above, or its partial peptide.
(7) The polynucleotide according to (6) above, which is a DNA.
(8) The DNA according to (7) above, which comprises the base sequence represented by SEQ ID NO: 13, SEQ ID NO: 14 or SEQ ID NO: 15.
(9) A recombinant vector, which comprises the polynucleotide according to (6) above.
(10) A transformant, which is transformed with the recombinant vector according to (9) above.
(11) The polypeptide according to (1) above, which is a polypeptide comprising the same or substantially the same amino acid sequence as the amino acid sequence represented by SEQ ID NO: 4, SEQ ID NO: 5 or SEQ ID NO: 6; its amide, or a salt thereof.
(12) A polypeptide, which consists of the amino acid sequence represented by SEQ ID NO: 4, or a salt thereof.
(13) A polypeptide, which consists of the amino acid sequence represented by SEQ ID NO: 5, or a salt thereof.
(14) A polypeptide, which consists of the amino acid sequence represented by SEQ ID NO: 6, or a salt thereof.
(15) A partial peptide of the polypeptide according to (11) above, its amide, or a salt thereof.
(16) A polynucleotide, which comprises a polynucleotide encoding the polypeptide according to (11) above, or its partial peptide.
(17) The polynucleotide according to (16) above, which is a DNA.
(18) The DNA according to (13) above, which comprises the base sequence represented by SEQ ID NO: 16, SEQ ID NO: 17 or SEQ ID NO: 18.
(19) A recombinant vector, which comprises the polynucleotide according to (16) above.
(20) A transformant, which is transformed with the recombinant vector according to (19) above.
(21) A polypeptide, which comprises the same or substantially the same amino acid sequence as the amino acid sequence represented by SEQ ID NO: 7, SEQ ID NO: 8, SEQ ID NO: 9, SEQ ID NO: 10, SEQ ID NO: 11 or SEQ ID NO: 12, or a salt thereof.
(22) A polypeptide, which consists of the amino acid sequence represented by SEQ ID NO: 7, SEQ ID NO: 8, SEQ ID NO: 9, SEQ ID NO: 10, SEQ ID NO: 11 or SEQ ID NO: 12, or a salt thereof
(23) A partial peptide of the polypeptide according to (21) above, or a salt thereof
(24) A polynucleotide, which comprises a polynucleotide encoding the polypeptide according to (21) above.
(25) The polynucleotide according to (24) above, which is a DNA.
(26) The DNA according to (25) above, which comprises the base sequence represented by SEQ ID NO: 19, SEQ ID NO: 20, SEQ ID NO: 21, SEQ ID NO: 22, SEQ ID NO: 23 or SEQ ID NO: 24.
(27) A recombinant vector, which comprises the polynucleotide according to (24) above.
(28) A transformant, which is transformed with the recombinant vector according to (27) above.
(29) A method of screening a compound or its salt that promotes or inhibits the activity of the polypeptide according to (1) above, which comprises using said polypeptide, its partial peptide, its amide, or a salt thereof.
(30) The screening method according to (29) above, which comprises using (i) the polypeptide according to (1) above, its partial peptide or its amide, or a salt thereof, and (ii) a protein comprising the same or substantially the same amino acid sequence as the amino acid sequence represented by SEQ ID NO: 25, SEQ ID NO: 27 or SEQ ID NO: 29, or its partial peptide, or a salt thereof.
(31) The screening method according to (30) above, which comprises using a protein comprising the amino acid sequence represented by SEQ ID NO: 25, its partial peptide, or a salt thereof.
(32) The screening method according to (29) above, which comprises using (i) the polypeptide according to (1) above, its partial peptide or its amide, or a salt thereof, and (ii) a protein comprising the same or substantially the same amino acid sequence as the amino acid sequence represented by SEQ ID NO: 31, SEQ ID NO: 33 or SEQ ID NO: 35, or its partial peptide, or a salt thereof.
(33) The screening method according to (32) above, wherein the protein comprising the amino acid sequence represented by SEQ ID NO: 31, or its partial peptide, or a salt thereof.
(34) A kit for screening a compound or its salt that promotes or inhibits the activity of the polypeptide according to (1) above, which comprises said polypeptide, or its partial peptide or its amide, or a salt thereof.
(35) The screening kit according to (34) above, which further comprises a protein comprising the same or substantially the same amino acid sequence as the amino acid sequence represented by SEQ ID NO: 25, SEQ ID NO: 27 or SEQ ID NO: 29, or its partial peptide, or a salt thereof.
(36) The screening kit according to (34) above, which further comprises a protein comprising the same or substantially the same amino acid sequence as the amino acid sequence represented by SEQ ID NO: 31, SEQ ID NO: 33 or SEQ ID NO: 35, or its partial peptide, or a salt thereof.
(37) A method of screening a compound or its salt that promotes or inhibits the activity of the polypeptide according to (21) above, which comprises using said polypeptide or a salt thereof.
(38) A kit for screening a compound or its salt that promotes or inhibits the activity of the polypeptide according to (21) above, which comprises said polypeptide or a salt thereof.
(39) A medicament comprising the polypeptide according to (1) or (11) above, or its partial peptide or its amide, or a salt thereof
(40) A medicament comprising the polynucleotide according to (6) or (16) above.
(41) A medicament comprising a compound or its salt that promotes the activity of the polypeptide according to (1) or (11) above, or its partial peptide or its amide, or a salt thereof.
(42) The medicament according to (39) through (41) above, which is an agent for preventing/treating hypotension, obesity, lethargy or time zone change syndrome.
(43) The medicament according to (39) through (41) above, which is an agent for preventing/treating sterility.
(44) A method for preventing/treating hypotension, obesity, lethargy, time zone change syndrome or sterility, which comprises promoting the activity of the polypeptide according to (1) or (11) above, or its partial peptide or its amide, or a salt thereof.
(45) A method for preventing/treating hypotension, obesity, lethargy, time zone change syndrome or sterility, which comprises administering to a mammal an effective dose of (i) the polypeptide according to (1) or (11) above, or its partial peptide or its amide, or a salt thereof, (ii) the polynucleotide according to (6) or (16) above, or (iii) a compound or its salt that promotes the activity of the polypeptide, or its partial peptide or its amide, or a salt thereof.
(46) Use of (i) the polypeptide according to (1) or (11) above, or its partial peptide or its amide, or a salt thereof, (ii) the polynucleotide according to (6) or (16) above, or (iii) a compound or its salt that promotes the activity of the polypeptide, or its partial peptide or its amide, or a salt thereof, for the manufacture of an agent for preventing/treating hypotension, obesity, lethargy, time zone change syndrome or sterility.
(47) A medicament comprising the polypeptide according to (21) above, or its partial peptide, or a salt thereof
(48) A medicament comprising the polynucleotide according to (24) above.
(49) A medicament comprising a compound or its salt that promotes the activity of the polypeptide according to (21) above, or its partial peptide, or a salt thereof.
(50) The medicament according to any one of (47) through (49) above, which is an agent for preventing/treating menopausal symptoms or hyperthyroidism.
(51) A method for preventing/treating menopausal symptoms or hyperthyroidism, which comprises promoting the activity of the polypeptide according to (21) above, or its partial peptide, or a salt thereof.
(52) A method for preventing/treating menopausal symptoms or hyperthyroidism, which comprises administering to a mammal an effective dose of (i) the polypeptide according to (21) above, or its partial peptide, or a salt thereof, (ii) the polynucleotide according to (24) above, or (iii) a compound or its salt that promotes the activity of the polypeptide, or its partial peptide, or a salt thereof.
(53) Use of (i) the polypeptide according to (21) above, or its partial peptide, or a salt thereof, (ii) the polynucleotide according to (24) above, or (iii) a compound or its salt that promotes the activity of the polypeptide, or its partial peptide, or a salt thereof, for the manufacture of an agent for preventing/treating menopausal symptoms or hyperthyroidism.
(54) An antibody to the polypeptide according to (1) or (11) above, or its partial peptide or its amide, or a salt thereof
(55) A medicament comprising the antibody according to (54) above.
(56) A diagnostic agent comprising the antibody according to (54) above.
(57) The diagnostic agent according to (56) above, which is a diagnostic agent for hypotension, obesity, lethargy or time zone change syndrome.
(58) The diagnostic agent according to (56) above, which is a diagnostic agent for sterility.
(58a) The diagnostic agent according to (56) above, which is a diagnostic agent for hypertension, anorexia, menopausal symptoms, insomnia or immune/inflammatory disease.
(59) An antisense polynucleotide, which comprises the entire base sequence complementary or substantially complementary to the polynucleotide according to (6) or (16) above, or a part of the base sequence.
(60) A medicament comprising the antisense polynucleotide according to (59) above.
(61) A medicament comprising a compound or its salt that inhibits the activity of the polypeptide according to (1) or (11) above, or its partial peptide or its amide, or a salt thereof.
(62) The medicament according to (55), (61) or (61) above, which is an agent for preventing/treating hypertension, anorexia or insomnia.
(63) The medicament according to (55), (60) or (61) above, which is an agent for preventing/treating menopausal symptoms.

(64) A method for preventing/treating hypertension, anorexia, menopausal symptoms or insomnia, which comprises inhibiting the activity of the polypeptide according to (1) or (11) above, or its partial peptide or its amide, or a salt thereof.
(65) A method for preventing/treating hypertension, anorexia, menopausal symptoms or insomnia, which comprises administering to a mammal an effective dose of (i) an antibody of the polypeptide according to (1) or (11) above, or its partial peptide or its amide, or a salt thereof, (ii) the antisense polynucleotide comprising the entire base sequence complementary or substantially complementary to the polynucleotide according to (6) or (16) above, or a part of the base sequence, or (iii) a compound or its salt that inhibits the activity of the polypeptide, or its partial peptide or its amide, or a salt thereof.
(66) Use of (i) an antibody of the polypeptide according to (1) or (11) above, or its partial peptide or its amide, or a salt thereof, (ii) the antisense polynucleotide comprising the entire base sequence complementary or substantially complementary to the polynucleotide according to (6) or (16) above, or a part of the base sequence, or (iii) a compound or its salt that inhibits the activity of the polypeptide, or its partial peptide or its amide, or a salt thereof, for the manufacture of an agent for preventing/treating hypertension, anorexia, menopausal symptoms or insomnia.
(67) An antibody to the polypeptide according to (21) above, or its partial peptide or its amide, or a salt thereof
(68) A medicament comprising the antibody according to (67) above.
(69) A diagnostic agent comprising the antibody according to (67) above.
(70) The diagnostic agent according to (69) above, which is a diagnostic agent for sterility or hypothyroidism.
(70a) The diagnostic agent according to (69) above, which is a diagnostic agent for ovarian hypofunction, spermatic underdevelopment, menopausal symptoms or hyperthyroidism.
(71) An antisense polynucleotide comprising the entire base sequence complementary or substantially complementary to the polynucleotide according to (24) above, or a part of the base sequence.
(72) A medicament comprising the antisense polynucleotide according to (71) above.
(73) A medicament comprising a compound or its salt that inhibits the activity of the polypeptide according to (21) above, or its partial peptide or its amide, or a salt thereof.
(74) The medicament according to (68), (72) or (73) above, which is an agent for preventing/treating sterility or hypothyroidism.
(75) A method for preventing/treating sterility or hypothyroidism, which comprises inhibiting the activity of the polypeptide according to (21) above, or its partial peptide or its amide, or a salt thereof.
(76) A method for preventing/treating sterility or hypothyroidism, which comprises administering (i) an antibody to the polypeptide according to (21) above, or its partial peptide or its amide, or a salt thereof, (ii) an antisense polynucleotide comprising the entire base sequence complementary or substantially complementary to the polynucleotide according to (24) above, or a part of the base sequence, or (iii) a compound or its salt that inhibits the activity of the polypeptide according to (21) above, or its partial peptide or its amide, or a salt thereof.
(77) Use of (i) an antibody to the polypeptide according to (21) above, or its partial peptide or its amide, or a salt thereof, (ii) an antisense polynucleotide comprising the entire base sequence complementary or substantially complementary to the polynucleotide according to (24) above, or a part of the base sequence, or (iii) a compound or its salt that inhibits the activity of the polypeptide according to (21) above, or its partial peptide or its amide, or a salt thereof, for the manufacture of an agent for preventing/treating sterility or hypothyroidism.
(78) A non-human transgenic animal bearing the polynucleotide according to (6), (16) or (24) above, which is exogenous.
(79) A recombinant vector comprising the polynucleotide according to (6), (16) or (24) above, which is exogenous, and capable of expressing in a non-human animal.
(80) A non-human mammal embryonic stem cell, in which the polynucleotide according to (6), (16) or (24) above is inactivated.
(81) A non-human mammal deficient in expression of the polynucleotide according to (6), (16) or (24) above, in which said polynucleotide is inactivated.
(82) A method of screening a compound or its salt that promotes or inhibits the activity of a polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, which comprises using said polypeptide, or its partial peptide, or a salt thereof.
(83) A kit for screening a compound or its salt that promotes or inhibits the activity of a polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, which comprises said polypeptide, or its partial peptide, or a salt thereof.
(84) An agent for preventing/treating menopausal symptoms or hyperthyroidism, which comprises a compound or its salt that promotes the activity of a polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof.
(85) A method for preventing/treating menopausal symptoms or hyperthyroidism, which comprises promoting the activity of a polypeptide comprising the same or substantially the same amino acid sequence as the amino acid sequence represented by SEQ ID NO:37, SEQ ID NO: 38, SEQ ID NO:39, SEQ ID NO: 40, SEQ ID NO: 41 or SEQ ID NO: 42, or its partial peptide, or a salt thereof.
(86) A method for preventing/treating menopausal symptoms or hyperthyroidism, which comprises administering to a mammal an effective dose of a compound or its salt that promotes the activity of a polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof.
(87) Use of a compound or its salt that promotes the activity of a polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof, for the manufacture of an agent for preventing/treating menopausal symptoms or hyperthyroidism.
(88) An agent for preventing/treating sterility or hypothyroidism, which comprises a compound or its salt that inhibits the activity of a polypeptide comprising the same or substantially the same amino acid sequence as the amino acid sequence represented by SEQ ID NO: 37, SEQ ID NO: 38, SEQ ID NO:

39, SEQ ID NO: 40, SEQ ID NO: 41 or SEQ ID NO: 42, or its partial peptide, or a salt thereof.

(89) A method for preventing/treating sterility or hypothyroidism, which comprises inhibiting the activity of a polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof.

(90) A method for preventing/treating sterility or hypothyroidism, which comprises administering to a mammal an effective dose of a compound or its salt that inhibits the activity of a polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof.

(91) Use of a compound or its salt that inhibits the activity of a polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof, for the manufacture of an agent for preventing/treating sterility or hypothyroidism.

BEST MODE FOR CARRYING OUT THE INVENTION

The polypeptide having the amino acid sequence represented by SEQ ID NO: 1, SEQ ID NO: 2 or SEQ ID NO: 3, its amide, or a salt thereof is sometimes referred to as "neuromedin S".

The polypeptide having the amino acid sequence represented by SEQ ID NO: 7, SEQ ID NO: 9 or SEQ ID NO: 11, its amide, or a salt thereof is sometimes referred to as "neuromedin S N-terminal peptide-34".

The polypeptide having the amino acid sequence represented by SEQ ID NO: 8, SEQ ID NO: 10 or SEQ ID NO: 12, its amide, or a salt thereof is sometimes referred to as "neuromedin S N-terminal peptide-37".

The polypeptide having the amino acid sequence represented by SEQ ID NO: 4, SEQ ID NO: 5 or SEQ ID NO: 6, its amide, or a salt thereof is sometimes referred to as "neuromedin S precursor".

The polypeptide having the amino acid sequence represented by SEQ ID NO: 37, SEQ ID NO: 39 or SEQ ID NO: 41, its amide, or a salt thereof is sometimes referred to as "neuromedin U N-terminal peptide-33".

The polypeptide having the amino acid sequence represented by SEQ ID NO: 38, SEQ ID NO: 40 or SEQ ID NO: 42, its amide, or a salt thereof is sometimes referred to as "neuromedin U N-terminal peptide-36".

A protein having the amino acid sequence represented by SEQ ID NO: 25, SEQ ID NO: 27 or SEQ ID NO: 29 or a salt thereof is sometimes referred to as "TGR1".

A protein having the amino acid sequence represented by SEQ ID NO: 31, SEQ ID NO: 33 or SEQ ID NO: 35 or a salt thereof is sometimes referred to as "FM-3".

The polypeptide comprising the same or substantially the same amino acid sequence as the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12 (hereinafter sometimes referred to as the "polypeptide A of the present invention") and the polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42 (hereinafter sometimes referred to as the "polypeptide B of the present invention") may be any polypeptide derived from any cells of human and warm-blooded animals (e.g., guinea pig, rat, mouse, swine, sheep, bovine, monkey, dog, etc.) (e.g., splenocytes, nerve cells, glial cells, β cells of pancreas, pancreatic Langerhans islet, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.), or hematocyte type cells; or any tissues where such cells are present, such as brain or any of brain regions (e.g., olfactory bulb, amygdaloid nucleus, basal ganglia, hippocampus, thalamus, hypothalamus, subthalamic nucleus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, peripheral blood cells, prostate, testicles, ovary, placenta, uterus, bone, joint, skeletal muscle, etc.; the polypeptide may also be synthetic peptide.

The amino acid sequence comprising substantially the same amino acid sequence as that represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12 includes amino acid sequences having at least about 50% homology, preferably at least about 60% homology, more preferably at least about 70% homology, much more preferably at least about 80% homology, still more preferably at least about 90% homology and most preferably at least about 95% homology, to the amino acid sequence shown by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12; etc.

Homology of the amino acid sequences can be measured by using a homology scoring algorithm NCBI BLAST (National Center for Biotechnology Information Basic Local Alignment Search Tool).

Preferred examples of the polypeptides comprising substantially the same amino acid sequence as the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 111 or SEQ ID NO: 12 include polypeptides comprising substantially the same amino acid sequence as the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12 and having properties substantially equivalent to those of the polypeptides comprising the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, etc.

The substantially equivalent activity includes, for example, a ligand binding activity, signal transduction action, etc. The term substantially equivalent is used to mean that nature of the activity is equivalent in terms of quality. Thus, the ligand binding activity, signal transduction action, etc. is preferably equivalent (e.g., about 0.01 to 100 times, preferably about 0.5 to 20 times, more preferably 0.5 to 2 times), but differences in degree such as a level of these activities, quantitative factors such as a molecular weight of the polypeptide, etc. may be present and allowable.

The activities such as a ligand binding activity, a signal transduction action, etc. can be determined according to publicly known methods with some modifications thereof, for example, by the screening methods, etc., which will be later described.

Also, the polypeptides comprising the following amino acid sequences are used as the polypeptide A of the present invention: (i) the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, of which at least 1 or 2 (e.g., approximately 1 to 30, preferably approximately 1 to 10, more preferably several (1 to 5)) amino acids are deleted; (ii) the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, to which at least 1 or 2 (e.g., approximately 1 to 30, preferably approximately 1 to 10, and more preferably several (1 to 5)) amino acids are added; (iii) the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, wherein at least 1 or 2 (e.g., approximately 1 to 30, preferably approximately 1 to 10, and more preferably several (1 to 5)) amino acids are substituted by other amino acids; (iv) the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, into which at least 1 or 2 (e.g., approximately 1 to 30, preferably approximately 1 to 10, more preferably several (1 to 5)) amino acids are inserted; or (v) combination of the amino acid sequences described above; and the like.

Specific examples of the polypeptide A of the present invention, its amide, or a salt thereof include a polypeptide comprising the amino acid sequence represented by SEQ ID NO: 1, its amide, or a salt thereof, a polypeptide comprising the amino acid sequence represented by SEQ ID NO: 2, its amide, or a salt thereof, a polypeptide comprising the amino acid sequence represented by SEQ ID NO: 3, its amide, or a salt thereof, a polypeptide comprising the amino acid sequence represented by SEQ ID NO: 4, its amide, or a salt thereof, a polypeptide comprising the amino acid sequence represented by SEQ ID NO: 5, its amide, or a salt thereof, a polypeptide comprising the amino acid sequence represented by SEQ ID NO: 6, its amide, or a salt thereof, a polypeptide comprising the amino acid sequence represented by SEQ ID NO: 7, its amide, or a salt thereof, a polypeptide comprising the amino acid sequence represented by SEQ ID NO: 8, its amide, or a salt thereof, a polypeptide comprising the amino acid sequence represented by SEQ ID NO: 9, its amide, or a salt thereof, a polypeptide comprising the amino acid sequence represented by SEQ ID NO: 10, its amide, or a salt thereof, a polypeptide comprising the amino acid sequence represented by SEQ ID NO: 1, its amide, or a salt thereof, a polypeptide comprising the amino acid sequence represented by SEQ ID NO: 12, its amide, or a salt thereof, and the like.

The partial peptide of the polypeptide A of the present invention, its amide, or a salt thereof may be any polypeptide as long as it is a polypeptide available for the method of screening medicaments, etc. later described, and has the property substantially equivalent to that of the polypeptide A of the present invention. In terms of the number of amino acids in the partial peptide, there are used peptides containing, e.g., at least 5, preferably at least 10, preferably at least 15 and preferably at least 20 amino acid sequences, in the constituent amino acid sequence of the polypeptide A of the present invention; etc.

Herein, the term "substantially equivalent activity" has the same meaning as described above. The "substantially equivalent activity" can be assayed in the same manner as described above.

The partial peptides may be (i) those wherein at least 1 or 2 (preferably several (1 to 4)) amino acids are deleted of the amino acid sequences described above, (ii) those wherein at least 1 or 2 (preferably approximately 1 to 20, more preferably approximately 1 to 10 and most preferably several (1 to 5)) amino acids are added to the amino acid sequences described above, or (iii) those wherein at least 1 or 2 (preferably several (1 to 4)) amino acids are replaced with other amino acids.

Hereinafter, the polypeptide A of the present invention and its partial peptides are sometimes collectively referred to as the "polypeptide A of the present invention."

The amino acid sequence comprising substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42 includes amino acid sequences having at least about 50% homology, preferably at least about 60% homology, more preferably at least about 70% homology, much more preferably at least about 80% homology, still more preferably at least about 90% homology and most preferably at least about 95% homology, to the amino acid sequence shown by SEQ ID NO: 37, SEQ ID NO: 38, SEQ ID NO: 39, SEQ ID NO: 40, SEQ ID NO: 41 or SEQ ID NO: 42; etc.

Homology of the amino acid sequences can be measured by using a homology scoring algorithm NCBI BLAST (National Center for Biotechnology Information Basic Local Alignment Search Tool).

Preferred examples of the polypeptide comprising substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42 include polypeptide comprising substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42 and having properties substantially equivalent to those of the polypeptide comprising the amino acid sequence represented by SEQ ID NO: 37, SEQ ID NO: 38, SEQ ID NO: 39, SEQ ID NO: 40, SEQ ID NO: 41 or SEQ ID NO: 42, etc.

The substantially equivalent activity includes, for example, a ligand binding activity, a signal transduction action, and the like. The term substantially equivalent is used to mean that these activities are equivalent in terms of quality. Thus, the activities such as a ligand binding activity, signal transduction action, etc. are preferably equivalent (e.g., about 0.01 to 100 times, preferably about 0.5 to 20 times, more preferably 0.5 to 2 times), but differences in degree of these activities, quantitative factors such as a molecular weight of the polypeptide may be present and allowable.

The activities such as the ligand binding activity, signal transduction action, etc. can be determined according to publicly known methods with some modifications thereof, for example, by the screening methods later described; or the like.

Also, the polypeptides comprising the following amino acid sequences are used as the polypeptide B of the present invention: (i) the amino acid sequence represented by SEQ ID NO: 37, SEQ ID NO: 38, SEQ ID NO: 39, SEQ ID NO: 40, SEQ ID NO: 41 or SEQ ID NO: 42, of which at least 1 or 2 (e.g., approximately 1 to 30, preferably approximately 1 to 10 and more preferably several (1 to 5)) amino acids are deleted; (ii) the amino acid sequence represented by SEQ ID NO: 37, SEQ ID NO: 38, SEQ ID NO: 39, SEQ ID NO: 40, SEQ ID NO: 41 or SEQ ID NO: 42, to which at least 1 or 2 (e.g., approximately 1 to 30, preferably approximately 1 to 10, and more preferably several (1 to 5)) amino acids are added; (iii) the amino acid sequence represented by SEQ ID NO: 37, SEQ ID NO: 38, SEQ ID NO: 39, SEQ ID NO: 40, SEQ ID NO: 41 or SEQ ID NO: 42, wherein at least 1 or 2 (e.g., approximately 1 to 30, preferably approximately 1 to 10 and more preferably several (1 to 5)) amino acids are substituted by other amino acids; (iv) the amino acid sequence represented by SEQ ID NO: 37, SEQ ID NO: 38, SEQ ID NO: 39, SEQ ID NO: 40, SEQ ID NO: 41 or SEQ ID NO: 42, wherein at least 1 or 2 (e.g., approximately 1 to 30, preferably approximately 1 to 10 and more preferably several (1 to 5)) amino acids are inserted; or (v) combination of these amino acid sequences described above; and the like.

Specific examples of the polypeptide B of the present invention include a polypeptide having the amino acid sequence represented by SEQ ID NO: 37, a polypeptide having the amino acid sequence represented by SEQ ID NO: 38, a polypeptide having the amino acid sequence represented by SEQ ID NO: 39, a polypeptide having the amino acid sequence represented by SEQ ID NO: 40, a polypeptide having the amino acid sequence represented by SEQ ID NO: 41, a polypeptide having the amino acid sequence represented by SEQ ID NO: 42, etc.

The partial peptide of the polypeptide B of the present invention may be any polypeptide as long as it is a polypeptide available for the method of screening medicaments, etc., which will be later described and has properties substantially equivalent to those of the polypeptide B of the present invention. In terms of the number of amino acids in the partial peptide, there are used peptides containing, e.g., at least 5, preferably at least 10, preferably at least 15 and preferably at least 20 amino acid sequences, in the constituent amino acid sequence of the polypeptide B of the present invention; etc.

Herein, the term "substantially equivalent activity" has the same meaning as described above. The "substantially equivalent activity" can be assayed in the same manner as described above.

In the partial peptides, (i) at least 1 or 2 (preferably several (1 to 4)) amino acids may be deleted of the amino acid sequences described above, (ii) at least 1 or 2 (preferably approximately 1 to 20, more preferably approximately 1 to 10 and most preferably several (1 to 5)) amino acids may be added to the amino acid sequences described above, or (iii) at least 1 or 2 (preferably several (1 to 4)) amino acids in the amino acid sequences described above may be replaced with other amino acids.

Hereinafter, the polypeptide B of the present invention and its partial peptides are sometimes collectively referred to as the "polypeptide B of the present invention."

Likewise, the "polypeptide A of the present invention" and the "polypeptide B of the present invention" are sometimes collectively referred to as the "polypeptide of the present invention."

The protein comprising the same or substantially the same amino acid sequence as the amino acid sequence shown by SEQ ID NO: 25, SEQ ID NO: 27, SEQ ID NO: 29, SEQ ID NO: 31, SEQ ID NO: 33 or SEQ ID NO: 35, or salts thereof (hereinafter sometimes briefly referred to as the "protein of the present invention") may be any protein derived from any cell of human or mammals (e.g., guinea pig, rat, mouse, rabbit, swine, sheep, bovine, monkey, etc.) (e.g., splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); hemocyte type cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); or any tissues where such cells are present, such as brain or any of brain regions (e.g., olfactory bulb, amygdaloid nucleus, basal ganglia, hippocampus, thalamus, hypothalamus, subthalamic nucleus, cerebral cortex, medulla oblongata, cerebellum, occipital lobes, frontal lobe, lateral lobe, putamen, caudate nucleus, corpus callosum, substantia nigra), spinal cord, pituitary gland, stomach, pancreas, kidneys, liver, gonads, thyroid gland, gallbladder, bone marrow, adrenal glands, skin, muscle, lung, digestive tracts (e.g., large intestine, small intestine), vascular vessels, heart, thymus, spleen, submandibular gland, peripheral blood, peripheral blood cells, prostate, testicles, testes, ovaries, placenta, uterus, bones, joints, skeletal muscles, etc. (especially, brain and each region of the brain). The protein may also be a synthetic protein.

The amino acid sequence comprising substantially the same amino acid sequence as the amino acid sequence represented by SEQ ID NO: 25, SEQ ID NO: 27, SEQ ID NO: 29, SEQ ID NO: 31, SEQ ID NO: 33 or SEQ ID NO: 35 includes amino acid sequences having at least about 50% homology, preferably at least about 60% homology, more preferably at least about 70% homology, much more preferably at least about 80% homology, still more preferably at least about 90% homology and most preferably at least about 95% homology, to the amino acid sequence shown by SEQ ID NO: 25, SEQ ID NO: 27, SEQ ID NO: 29, SEQ ID NO: 31, SEQ ID NO: 33 or SEQ ID NO: 35; etc.

Homology of the amino acid sequences can be measured by using a homology scoring algorithm NCBI BLAST (National Center for Biotechnology Information Basic Local Alignment Search Tool).

Preferred examples of the protein comprising substantially the same amino acid sequence as the amino acid sequence represented by SEQ ID NO: 25, SEQ ID NO: 27, SEQ ID NO: 29, SEQ ID NO: 31, SEQ ID NO: 33 or SEQ ID NO: 35 include proteins comprising substantially the same amino acid sequence as the amino acid sequence represented by SEQ ID NO: 25, SEQ ID NO: 27, SEQ ID NO: 29, SEQ ID NO: 31, SEQ ID NO: 33 or SEQ ID NO: 35 and having properties substantially equivalent to those of the protein comprising the amino acid sequence represented by SEQ ID NO: 25, SEQ ID NO: 27, SEQ ID NO: 29, SEQ ID NO: 31, SEQ ID NO: 33 or SEQ ID NO: 35, etc.

The substantially equivalent activity includes, for example, a binding activity to the polypeptide of the present invention, a signal transduction action, and the like. The term substantially equivalent is used to mean that these activities are equivalent in terms of quality. Thus, the activities such as the binding activity to the peptide of the present invention, the signal transduction action, etc. are preferably equivalent (e.g., about 0.5 to 2 times), but differences in degree of these activities, quantitative factors such as a molecular weight of the protein may be present and allowable.

The activities such as the binding activity, the signal transduction action, etc. can be determined according to publicly known methods with some modifications thereof.

In addition, proteins comprising the following amino acid sequences are used as the protein of the present invention: (i) the amino acid sequence represented by SEQ ID NO: 25, SEQ ID NO: 27, SEQ ID NO: 29, SEQ ID NO: 31, SEQ ID NO: 33 or SEQ ID NO: 35, of which at least 1 or 2 (e.g., approximately 1 to 30, preferably approximately 1 to 10 and more preferably several (1 or 2)) amino acids are deleted; (ii) the amino acid sequence represented by SEQ ID NO: 25, SEQ ID NO: 27, SEQ ID NO: 29, SEQ ID NO: 31, SEQ ID NO: 33 or SEQ ID NO: 35, to which at least 1 or 2 (e.g., approximately 1 to 30, preferably approximately 1 to 10 and more preferably several (1 or 2)) amino acids are added; (iii) the amino acid sequence represented by SEQ ID NO: 25, SEQ ID NO: 27, SEQ ID NO: 29, SEQ ID NO: 31, SEQ ID NO: 33 or SEQ ID NO: 35, wherein at least 1 or 2 (e.g., approximately 1 to 30, preferably approximately 1 to 10 and more preferably several (1 or 2)) amino acids are substituted by other amino acids; or (iv) combination of these amino acid sequences described above; and the like.

Specific examples of the protein of the present invention include a protein comprising the amino acid sequence represented by SEQ ID NO: 25, a protein comprising the amino acid sequence represented by SEQ ID NO: 27, a protein comprising the amino acid sequence represented by SEQ ID NO: 29, a protein comprising the amino acid sequence represented by SEQ ID NO: 31, a protein comprising the amino acid sequence represented by SEQ ID NO: 33, a protein comprising the amino acid sequence represented by SEQ ID NO: 35, etc.

As the partial peptide of the protein of the present invention (hereinafter sometimes referred to as the partial peptide of the present invention), any partial peptide can be used so long as it is a partial peptide of the protein of the present invention described above. For example, among the protein molecules of the present invention, those having a site exposed to the outside of a cell membrane and having substantially equivalent ligand binding activities can be used.

A specific example of the partial peptide of the protein of the present invention is a peptide containing a domain analyzed to be an extracellular domain (hydrophilic site) in the hydrophobic plotting analysis. Also, a peptide containing a part of the hydrophobic domain can be used as well. Moreover, a peptide, which independently contains each domain, can also be used but may also be a peptide of the part wherein multiple domains are co-located.

The number of amino acids in the partial peptide of the present invention is at least 20, preferably at least 50 and more preferably at least 100 in the amino acid sequence that constitutes the protein of the present invention described above, and such peptides, etc. are preferred.

The substantially the same amino acid sequence refers to an amino acid sequence having at least about 50% homology, preferably at least about 60% homology, more preferably at least about 70% homology, still more preferably at least about 80% homology, much more preferably at least about 90% homology and most preferably at least about 95% homology, to these amino acid sequences.

Herein, the term "substantially equivalent ligand binding activity" has the same meaning as described above. The "substantially equivalent ligand binding activity" can be assayed by publicly known methods with modifications.

Further in the partial peptide of the present invention, at least 1 or 2 (preferably approximately 1 to 10 and more preferably several (1 or 2)) amino acids in the amino acid sequence represented by SEQ ID NO: 25, SEQ ID NO: 27, SEQ ID NO: 29, SEQ ID NO: 31, SEQ ID NO: 33 or SEQ ID NO: 35 may be deleted; at least 1 or 2 (preferably approximately 1 to 20, more preferably approximately 1 to 10 and most preferably several (1 or 2)) amino acids may be added to said amino acid sequence; or, at least 1 or 2 (preferably approximately 1 to 10, more preferably approximately 1 to 5 and most preferably several (1 or 2)) amino acids in said amino acid sequence may be replaced by other amino acids.

As salts of the polypeptide of the present invention or the protein of the present invention or its partial peptide, physiologically acceptable acid addition salts are particularly preferred. Examples of such salts include salts with inorganic acids (e.g., hydrochloric acid, phosphoric acid, hydrobromic acid and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid and benzenesulfonic acid), and the like.

Throughout the specification, the polypeptides and proteins of the present invention are represented in accordance with the conventional way of describing peptides, that is, the N-terminus (amino terminus) at the left hand and the C-terminus (carboxyl terminus) at the right hand. In the polypeptides comprising the amino acid sequence represented by SEQ ID NO: 1, etc., the C-terminus may be in the form of a carboxyl group (—COOH), a carboxylate (—COO$^-$), an amide (—CONH$_2$) or an ester (—COOR). Herein, examples of the ester group represented by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like, which is used widely as an ester for oral administration, may also be used.

In the polypeptide A of the present invention, the C-terminal carboxyl group (—COOH) is preferably in the form of an amide (—CONH$_2$).

Where the polypeptide of the present invention and the protein of the present invention (the polypeptide/protein of the present invention) contain a carboxyl group (or a carboxylate) at a position other than the C-terminus, the carboxyl group may be amidated or esterified and such an amide or ester is also included within the polypeptide/protein of the present invention. The aforesaid C-terminal esters or the like are used as the ester in this case.

The polypeptide/protein of the present invention also includes, in the peptides/proteins described above, those wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.); those wherein a substituent on the side chain of an amino acid in the molecule is protected with a suitable protecting group, or conjugated peptides/conjugated proteins such as so-called glycopeptides/glycoproteins having sugar chains; etc.

In the partial peptide of the present invention, the C-terminus may be in any form of a carboxyl group (—COOH), a carboxylate (—COO−), an amide (—CONH$_2$) or an ester (—COOR). Where the partial peptide of the present invention contains a carboxyl group (or a carboxylate) at a position other than the C-terminus, the carboxyl group may be amidated or esterified and such an amide or ester is also included within the partial peptide of the present invention. Examples of the ester group in this case may be the C-terminal esters described above, etc.

Furthermore, the partial peptide of the present invention includes, those wherein the amino group at the N-terminal methionine residue is protected with a protecting group; those wherein the N-terminal region is cleaved in vivo and Glu thus formed is pyroglutaminated; those wherein a substituent on the side chain of an amino acid in the molecule is protected with a suitable protecting group, or conjugated peptides such as so-called glycopeptides having sugar chains; etc., in the same way as in the protein of the present invention described above.

The polypeptide of the present invention or the protein of the present invention or salts thereof can be prepared from the human or mammalian cells or tissues described above by publicly known methods for purification of peptides/proteins, or can also be prepared by culturing a transformant bearing DNA encoding the protein of the present invention comprising the amino acid sequence represented by SEQ ID NO: 25, SEQ ID NO: 27, SEQ ID NO: 29, SEQ ID NO: 31, SEQ ID NO: 33 or SEQ ID NO: 35. They can also be prepared by the method for synthesis of peptides/proteins, which will be later described.

Where the polypeptide of the present invention or the protein of the present invention or salts thereof are prepared from the tissues or cells of human or mammal, the tissues or cells are homogenized, then extracted with an acid, an organic solvent, etc., and the extract can be purified and isolated by a combination of salting-out, dialysis, gel filtration, chromatography techniques such as reverse phase chromatography, ion exchange chromatography, affinity chromatography, or the like.

The polypeptide of the present invention can be prepared by publicly known methods for synthesis of polypeptides, or by cleaving polypeptides including the polypeptide of the present invention with an appropriate peptidase. For the methods for synthesis of polypeptides, for example, either solid phase synthesis or liquid phase synthesis may be used. In other words, the partial peptides or amino acids that can construct the polypeptide of the present invention are condensed with the remaining part. Where the product contains protecting groups, these protecting groups are removed to give the desired polypeptide. Publicly known methods for condensation and elimination of the protecting groups are described in (1) to (5) below.

(1) M. Bodanszky & M. A. Ondetti: Peptide Synthesis, Interscience Publishers, New York (1966)
(2) Schroeder & Luebke: The Peptide, Academic Press, New York (1965)
(3) Nobuo Izumiya, et al.: Peptide Gosei-no-Kiso to Jikken (Basics and experiments of peptide synthesis), published by Maruzen Co. (1975)
(4) Haruaki Yajima & Shunpei Sakakibara: Seikagaku Jikken Koza (Biochemical Experiment) 1, Tanpakushitsu no Kagaku (Chemistry of Proteins) IV, 205 (1977)
(5) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the polypeptide of the present invention can be purified and isolated by a combination of conventional methods for purification such as solvent extraction, distillation, column chromatography, liquid chromatography, recrystallization, etc. Where the polypeptide of the present invention obtained by the above methods is in a free form, it can be converted into an appropriate salt by a publicly known method or its modifications; where the polypeptide is obtained in a salt form, it can be converted into a free form by a publicly known method.

To synthesize amides of the polypeptide of the present invention, commercially available resins for peptide synthesis that are suitable for amide formation may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin, etc. Using these resins, amino acids, in which α-amino groups and functional groups on the side chains are appropriately protected, are condensed on the resin in accordance with the sequence of the objective peptide according to various condensation methods publicly known. At the end of the reaction, the polypeptide is excised from the resin and at the same time, the protecting groups are removed. Then, intramolecular disulfide bond forming reaction is performed in a highly diluted solution obtain the objective polypeptide.

For condensation of the protected amino acids described above, a variety of activation reagents for polypeptide synthesis may be used, and carbodiimides are particularly employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin. Solvents suitable for use to activate the protected amino acids or condense with the resin may be chosen from solvents that are known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the amino groups of starting amino acids include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc. Examples of the protecting groups for a carboxyl group include 2-adamantyl, 4-nitrobenzyl, 4-methoxybenzyl, 4-chlorobenzyl and phenacyl as well as benzyloxycarbonyl hydrazide, t-butoxycarbonyl hydrazide, trityl hydrazide, and the like, in addition to the $C_{1-6}$ alkyl group, $C_{3-8}$ cycloalkyl group and $C_{7-14}$ aralkyl group described as R above.

The hydroxyl group of serine and threonine can be protected through, for example, its esterification or etherification. Examples of groups appropriately used for the esterification include a lower alkanoyl group such as acetyl group, etc., an aroyl group such as benzoyl group, etc., and a group derived from carbon such as benzyloxycarbonyl group, ethoxycarbonyl group, etc. Examples of groups appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the amino acids in which the amino groups are activated in the starting material, the corresponding phosphoric amides, etc. are employed.

To eliminate (split off) the protecting groups, there are used catalytic reduction under hydrogen gas flow in the presence of a catalyst such as Pd-black, Pd-carbon, etc.; an acid treatment with anhydrous hydrogen fluoride, methanesulfonic acid, trifluoromethanesulfonic acid, trifluoroacetic acid, a mixture solution of these acids, etc.; a treatment with a base such as diisopropylethylamine, triethylamine, piperidine, piperazine, etc.; reduction with sodium in liquid ammonia, etc. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. described above, as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for producing the amides of the polypeptide, for example, the α-carboxyl group of the carboxy terminal amino acid is first protected by amidation; the peptide chain is then extended to a desired length toward the amino group side. Thereafter, a peptide in which only the protecting group of the N-terminal α-amino group in the peptide chain has been eliminated from the peptide and a peptide (or amino acids) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are eliminated by the method described above to give the desired crude polypeptide. This crude polypeptide is purified by various known purification means. Lyophilization of the major fraction gives the amide of the desired polypeptide.

To prepare the esterified polypeptide of the present invention, for example, the α-carboxyl group of the carboxy terminal amino acid is condensed with a desired alcohol to prepare the amino acid ester, which is followed by procedure similar to the preparation of the amidated polypeptide above to give the ester form of the desired polypeptide, in the same way as in the amide of the desired polypeptide.

The partial peptide of the polypeptide of the present invention can be prepared by digesting the polypeptide of the present invention with an appropriate peptidase or can be prepared in accordance with the aforesaid method for synthesis of polypeptides. The amide or ester of the partial peptide of the polypeptide of the present invention can also be prepared by a modification of the method for preparing the amide or ester described above. Also, salts of the partial peptide of the polypeptide of the present invention are the same as given for the salts of the polypeptide of the present invention described above.

Substantially the same substituent(s) of an amino acid(s) in the amino acid sequence can be selected, e.g., from other amino acids of the class to which the amino acid(s) belongs. Examples of nonpolar (hydrophobic) amino acids include alanine, leucine, isoleucine, valine, proline, phenylalanine, tryptophan, methionine, etc. Examples of polar (neutral) amino acids include glycine, serine, threonine, cystein, tyrosine, asparagine, glutamine, etc. Examples of positively charged (basic) amino acids include arginine, lysine, histidine, etc. Examples of negatively charged (acidic) amino acids include aspartic acid, glutamic acid, etc.

A labeled form of the polypeptides of the present invention, the partial peptides described in (1) above or the peptides described in (2) above includes those labeled with an isotope, those labeled with fluorescence (fluorescence labeling with, e.g., fluorescein, etc.), those labeled with biotin, those labeled with an enzyme, etc., by publicly known methods.

Specifically, the polypeptides of the present invention, which is labeled with [$^3$H], [$^{125}$I], [$^{14}$C], [$^{35}$S], etc. by publicly known methods, can be used.

The DNA encoding the polypeptide of the present invention or the protein of the present invention may be any DNA so long as it contains a DNA encoding the peptide comprising the same or substantially the same amino acid sequence as the amino acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 25, SEQ ID NO: 27, SEQ ID NO: 29, SEQ ID NO: 31, SEQ ID NO: 33 or SEQ ID NO: 35. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid, phagemid, etc. The DNA may also be directly amplified by reverse transcriptase polymerase chain reaction (hereinafter abbreviated as RT-PCR) using RNA fraction prepared from the cells and tissues described above.

(Cloning of DNA)

The DNA encoding the polypeptide of the present invention or the protein of the present invention can also be prepared by the following genetic engineering methods.

For cloning of the DNA that completely encodes the polypeptide of the present invention or the protein of the present invention, the DNA may be amplified by PCR using synthetic DNA primers containing a part of the base sequence of the polypeptide of the present invention or the protein of the present invention, or the DNA inserted into an appropriate vector can be selected by hybridization with a labeled DNA fragment or synthetic DNA that encodes a part or entire region of the polypeptide of the present invention or the protein of the present invention. The hybridization can be performed, for example, according to the method described in Molecular Cloning (2nd ed., J. Sambrook et al., Cold Spring Harbor Lab. Press, 1989). The hybridization may also be performed using commercially available library in accordance with the protocol described in the attached instructions. The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

Conversion of the base sequence of the DNA can be effected by publicly known methods such as the ODA-LA PCR method, the Gapped duplex method or the Kunkel method or its modifications by using publicly known kits available as Mutan™-super Express Km (manufactured by Takara Shuzo Co., Ltd.), Mutan™-K (manufactured by Takara Shuzo Co., Ltd.), etc.

The cloned DNA encoding the polypeptide of the present invention or the protein of the present invention can be used as it is, depending upon purpose or, if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof these translation initiation and termination codons may also be added by using an appropriate synthetic DNA adapter.

(Expression Vector)

The expression vector for the polypeptide of the present invention or the protein of the present invention can be manufactured, for example, by (i) excising the desired DNA fragment from the DNA encoding the polypeptide of the present invention or the protein of the present invention, and then (ii) ligating the DNA fragment with an appropriate expression vector downstream a promoter in the vector.

Examples of the vector include plasmids derived form *E. coli* (e.g., pBR322, pBR325, pUC12 or pUC13), plasmids derived from *Bacillus subtilis* (e.g., pUB110, pTP5 or pC194), plasmids derived from yeast (e.g., pSH19 or pSH15), bacteriophages such as λ phage, etc., animal viruses such as retrovirus, vaccinia virus, baculovirus, etc. The promoter used in the present invention may be any promoter if it matches well with a host to be used for gene expression.

In the case of using animal cells as the host, examples of the promoter include SV40-derived promoter, retroviral LTR promoter, metallothionein (HT) promoter, heatshock promoter, cytomegalovirus (CMV) promoter, SRα promoter, etc. Where the host is bacteria of the genus *Escherichia*, preferred examples of the promoter include trp promoter, T7 promoter, lac promoter, recA promoter, $\lambda P_L$ promoter, lpp promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH1 promoter, GAL promoter, etc. When insect cells are used as the host, preferred examples of the promoter include polyhedrin prompter, P10 promoter, etc.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as Neo, G418 resistance), etc. In particular, when dhfr gene is used as the selection marker in CHO (dhfr⁻) cells, selection can also be made on thymidine free media.

If necessary, a signal sequence that matches a host is added to the N-terminus of the polypeptide or its partial peptide. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; mating factor α (MFα) signal sequence, invertase signal sequence, etc. in the case of using yeast as the host; and insulin signal sequence, α-interferon signal sequence, antibody molecule signal sequence, etc. in the case of using animal cells as the host, respectively.

(Transformant)

Using the vector bearing the DNA encoding the polypeptide of the present invention thus constructed, transformants can be manufactured.

Examples of the host, which may be employed, are bacteria belonging to the genus *Escherichia*, bacteria belonging to the genus *Bacillus*, yeast, insects or insect cells, and animal cells, etc.

Specific examples of the bacteria belonging to the genus *Escherichia* include *Escherichia coli* K12 DH1 [Proc. Natl. Acad. Sci. U.S.A., 60, 160 (1968)), JM103 (Nucleic Acids Research, 9, 309 (1981)], JA221 [Journal of Molecular Biology, 120, 517 (1978)], HB101 [Journal of Molecular Biology, 41, 459 (1969)), C600 (Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R⁻, NA87-11A, DKD-5D, 20B-12, etc.

As the insect, for example, a larva of *Bombyx mori*, etc. can be used [Maeda, et al., Nature, 315, 592 (1985)].

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from Estigmena acrea, etc.; and for the virus BmNPV, *Bombyx mori* N cells (BmN cells), etc. are used. Examples of the Sf cell which can be used are Sf9 cells (ATCC CRL1711) and Sf21 cells [both cells are described in Vaughn, J. L. et al., In Vivo, 13, 213-217 (1977)], etc.

Examples of animal cells include monkey cells COS-7, Vero cells, Chinese hamster cells CHO, DHFR gene-deficient Chinese hamster cells CHO (dhfr⁻-CHO cells), mouse L cells, mouse 3T3 cells, mouse myeloma cells, human HEK293 cells, human FL cells, 293 cells, C127 cells, BALB3T3 cells, Sp-2/O cells, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in Virology, 52, 456 (1973).

Methods for introducing the expression vectors into the cells include, for example, the lipofection method [Proceedings of the National Academy of Sciences of the United States of America, 84, 7413 (1987)], the calcium phosphate method [Virology, 52, 456-467 (1973)], the electroporation method [EMBO J., 1, 841-845 (1982)], etc.

As described above, the transformant transformed by the expression vector comprising the DNA encoding the protein of the present invention or the polypeptide of the present invention can be obtained.

Methods for stably expressing the protein of the present invention or the polypeptide of the present invention using animal cells include methods of selecting the cells by clone selection in which the expression vectors described above are introduced into chromosomes. Specifically, transformants can be selected based on the selection markers described above. Further, repeated clone selections on the transformants thus obtained using the selection markers enable to acquire stable animal cell lines capable of highly expressing the protein of the present invention or the polypeptide of the present invention. Furthermore, when the dhfr gene is used as the selection marker, incubation may be carried out by gradually increasing the concentration of MTX to select resistant cells, whereby the DNA encoding the protein of the present invention or the polypeptide of the present invention is amplified in the cells concurrently with the dhfr gene to acquire animal cell lines with higher expression.

The transformants described above are cultured under conditions capable of expressing the DNA encoding the protein of the present invention or the polypeptide of the present invention to produce and accumulate the protein of the present invention or the polypeptide of the present invention, whereby the protein of the present invention or the polypeptide of the present invention can be produced.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431-433, Cold Spring Harbor Laboratory, New York, 1972). If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultivated generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 to about 72 hours. If necessary, the culture can be aerated or agitated.

Where insect cells or insects are used as the host, the transformant is cultivated in, for example, Grace's Insect Medium (Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 to 5 days and, if necessary and desired, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 to 60 hours and, if necessary and desired, the culture can be aerated or agitated.

Especially when CHO (dhfr⁻) cells and dhfr gene are used as selection markers, it is preferred to use substantially thymidine-free DMEM medium supplemented with dialyzed fetal calf serum.

(Separation and Purification of the Protein of the Present Invention or the Polypeptide of the Present Invention)

The protein of the present invention or the polypeptide of the present invention can be separated and purified from the culture described above, e.g., by the procedures described below.

When the protein of the present invention or the polypeptide of the present invention is extracted from the culture or cells, after incubation the transformants or cells are collected by a publicly known method and suspended in an appropriate buffer. The transformants or cells are then disrupted by publicly known methods such as ultrasonication, a treatment with lysozyme and/or freeze-thaw cycling, followed by centrifugation, filtration, etc. Thus, the crude extract of the protein of the present invention or the polypeptide of the present invention can be obtained. The buffer used for the procedures may contain a protein modifier such as urea or guanidine hydrochloride, or a surfactant such as Triton (registered trademark) X-100, etc.

When the protein of the present invention or the polypeptide of the present invention is released in the culture, after completion of the incubation the supernatant can be separated from the transformants or cells to collect the supernatant by a publicly known method.

The protein of the present invention or the polypeptide of the present invention contained in the culture supernatant or the extract thus obtained can be purified by appropriately combining publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis, chromatofocusing, etc.; and the like.

In the case where the protein of the present invention or the polypeptide of the present invention thus obtained is in a free form, it can be converted into its salts by publicly known methods or modifications thereof. On the other hand, when the protein or polypeptide is obtained in the form of a salt, it can be converted into its free form or into a different salt by publicly known methods or modifications thereof.

The protein of the present invention or the polypeptide of the present invention produced by the recombinant can be treated, prior to or after the purification, with an appropriate protein modifying enzyme to appropriately modify the same or partially remove a protein ((poly)peptide). Examples of the protein-modifying enzyme include trypsin, chymotrypsin, arginyl endopeptidase, protein kinase, glycosidase, or the like. The Edman degradation using the Edman reagent (phenyl isothiocyanate), which is publicly known, can be used to delete the N-terminal amino acid.

The presence of the thus produced protein of the present invention or the polypeptide of the present invention can be assayed by an enzyme immunoassay using a specific antibody, or the like.

(Antibody)

The present invention further provides antibodies to the polypeptide of the present invention.

The antibodies to the polypeptide of the present invention may be any of polyclonal antibodies and monoclonal antibodies, as long as they are capable of recognizing the polypeptide of the present invention.

The antibodies to the polypeptide of the present invention may be manufactured by publicly known methods for producing antibodies or antisera, using as antigens the polypeptide of the present invention.

[Preparation of Monoclonal Antibody]

(a) Preparation of Monoclonal Antibody-Producing Cell

The polypeptide of the present invention is administered to a mammal either solely or together with carriers or diluents to the site where antibody production is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the applicable mammals are monkeys, rabbits, dogs, guinea pigs, mice, rats, sheep and goats, with mice and rats being preferred.

In the preparation of monoclonal antibody-producing cells, warm-blooded animals, e.g., mice, immunized with an antigen wherein the antibody titer is noted is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting a labeled form of the polypeptide of the present invention, which will be described below, with the antiserum followed by assaying the binding activity of the labeling agent bound to the antibody. The fusion may be operated, for example, by the known Koehler and Milstein method [Nature, 256, 495 (1975)]. Examples of the fusion accelerator are polyethylene glycol (PEG), Sendai virus, etc., of which PEG is preferably employed.

Examples of the myeloma cells are NS-1, P3U1, SP2/0, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to 40° C., preferably at about 30 to 37° C. for about 1 to 10 minutes, an efficient cell fusion can be performed.

Various methods can be used for screening of the monoclonal antibody-producing hybridoma. Examples of such methods include a method which comprises adding the supernatant of hybridoma to a solid phase (e.g., microplate) adsorbed with an antigen of the polypeptide of the present invention directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the polypeptide A of the present invention labeled with a radioactive substance or an enzyme and detecting the monoclonal antibody bound to the solid phase.

The monoclonal antibody can be selected by publicly known methods or by modifications of these methods. In general, selection can be effected in a medium for animal cells supplemented with HAT (hypoxanthine, aminopterin and thymidine). Any selection and growth medium can be used as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for incubation of a hybridoma (SFM-101, Nissui Seiyaku Co., Ltd.), etc. can be used for the selection and growth medium. Incubation is carried out generally at 20 to 40° C., preferably at about 37° C., for 5 days to 3 weeks, preferably 1 to 2 weeks. The incubation can be conducted normally under 5% carbon dioxide gas. The antibody titer of the culture supernatant of hybridomas can be determined in the same way as in the assay for the antibody titer in antisera described above.

(b) Purification of Monoclonal Antibody

Separation and purification of the monoclonal antibody can be carried out by methods applied to conventional separation and purification of immunoglobulins, in the same way as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

[Preparation of Polyclonal Antibody]

The polyclonal antibody of the present invention can be produced by publicly known methods or their modifications. For example, a complex of immunogen (polypeptide antigen of the present invention) and a carrier protein is prepared, and a mammal is immunized with the complex in a manner similar to the method described above for the production of monoclonal antibodies. The product containing the antibody to the polypeptide A of the present invention is collected from the immunized animal followed by separation and purification of the antibody.

In the complex of an immunogen and a carrier protein used to immunize a mammal, the type of carrier protein and the mixing ratio of a carrier to hapten may be any type in any ratio, as long as the antibody is efficiently produced to the hapten immunized by crosslinking to the carrier. For example, bovine serum albumin, bovine thyroglobulins, keyhole limpet hemocyanin, etc. is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to warmblooded animals either solely or together with carriers or diluents to the site in which the antibody can be produced by the administration. In order to potentiate the antibody productivity upon the administration, complete Freund's adjuvant or incomplete Freund's adjuvant may be administered. The administration is usually made once approximately in every about 2 to 6 weeks and about 3 to about 10 times in total.

The polyclonal antibody can be collected from the blood, ascites, etc., preferably from the blood, ascites, etc. of mammals immunized by the method described above.

The polyclonal antibody titer in antiserum can be assayed by the same procedure as used for determination of the serum antibody titer described above. The separation and purification of the polyclonal antibody can be carried out in accordance with the method for the separation and purification of immunoglobulins performed as applied to the separation and purification of monoclonal antibodies described hereinabove.

The antibody of the present invention described above is capable of specifically recognizing the polypeptide of the present invention. Therefore, the antibody can be used to quantify the polypeptide of the present invention in a test fluid, especially by the sandwich immunoassay, etc. In other words, the present invention provides, for example, the following quantification methods: (i) a method of quantifying the polypeptide of the present invention in a test fluid, which comprises reacting the antibody of the present invention competitively with the test fluid and a labeled form of the polypeptide of the present invention, and measuring the ratio of the labeled polypeptide of the present invention bound to the antibody; and, (ii) a method of quantifying the polypeptide of the present invention in a test fluid, which comprises reacting the test fluid with the antibody of the present invention immobilized on a carrier and a labeled form of the antibody of the present invention simultaneously or sequentially, and measuring the activity of the label on the immobilizing carrier.

In the quantification method (ii) described above, it is preferred that one antibody recognizes the N-terminal region of the polypeptide of the present invention, and another antibody reacts with the C-terminal region of the polypeptide of the present invention.

Using the monoclonal antibodies to the polypeptide of the present invention (hereinafter sometimes referred to as the monoclonal antibodies to the present invention), the polypeptide of the present invention can be quantified. In addition, the polypeptide of the present invention can also be detected by tissue staining, or the like. For these purposes, the antibody molecule itself may be used, or $F(ab')_2$, Fab' or Fab fraction of the antibody molecule may also be used.

The quantification methods of the polypeptide of the present invention using the antibodies of the present invention are not particularly limited. Any quantification method can be used, so long as the amount of an antibody, antigen, or antibody-antigen complex corresponding to the amount of antigen (e.g., the amount of the polypeptide of the present invention) in a test fluid can be detected by chemical or physical means and the amount of the antigen can be calculated from a standard curve prepared from standard solutions containing known amounts of the antigen. For example, the nephrometry, competitive method, immunometric method and sandwich method are appropriately used, with the sandwich method described below being most preferable in terms of sensitivity and specificity.

As the labeling agent for the methods using labeled substances, there are employed, for example, radioisotopes, enzymes, fluorescent substances, luminescent substances, etc. For the radioisotope, for example, $[^{125}I]$, $[^{131}I]$, $[^{3}H]$, $[^{14}C]$, etc. are used. As the enzyme described above, stable enzymes with a high specific activity are preferred; for example, β-galactosidase, β-glucosidase, alkaline phosphatase, peroxidase, malate dehydrogenase, etc. are used. Examples of the fluorescent substance used are fluorescamine and fluorescein isothiocyanate are used. For the luminescent substance, there are used, for example, luminol, luminol derivatives, luciferin, and lucigenin. Furthermore, the biotin-avidin system may be used for binding an antibody or antigen to the labeling agent.

For immobilization of an antigen or antibody, physical adsorption may be used. Chemical binding methods conventionally used for insolubilization or immobilization of the protein, enzymes, etc. may also be used. For the carrier, for example, insoluble polysaccharides such as agarose, dextran, cellulose, etc.; synthetic resin such as polystyrene, polyacrylamide, silicon, etc., glass, and the like are used.

In the sandwich method, the monoclonal antibody of the present invention which is immobilized is reacted with a test fluid (primary reaction), then with a labeled form of the monoclonal antibody of the present invention (secondary reaction), and the activity of the label on the immobilizing carrier is measured, whereby the amount of the polypeptide A of the present invention in the test fluid can be quantified. The order of the primary and secondary reactions may be reversed, and the reactions may be performed simultaneously or with an interval. The labeling agent and the method for immobilization can be performed by some modifications of those described above.

In immunoassay by the sandwich method, the antibody used for immobilized or labeled antibodies is not necessarily one species, but a mixture of two or more antibodies may be used to increase the measurement sensitivity.

In the methods of assaying the polypeptide of the present invention by the sandwich method according to the present invention, antibodies that bind to different sites of the polypeptide of the present invention are preferably used as the monoclonal antibodies of the present invention for the primary and secondary reactions. That is, in the antibodies used for the primary and secondary reactions are, for example, when the antibody used in the secondary reaction recognizes the C-terminal region of the polypeptide of the present invention, it is preferable to use the antibody recognizing the region other than the C-terminal region for the primary reaction, e.g., the antibody recognizing the N-terminal region.

The monoclonal antibody of the present invention can be used for other assay systems than the sandwich method, for example, for competitive method, immunometric method, nephrometry, or the like. In the competitive method, an antigen in a test fluid and a labeled antigen are competitively reacted with an antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, etc., and an immobilized method either using an immobilized antibody as the primary antibody, or using a soluble antibody as the primary antibody and immobilized antibody as the secondary antibody.

In the immunometric method, an antigen in a test fluid and an immobilized antigen are competitively reacted with a given amount of labeled antibody, the solid phase is separated from the liquid phase, or an antigen in a test fluid and an excess amount of labeled antibody are reacted, the immobilized antigen is then added to bind the unreacted labeled antibody to the solid phase, and the solid phase is separated from the liquid phase. Then, the amount of the label in either phase is measured to quantify the antigen in the test fluid.

In the nephrometry, the insoluble precipitate produced after the antigen-antibody reaction in gel or solution is quantified. When the amount of an antigen in the test fluid is small and only a small amount of the precipitate is obtained, laser nephrometry using scattering of laser is advantageously employed.

For applying these individual immunological methods to the quantification methods of the present invention, any particular conditions or procedures are not required. Systems for measuring the polypeptide of the present invention are constructed by adding the usual technical consideration in the art to the conventional conditions and procedures. For the details of these general technical means, reference can be made to the following reviews and texts. For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Enzyme immunoassay" (2nd ed.) (Igakushoin, published in 1982), Eiji Ishikawa, et al. ed. "Enzyme immunoassay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing).

As above, the polypeptide of the present invention can be quantified with good sensitivity, by using the antibody of the present invention.

Moreover, quantification of the polypeptide of the present invention in vivo using the antibody of the present invention enables to diagnose various diseases associated with dysfunction of the polypeptide of the present invention.

The antibody of the present invention can also be used to detect the polypeptide of the present invention, which is present in a test sample such as a body fluid, a tissue, etc. The antibody can also be used to prepare an antibody column used for purification of the polypeptide of the present invention, detect the polypeptide of the present invention in each fraction upon purification, analyze the behavior of the polypeptide of the present invention in the cells under investigation; etc.

(Antisense Polynucleotide)

The antisense polynucleotide comprising a complementary or substantially complementary base sequence to the base sequence of a DNA encoding the polypeptide of the present invention (hereinafter these DNAs are sometimes collectively referred to as the DNA of the present invention in description of the antisense polynucleotide) can be any antisense polynucleotide, so long as it possesses a base sequence complementary or substantially complementary to the base sequence of the DNA of the present invention and capable of suppressing the expression of said DNA, but antisense DNA is preferred.

The base sequence substantially complementary to the DNA of the present invention includes, for example, a base sequence having at least about 70% homology, preferably at least about 80% homology, more preferably at least about 90% homology and most preferably at least about 95% homology, to the entire base sequence or to its partial base sequence (i.e., complementary strand to the DNA of the present invention), and the like. In particular, the antisense polynucleotide having at least about 70% homology, preferably at least about 80% homology, more preferably at least about 90% homology and most preferably at least about 95% homology, to the complementary strand of the base sequence which encodes the N-terminal region of the protein of the present invention (e.g., the base sequence around the initiation codon, etc.) is preferred in the entire base sequence of the complementary strand to the DNA of the present invention.

Specific examples are antisense polynucleotides comprising the entire or part of base sequence complementary or substantially complementary to a base sequence of DNA comprising the base sequence represented by SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 45, SEQ ID NO: 48 or SEQ ID NO: 51, etc.

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. These antisense polynucleotides may be synthesized using a publicly known DNA synthesizer, etc.

According to the present invention, the antisense polynucleotide that can inhibit the replication or expression of a gene encoding the polypeptide of the present invention can be designed and synthesized based on the cloned or determined base sequence information of the DNA encoding the polypeptide. Such a polynucleotide can hybridize to RNA of a gene encoding the polypeptide of the present invention and inhibit RNA synthesis or the function of RNA, or can regulate/ control the expression of a gene encoding the polypeptide of the present invention via interaction with RNAs associated with the polypeptide of the present invention. Polynucleotides complementary to the specified sequences of RNA associated with the polypeptide of the present invention and polynucleotides that can specifically hybridize to RNA associated with the polypeptide of the present invention are useful for regulating/controlling the expression of a gene encoding the polypeptide of the present invention in vivo and in vitro. These polynucleotides are also useful for the treatment or diagnosis of diseases, etc.

The term "corresponding" is used to mean homologous or complementary to a particular sequence of the nucleotide including the gene, base sequence or nucleic acid. The term "corresponding" between nucleotides, base sequences or nucleic acids and polypeptides usually refer to amino acids of a polypeptide under instructions derived from the sequence of nucleotides (nucleic acids) or their complements. The 5' end hairpin loop, 5' end 6-base-pair repeats, 5' end untranslated region, polypeptide translation initiation codon, polypeptide coding region, translation termination codon, 3' untranslated region, 3' end palindrome region, and 3' end hairpin loop encoding the polypeptide can be selected as preferred target regions, though any other region can be selected as a target in the genes encoding the polypeptide.

The relationship between the targeted nucleic acid and the polynucleotide complementary to at least a part of the target region can be denoted to be "antisense." Examples of the antisense polynucleotide include a polynucleotide containing 2-deoxy-D-ribose, a polynucleotide containing D-ribose, any other type of polynucleotide which is N-glycoside of a purine or pyrimidine base, or other polymers having non-nucleotide backbones or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.) or saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense polynucleotide of the present invention can be modified preferably based on the following design, that is, by (1) increasing the intracellular stability of the antisense polynucleotide, (2) enhancing the cell permeability of the antisense polynucleotide, (3) increasing the affinity of the nucleic acid to the targeted sense strand to a higher level, or (4) minimizing the toxicity, if any, of the antisense polynucleotide.

Most of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense polynucleotide of the present invention may contain altered or modified sugars, bases or linkages, may be provided in a specialized form such as liposomes, microspheres, or may be applied to gene therapy, or may be provided in combination with attached moieties. Such attached moieties used include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol, and the like.

The inhibition activity of the antisense polynucleotide can be investigated using the transformant of the present invention, the in vivo or in vitro gene expression system of the present invention, or the in vivo or in vitro translation system of the polypeptide of the present invention. The nucleic acid can be applied to cells by various methods publicly known.

Hereinafter, the polypeptide comprising the same or substantially the same amino acid sequence as the amino acid sequence represented by SEQ ID NO: 1, SEQ ID NO: 2, SEQ ID NO: 3, SEQ ID NO: 4, SEQ ID NO: 5 or SEQ ID NO: 6, or its partial peptide or amide, or salt thereof, is sometimes briefly referred to as the "polypeptide A1 of the present invention."

Hereinafter, the polypeptide comprising the same or substantially the same amino acid sequence as the amino acid sequence represented by SEQ ID NO: 7, SEQ ID NO: 8, SEQ ID NO: 9, SEQ ID NO: 10, SEQ ID NO: 11 or SEQ ID NO: 12, or its partial peptide or amide, or salt thereof, is sometimes briefly referred to as the "polypeptide A2 of the present invention."

Hereinafter, the polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide or amide, or salt thereof, is sometimes briefly referred to as the "polypeptide B of the present invention."

[1] Screening Method and Screening Kit for Drug Candidate Compound

The method of screening drug candidate compounds which comprises using the polypeptide of the present invention and the kit for screening drug candidate compounds which comprises the polypeptide of the present invention are described below (hereinafter sometimes briefly referred to as the "screening method of the present invention" and the "screening kit of the present invention," respectively).

(Method for Screening a Compound or its Salt that Promotes or Inhibits the Activity of the Polypeptide of the Present Invention)

The polypeptide of the present invention is useful as a reagent for screening a compound or its salt that promotes or inhibits the activity of the polypeptide of the present invention.

The method for screening a compound or its salt that promotes or inhibits the activity (function) of the polypeptide of the present invention (hereinafter sometimes simply referred to as the promoter or inhibitor), which comprises using the polypeptide of the present invention, includes 1) to 3) below.

1) The activity (prolactin release suppressing activity, etc.) of the polypeptide A1 of the present invention is assayed and compared between (i) the case where the polypeptide A1 of the present invention is brought in contact with cells and (ii) the case where the polypeptide A1 of the present invention and a test compound are brought in contact with cells, to screen the promoter or inhibitor.

In the screening method described above, for example, the cells are incubated in the cases (i) and (ii) and the amount of prolactin released is measured. Cells or the like, in which prolactin release is induced, are preferably used as the cells described above. For instance, rat anterior pituitary cells (e.g., eosinophilic cells), etc. are employed. Any medium can be used so long as it is a medium that does not interfere with the activities possessed by the polypeptide A1 of the present invention, such as the prolactin release suppressing activity; for example, DMEM (Dulbecco modified Eagle's medium), etc. is used. The amount of prolactin released can be determined by publicly known methods, e.g., radioimmunoassay using RIA (radioimmunoassay) kit (manufactured by Amersham, etc.). Examples of the test compound are peptides, proteins, antibodies, non-peptide compounds, synthetic compounds, fermentation products, cell extracts, plant extracts, animal tissue extracts, blood plasma, etc. These compounds may be novel compounds or known compounds.

When a test compound promotes the activity (e.g., the prolactin release suppressing activity) of the polypeptide A1 of the present invention in the case (ii) described above by at least about 20%, preferably at least 30% and more preferably at least about 50%, as compared to the case (i) above, the test compound can be selected as a compound or its salt that promotes the activity of the polypeptide A1 of the present invention. For example, when a test compound inhibits the activity (e.g., the prolactin release suppressing activity) of the polypeptide A1 of the present invention in the case (ii) described above by at least about 20%, preferably at least 30% and more preferably at least about 50%, as compared to the case (i) above, the test compound can be selected as a compound or its salt that inhibits the activity of the polypeptide A1 of the present invention.

2) The activity (prolactin releasing activity, etc.) of the polypeptide A2 of the present invention is assayed and compared between (iii) the case where the polypeptide A2 of the present invention is brought in contact with cells and (iv) the case where the polypeptide A2 of the present invention and a test compound are brought in contact with cells, to screen the promoter or inhibitor.

In the screening method described above, for example, the cells are incubated in the cases (iii) and (iv) and the amount of prolactin released is measured. The cells which are preferably used are cells where prolactin release is induced, or the like. For instance, rat anterior pituitary cells (e.g., eosinophilic cells), etc. are employed. Any medium can be used so long as it is a medium that does not interfere with the activities such as the prolactin releasing activity possessed by the polypeptide A2 of the present invention; e.g., DMEM (Dulbecco modified Eagle's medium) or the like is used. The amount of prolactin released can be determined by publicly known methods, e.g., radioimmunoassay using RIA (radioimmunoassay) kit (manufactured by Amersham, etc.). The test compound includes, for example, peptides, proteins, antibodies, non-peptide compounds, synthetic compounds, fermentation products, cell extracts, plant extracts, animal tissue extracts, blood plasma, etc. These compounds may be novel compounds or known compounds.

For example, when a test compound promotes the activity (e.g., prolactin releasing activity) of the polypeptide A2 of the present invention in the case (iv) described above by at least about 20%, preferably at least 30% and more preferably at least about 50%, as compared to the case (iii) above, the test compound can be selected as a compound or its salt that promotes the activity of the polypeptide A2 of the present invention. For example, when a test compound inhibits the activity (e.g., prolactin releasing activity) of the polypeptide A2 of the present invention in the case (iv) described above by at least about 20%, preferably at least 30% and more preferably at least about 50%, as compared to the case (iii) above, the test compound can be selected as a compound or its salt that inhibits the activity of the polypeptide A2 of the present invention.

3) The activity (prolactin releasing activity, etc.) of the polypeptide B of the present invention is assayed and compared between (v) the case where the polypeptide B of the present invention is brought in contact with cells and (vi) the case where the polypeptide B of the present invention and a test compound are brought in contact with cells, to screen the promoter or inhibitor.

In the screening method described above, for example, the cells are incubated in the cases (v) and (vi) and the amount of prolactin released is measured. The cells which are preferably used are cells where prolactin release is induced, or the like. For instance, rat anterior pituitary cells (e.g., eosinophilic cells), etc. are employed. Any medium can be used so long as it is a medium that does not interfere with the activities such as the prolactin releasing activity, etc., possessed by the polypeptide B of the present invention, and, for example, DMEM (Dulbecco modified Eagle's medium) or the like is employed. The amount of prolactin released can be determined by publicly known methods, e.g., radioimmunoassay using RIA (radioimmunoassay) kit (manufactured by Amersham, etc.). The test compound includes, for example, peptides, antibodies, proteins, non-peptide compounds, synthetic compounds, fermentation products, cell extracts, plant extracts, animal tissue extracts, blood plasma, etc. These compounds may be novel compounds or known compounds.

For example, when a test compound promotes the activity (e.g., prolactin releasing activity) of the polypeptide B of the present invention in the case (vi) described above by at least about 20%, preferably at least 30% and more preferably at least about 50%, as compared to the case (v) above, the test compound can be selected as a compound or its salt that promotes the activity of the polypeptide B of the present invention. For example, when a test compound inhibits the activity (e.g., prolactin releasing activity) of the polypeptide B of the present invention in the case (vi) described above by at least about 20%, preferably at least 30% and more preferably at least about 50%, as compared to the case (v) above, the test compound can be selected as a compound or its salt that inhibits the activity of the polypeptide B of the present invention.

(Kit for Screening the Compound or its Salt that Promotes or Inhibits the Activity of the Polypeptide of the Present Invention)

The kit for screening the compound or its salt that promotes or inhibits the activity of the polypeptide of the present invention comprises the polypeptide of the present invention or its salt. Preferably, the kit further comprises reagents for assaying the polypeptide of the present invention, such as reagents for assaying prolactin (e.g., RIA kit, etc.), and the like.

Examples of the screening kits of the present invention include those comprising (a) and (b) below.

(a) Assay Buffer and Wash Buffer

Hanks' balanced salt solution (manufactured by Gibco, Inc.) supplemented with 0.05% bovine serum albumin (manufactured by Sigma, Inc.)

The solution is sterilized by filtration through a 0.45 μm filter, and stored at 4° C. or may be prepared at use.

(b) Standard Preparation of the Polypeptide of the Present Invention

The polypeptide of the present invention is dissolved in PBS supplemented with 0.1% bovine serum albumin (manufactured by Sigma) to become 1 mM, and the solution is stored at −20° C.

(Method for Screening a Compound or its Salt that Alters the Binding Properties of the Polypeptide of the Present Invention and the Protein of the Present Invention)

The method of screening a compound or its salt that alters the binding properties of the polypeptide of the present invention and the protein (e.g., TGR1 or FM-3) of the present invention, which comprises using the polypeptide of the present invention, or the kit for screening a compound or its salt that alters the binding properties of the polypeptide of the present invention and the protein of the present invention, which comprises the polypeptide of the present invention and the protein of the present invention are described below in detail (hereinafter sometimes briefly referred to as the "screening method of the present invention" and the "screening kit of the present invention," respectively).

By using the protein of the present invention, or by constructing the expression system of a recombinant form of the protein of the present invention and using the binding assay system to the polypeptide of the present invention (ligand-receptor assay system) through the expression system, the compound or its salt that alters the binding properties of the polypeptide of the present invention and the protein of the present invention (e.g., peptides, proteins, antibodies, non-peptide compounds, synthetic compounds, fermentation products, cell extracts, plant extracts, animal tissue extracts, blood plasma, etc.) can be screened.

Such compounds include compounds having the cell-stimulating activity (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH change, etc.) mediated by the protein of the present invention (i.e., agonists), compounds that do not have the cell-stimulating activity (i.e., antagonists), and the like.

The term "alters the binding properties of the polypeptide of the present invention and the protein of the present invention" is used to include both cases where binding of the polypeptide of the present invention to the protein of the present invention is inhibited and promoted.

Thus, the present invention provides the method of screening a compound or its salt that alters the binding properties of the polypeptide of the present invention and the protein of the present invention, which comprises comparing (i) the case wherein the polypeptide of the present invention is brought in contact with the protein of the present invention and (ii) the case wherein the polypeptide of the present invention and a test compound are brought in contact with the protein of the present invention.

According to the screening method of the present invention, the method comprises assaying, (i) when the polypeptide of the present invention is brought in contact with the protein of the present invention described above and (ii) when the polypeptide of the present invention and a test compound are brought in contact with the protein of the present invention described above, for example, the binding amount of a ligand to the protein of the present invention, the cell-stimulating activity (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH change, etc.) or the like is assayed and comparison is made between (i) and (ii).

Specific examples of the screening method of the present invention include:

(1) a method of screening a compound or its salt that alters the binding properties of the polypeptide of the present invention and the protein of the present invention, which comprises measuring binding amounts of the polypeptide of the present invention to the protein of the present invention when a labeled form of the polypeptide of the present invention, which is shown as a derivative of the polypeptide of the present invention (hereinafter merely referred to as the "labeled polypeptide of the present invention"), is brought in contact with the protein of the present invention and when the labeled polypeptide of the present invention and a test compound are brought in contact with the protein of the present invention; and comparing the binding amounts;

(2) a method of screening a compound or its salt that alters the binding amounts of the polypeptide of the present invention and the protein of the present invention, which comprises measuring binding amounts of the polypeptide of the present invention and a cell containing the polypeptide of the present invention or a membrane fraction of the cell, when the labeled polypeptide of the present invention is brought in contact with the cell containing the protein of the present invention or the membrane fraction of the cell and when the labeled polypeptide of the present invention and a test compound are brought in contact with the cell containing the protein of the present invention or the membrane fraction of the cell, and comparing the binding amounts;

(3) a method of screening a compound or its salt that alters the binding properties of the polypeptide of the present invention and the protein of the present invention, which comprises assaying the binding amount of the labeled polypeptide of the present invention to the protein of the present invention, in the case wherein the labeled polypeptide of the present invention is brought in contact with the protein of the present invention expressed in a cell membrane by culturing a transformant containing a DNA encoding the protein of the present invention and in the case wherein the labeled polypeptide of the present invention and a test compound are brought in contact with the protein of the present invention expressed in a cell membrane by culturing a transformant containing a DNA encoding the protein of the present invention, and comparing the properties;

(4) a method of screening a compound or its salt that alters the binding properties of the polypeptide of the present invention and the protein of the present invention, which comprises assaying the cell-stimulating activity (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH change, etc.) mediated by the protein of the present invention, when a compound that activates the protein of the present invention (e.g., the polypeptide of the present invention) is brought in contact with a cell containing the protein of the present invention and when a compound that activates the protein of the present invention and a test compound are brought in contact with a cell containing the protein of the present invention, and comparing the properties; and, (5) a method of screening a compound or its salt that alters the binding properties of the polypeptide of the present invention and the protein of the present invention, which comprises assaying the cell-stimulating activity (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH change, etc.) mediated by the protein of the present invention, when a compound that activates the protein of the present invention (e.g., the polypeptide of the present invention) is brought in contact with the protein of the present invention expressed in a cell membrane by culturing a transformant containing a DNA encoding the protein of the present invention and when a compound that activates the protein of the present invention and a test compound are brought in contact with the protein of the present invention expressed on a cell membrane by culturing a transformant containing a DNA encoding the protein of the present invention, and comparing the properties; and the like.

The screening method of the present invention will be described below more specifically.

First, the protein of the present invention, which is used for the screening method of the present invention, may be any protein, so long as it contains the protein of the present invention and preferably it is a membrane fraction of organs, etc. from human or mammal. However, it is very difficult to obtain human-derived organs among others, and the protein of the present invention, or the like, expressed abundantly using recombinants are suitable for use in the screening.

To produce the protein of the present invention, the aforesaid methods, etc. are used.

When cells containing the protein of the present invention, membrane fractions of these cells, or the like are used in the screening method of the present invention, these cells or membrane fractions may be prepared by the procedures later described.

Where cells containing the protein of the present invention, e.g., TGR1, are employed, the cells may be fixed using glutaraldehyde, formalin, etc. The fixation can be made by publicly known methods.

The cells containing TGR1 refer to host cells where TGR1 is expressed, and such host cells include *Escherichia coli*, *Bacillus subtilis*, yeast, insect cells, animal cells, etc. described above.

The cell membrane fraction is used to mean a fraction abundant in cell membrane obtained by cell disruption and subsequent fractionation by publicly known methods. The cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, and the like. Cell membrane fractionation is effected mainly by fractionation using a centrifugal force, such as fractional centrifugation, density gradient centrifugation, etc. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in TGR1 expressed and membrane components such as cell-derived phospholipids, membrane proteins, etc.

The amount of TGR1 in the cells or cell membrane fractions containing the TGR1 is preferably $10^3$ to $10^8$ molecules, more preferably $10^5$ to $10^7$ molecules, per cell. As the amount of expression increases, the ligand binding activity per unit of the membrane fraction increases so that not only the highly sensitive screening system can be constructed but also large quantities of samples can be assayed on the same lot.

To perform the methods (1) to (3) for screening the compound or its salt that alters the binding properties of the polypeptide of the present invention and the protein of the present invention, an appropriate fraction of the protein of the present invention and a labeled ligand or a compound having the ligand activity (such as the polypeptide of the present invention) are employed. For the fraction of the protein of the present invention, a fraction from naturally occurring type of the protein of the present invention or a fraction from recombinant type of the protein of the present invention having activities equivalent thereto, or the like, are desirable. Herein, the equivalent activity is used to mean ligand binding activities, etc., which are equivalent. For the labeled ligand or the compound having the ligand activity, there are used a labeled ligand or a compound having the ligand activity (such as the polypeptide of the present invention), etc. A ligand labeled with, e.g., $[^3H]$, $[^{125}I]$, $[^{14}C]$, $[^{35}S]$, etc. (a labeled form of the polypeptide of the present invention), etc. can be utilized.

Specifically, the screening of a compound that alters the binding properties of the polypeptide of the present invention and the protein of the present invention can be performed by the following procedures. First, a standard receptor preparation is produced by suspending cells containing the protein of the present invention or their membrane fractions in a buffer appropriate for screening. Any buffer can be used so long as it does not interfere with ligand-receptor binding, such buffer including a phosphate buffer, a Tris-HCl buffer, etc. having pH of 4 to 10 (desirably pH of 6 to 8). For the purpose of minimizing non-specific binding, a surfactant such as CHAPS, Tween-80™ (manufactured by Kao-Atlas Inc.), digitonin, deoxycholate, etc. may be added to the buffer. Further for the purpose of suppressing degradation of the protein of the present invention or the polypeptide of the present invention by a protease, a protease inhibitor such as PMSF, leupeptin, E-64 (manufactured by Peptide Institute, Inc.), pepstatin, etc. may also be added. A given quantity (5,000 cpm to 500,000 cpm) of the labeled polypeptide of the present invention (a labeled form of the polypeptide of the present invention) is added to 0.01 ml to 10 ml of the receptor solution, and at the same time, $10^{-4}$ to $10^{-1}$ μM of a test compound is allowed to be co-present. To determine the amount of non-specific binding (NSB), a reaction tube containing a large excess of the polypeptide of the present invention in an unlabeled form is also provided. The reaction is carried out at 0° C. to 50° C., preferably about 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity in the glass fiber filter paper is then measured by means of a liquid scintillation counter or a γ-counter. When the nonspecific binding (NSB) is subtracted from the count ($B_0$) when any antagonizing compound is absent and the thus obtained count ($B_0$−NSB) is made 100%, a test compound having the specific binding (B−NSB) of, e.g., 80% or less, can be selected as a candidate substance capable of altering the binding properties of the protein of the present invention and the polypeptide of the present invention.

For assaying the binding of the protein of the present invention to the polypeptide of the present invention, BIAcore (manufactured by Amersham Pharmacia Biotech Co.) may also be employed. In this technique, the polypeptide of the present invention is immobilized onto a sensor chip by the amino coupling method following the protocol attached to the device. A buffer such as phosphate buffer, Tris buffer, etc., which contains the protein of the present invention purified from the cells containing the protein of the present invention or transformants containing a DNA encoding the protein of the present invention, or a membrane fraction containing the protein of the present invention, or the purified protein of the present invention or a membrane fraction containing the protein of the present invention and a test compound, is passed over the sensor chip at a flow rate of 2 to 20 μl/min. By monitoring that the test compound co-present alters the change in surface plasmon resonance caused by binding of the protein of the present invention to the polypeptide of the present invention on the sensor chip, the compound that alters the binding of the protein of the present invention to the polypeptide of the present invention can be screened. According to this technique, the alteration can be likewise determined by the procedure which involves immobilizing the protein of the present invention onto a sensor chip and passing over the sensor chip a buffer solution such as phosphate buffer, Tris buffer, etc., which contains the polypeptide of the present invention and a test compound. Examples of the test compound are the same as those given above.

The method (4) or (5) described above for screening the compound that alters the binding properties of the polypeptide of the present invention and the protein of the present invention can be performed as follows. For example, the cell stimulating activity (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH change, etc.) mediated by the protein of the present invention can be assayed by publicly known methods, or using assay kits commercially available. Specifically, the cells containing the protein of the present invention are first cultured on a multiwell plate, etc. Prior to screening, the medium is replaced with fresh medium or cell with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., arachidonic acid, etc.) due to a degrading enzyme contained in the cells, an inhibitor against such as a degrading enzyme may be added prior to the assay. For detecting the activity such as the cAMP production suppression, the baseline production in the cells is increased by forskolin or the like and the suppressing effect on the increased baseline production can be detected.

For screening by assaying the cell stimulating activity, cells in which the protein of the present invention is expressed, are required. Preferred examples of the cells, in which the protein of the present invention is expressed, are cell lines, etc., in which a recombinant type of the protein of the present invention described above is expressed. The cell, wherein the protein of the present invention is expressed and which is a transformant, may be either a stably expressed strain or a temporarily expressed strain. For animal cells, the aforesaid cells of the same type are employed as well.

Examples of the test compounds include peptides, proteins, antibodies, non-peptide compounds, synthetic compounds, fermentation products, cell extracts, plant extracts, animal tissue extracts, blood plasma, etc.

In more detail, the following assay systems used for the aforesaid ligand-receptor assay system are described below.

(1) When the receptor-expressed cells are stimulated by a receptor agonist, G protein in the cells is activated and GTP is bound thereto. This phenomenon is monitored also in a membrane fraction of the receptor-expressed cells. Usually, GTP is hydrolyzed and changes to GDP. When GTPγS is previously added to the reaction solution, GTPγS is bound to G protein as in GTP, but is not hydrolyzed so that the state bound to the G protein-containing cell membrane is maintained. When labeled GTPγS is used, the radioactivity remained on the cell membrane can be measured to assay the receptor-expressed cell stimulating activity of receptor agonist. Using this reaction, the stimulating activity of the polypeptide of the present invention on the cells where the protein of the present invention is expressed. Though this method is carried out using the membrane fraction containing the protein of the present invention as in (1) to (3), not using the cells containing the protein of the present invention as in (4) or (5) described above, the cell stimulating activity is assayed in the method as in (4) or (5). According to this assay method, the substance showing the activity of promoting the binding of GTPγS to the membrane fraction containing the protein of the present invention is an agonist, the compound that alters the binding properties of the polypeptide of the present invention and the protein of the present invention can be screened by adding the polypeptide of the present invention or the polypeptide of the present invention and a test compound and monitoring that changes occur in the GTPγS binding promoting activities on the membrane fraction expressing the protein of the present invention, when compared to single administration of the polypeptide of the present invention. Thus, the compound showing the activity of suppressing the GTPγS binding promoting activity against the membrane fraction of cells capable of expressing the protein of the present invention by the polypeptide of the present invention can be selected as a candidate substance capable of altering the binding properties of the protein of the present invention and the polypeptide of the present invention. On the other hand, an agonist can be screened as well by administering a test compound alone and monitoring the GTPγS binding promoting activity on the membrane fraction of cells expressing the protein of the present invention.

A specific example of the screening method is specifically described below. The membrane fraction containing the protein of the present invention, which is prepared by the procedure described above, is diluted in a buffer for membrane dilution (50 mM Tris, 5 mM $MgCl_2$, 150 mM NaCl, 1 μM GDP, 0.1% BSA, pH 7.4). A dilution ratio varies depending upon the amount of a receptor expressed. The dilution is dispensed by 0.2 ml each in Falcon 2053, to which the polypeptide of the present invention or the polypeptide of the present invention and a test compound is/are added, and [$^{35}$S] GTPγS is further added to the mixture in a final concentration of 200 μM. After maintaining at 25° C. for an hour, ice-cooled wash buffer (50 mM Tris, 5 mM $MgCl_2$, 150 mM NaCl, 0.1% BSA, 0.05% CHAPS, pH 7.4, 1.5 ml) is added to the mixture followed by filtration through a glass fiber filter paper GF/F. After keeping at 65° C. for 30 minutes, the mixture is dried and the radioactivity of [$^{35}$S] GTPγS bound to the membrane fraction remained on the filter paper is measured with a liquid scintillation counter. When the radioactivity in the experimental zone added with only the polypeptide of the present invention is defined as 100% and the radioactivity in the experimental zone without adding the polypeptide of the present invention is defined as 0%, an effect of the test compound on the GTPγS binding promoting activity by the polypeptide of the present invention is calculated. The test compound showing the GTPγS binding promoting activity of, for example, 80% or less can be selected as a candidate substance capable of altering the binding properties of the protein of the present invention and the polypeptide of the present invention.

(2) In the cells where the protein of the present invention is expressed, the intracellular cAMP level is reduced by stimulation of the polypeptide of the present invention. Using this reaction, the stimulating activities of the polypeptide of the present invention on the cells where the protein of the present invention is expressed can be assayed.

The level of cAMP produced in the cells where the protein of the present invention is expressed can be assayed by the RIA system using an anti-cAMP antibody, whose antibody is obtained from immunized mouse, rat, rabbit, goat, bovine, etc., and [$^{125}$I]-labeled cAMP (both commercially available) or by the EIA system using an anti-cAMP antibody and labeled cAMP in combination. It is also possible to quantify by the SPA method, using beads, which contain scintillants bearing anti-cAMP antibodies immobilized using protein A or antibodies to IgG, etc. of the animal used to produce the anti-cAMP antibodies (using, e.g., the kit manufactured by Amersham Pharmacia Biotech, Inc.).

According to this method, the compound that alters binding of the polypeptide of the present invention to the protein of the present invention can be screened by increasing the intracellular cAMP level by a ligand such as forskolin, calcitonin, etc. capable of increasing the intracellular cAMP level, adding the polypeptide of the present invention or the polypeptide of the present invention and a test compound, and monitoring the suppression of the intracellular cAMP level altered by single administration of the polypeptide of the present invention. In this case, the compound that shows an activity of inhibiting the cAMP production suppression activity in cells, in which the protein of the present invention is expressed, by the polypeptide of the present invention can be selected as a candidate substance capable of altering the binding properties of the protein of the present invention and the polypeptide of the present invention. On the other hand, a compound showing the agonist activity can be screened by monitoring the cAMP production suppressing activity when a test compound alone is added.

The screening method is described below more specifically. CHO cells where the protein of the present invention is expressed are plated on a 24-well plate in $5\times10^4$ cells/well followed by incubation for 48 hours. The cells are washed with Hanks' buffer (pH 7.4) supplemented with 0.2 mM 3-isobutyl-methylxanthine, 0.05% BSA and 20 mM HEPES (hereinafter Hanks' buffer (pH 7.4) supplemented with 0.2 mM 3-isobutyl-methylxanthine, 0.05% BSA and 20 mM HEPES is simply referred to as the reaction buffer). Thereafter, 0.5 ml of the reaction buffer is added to the cells and the mixture is kept warm in an incubator for 30 minutes. The reaction buffer is removed and 0.25 ml of a fresh reaction buffer is added to the cells. Then, 0.25 ml of a 2 μM forskolin-containing reaction buffer, in which 1 μM of the polypeptide of the present invention or 1 μM of the polypeptide of the present invention and a test compound is/are incorporated, is added to the cells, followed by reacting at 37° C. for 24 minutes. The reaction is terminated by adding 100 μl of 20% perchloric acid. The reaction mixture is then put on ice for an hour to extract intracellular cAMP. The amount of cAMP in the extract is measured using a cAMP EIA kit (Amersham Pharmacia Biotech). Taking the amount of cAMP produced by forskolin stimulation as 100% and the amount of cAMP inhibited by addition of 1 μM of the polypeptide of the present invention as 0%, an effect of the test compound on the cAMP production suppressing activity by the polypeptide of the present invention is calculated. The test compound that inhibits the activity of the polypeptide of the present invention to increase the cAMP producing activity, e.g., to 80% or more, can be selected as a candidate substance capable of altering the binding properties of the protein of the present invention and the polypeptide of the present invention.

To determine the cAMP production promoting activity, the cAMP produced by adding a test compound to CHO cells, in which the protein of the present invention is expressed, without adding forskolin, is quantified by the procedure described above. In this case, a test compound showing the cAMP producing activity to increase, e.g., to 10% or more, can be selected as a candidate substance capable of altering the binding properties of the protein of the present invention and the polypeptide of the present invention.

(3) A DNA containing CRE (cAMP response element) is inserted into a multicloning site upstream a luciferase gene in PicaGene Basic Vector or PicaGene Enhancer Vector (Toyo Ink Mfg. Co., Ltd.), which is made a CRE-reporter gene vector. In a CRE-reporter gene vector-transfected cell, stimulation associated with increase of cAMP induces the expression of CRE-mediated luciferase gene and luciferase protein production subsequent thereto. In other words, by assaying the luciferase activity, changes in cAMP level in the CRE-reporter gene vector transfected cell can be detected. Utilizing the cells wherein the protein of the present invention is expressed, to which the CRE-reporter gene vector is transfected, a compound that alters the binding of the polypeptide of the present invention to the protein of the present invention can be screened. The screening method is specifically described below.

The CRE-reporter gene transfected cells in which the protein of the present invention is expressed are plated on a 24-well plate in $5\times10^3$ cells/well followed by incubation for 48 hours. The cells are washed in Hanks' buffer (pH 7.4) supplemented with 0.2 mM 3-isobutylmethylxanthine, 0.05% BSA and 20 mM HEPES (hereinafter Hanks' buffer (pH 7.4) supplemented with 0.2 mM 3-isobutylmethylxanthine, 0.05% BSA and 20 mM HEPES is referred to as the reaction buffer). Thereafter, 0.5 ml of the reaction buffer is added to the cells and the mixture is kept warm in an incubator for 30 minutes. The reaction buffer is removed and 0.25 ml of a fresh reaction buffer is added to the cells. Then, 1 nM the polypeptide of the present invention or 1 nM the polypeptide of the present invention and a test compound as well as 0.25 ml of the reaction buffer containing 2 μM forskolin are added to the cells followed by reacting at 37° C. for 24 minutes. The cells are dissolved in a cell lysis agent for PicaGene (Toyo Ink Mfg. Co., Ltd.) and a luminescence substrate (Toyo Ink Mfg. Co., Ltd.) is added to the lysate. Luminescence emitted by luciferase is measured by a luminometer, a liquid scintillation counter or a top counter. An effect of the compound that alters the binding of the polypeptide of the present invention to the protein of the present invention can be assayed by comparing the luminescence amounts of luciferase with the case where the polypeptide of the present invention is administered solely. In this case, an increase of the luminescence amount by forskolin stimulation is suppressed by administration of the polypeptide of the present invention. The compound that can retrieve the suppression can be selected as a candidate substance capable of altering the binding properties of the protein of the present invention and the polypeptide of the present invention. On the other hand, an agonist can be screened as well by administering a test compound alone and monitoring suppression of the luminescence amount intensified by forskolin stimulation in the same way as in the polypeptide of the present invention.

In addition to luciferase, alkaline phosphatase, chloramphenicol acetyltransferase or β-galactosidase can be employed as the reporter gene. The enzymatic activity of gene products from these reporter genes can be readily assayed using assay kits commercially available, as described below. The alkaline phosphatase activity, the chloramphenicol acetyltransferase activity and the β-galactosidase activity can be assayed using, e.g., Lumi-Phos 530 manufactured by Wako Pure Chemical Industries, Ltd., FAST CAT chloramphenicol Acetyltransferase Assay Kit manufactured by Wako Pure Chemical Industries, Ltd. and Aurora Gal-XE manufactured by Wako Pure Chemical Industries, Ltd., respectively.

(4) When the cells where the protein of the present invention is expressed are stimulated by the polypeptide of the present invention to release arachidonic acid metabolites extracellularly, arachidonic acid having radioactivity is previously incorporated into the cells, and the activity can be determined by assaying the extracellularly released radioactivity. In this case, the polypeptide of the present invention or the polypeptide of the present invention and a test compound is/are added to monitor the effect of the polypeptide of the present invention on the arachidonic acid metabolite releasing activity. Thus, a compound that affects the binding of the polypeptide of the present invention to the protein of the present invention can be screened. In this case, a compound that inhibits the arachidonic acid metabolite-releasing activity can be selected as a candidate substance capable of altering the binding properties of the protein of the present invention and the polypeptide of the present invention. Also, by adding a test compound alone and monitoring the arachidonic acid metabolite-releasing activity in the cell in which the protein of the present invention is expressed, a compound showing the agonist activity can be screened as well.

The screening method which affects the binding of the polypeptide of the present invention to the protein of the present invention is described below more specifically.

CHO cells where the protein of the present invention is expressed are plated on a 24-well plate in $5 \times 10^4$ cells/well. After incubation for 24 hours, [$^3$H] arachidonic acid is added to the cells in 0.25 μCi/well. Sixteen hours later, the cells are washed in Hanks' buffer (pH 7.4) supplemented with 0.05% BSA and 20 mM HEPES. To each well is added 5001 of the reaction buffer containing the polypeptide of the present invention in the final concentration of 10 μM, or the polypeptide of the present invention in the final concentration of 10 μM and a test compound. After incubation at 37° C. for 60 minutes, 400 μl of the reaction solution is charged in a scintillator and the amount of [$^3$H] arachidonic acid metabolites released in the reaction solution is measured using a scintillation counter. When 10 nM of the buffer alone, in which the polypeptide of the present invention is not added, is added, the amount of [$^3$H] arachidonic acid metabolites is taken as 0% and the amount of [$^3$H] arachidonic acid metabolites is taken as 100% when the buffer to which 10 nM of the polypeptide of the present invention is added (no test compound is added). Thus, an effect on the binding of the polypeptide of the present invention to the protein of the present invention is calculated. A compound showing the arachidonic acid metabolite-releasing activity of, e.g., 50% or less, can be selected as a candidate substance capable of altering the binding properties of the protein of the present invention and the polypeptide of the present invention.

(5) When the cells in which the protein of the present invention is expressed are stimulated by the polypeptide of the present invention, an intracellular $Ca^{2+}$ ion level increases. By utilizing this, effects of a test compound on the binding of the polypeptide of the present invention to the protein of the present invention can be monitored.

The cells in which the protein of the present invention is expressed are inoculated on a sterilized cover glass for microscopy. Two days after, the culture medium is replaced by HBSS in which 4 mM Fura-2 AM (Dojin Kagaku Kenkyusho) is suspended, which is then allowed to stand at room temperature for 2 hours and 30 minutes. After washing with HBSS, the cover glass is set on a cuvette, and an increased ratio of the fluorescence intensity at 505 nm is measured with a fluorescence spectrophotometer at excited wavelengths of 340 nm and 380 nm, when the polypeptide of the present invention or the polypeptide of the present invention and a test compound is/are added. In this case, a compound that affects the binding of the polypeptide of the present invention to the protein of the present invention can be screened by measuring changes in fluorescence intensity caused by addition of the test compound, as compared to the case where the polypeptide of the present invention is administered solely. Also, FLIPR (manufactured by Molecular Device) may be used as described below. That is, Fluo-3 AM (manufactured by Dojin Kagaku Kenkyusho) is added to a cell suspension to incorporate Fluo-3 AM into the cells. The supernatant is then washed several times through centrifugation and the cells are inoculated on a 96-well plate. After setting in the FLIPR device, the polypeptide of the present invention or the polypeptide of the present invention and a test compound is/are added in the same way as in the case of Fura-2. A compound that affects the binding of the polypeptide of the present invention to the protein of the present invention can be screened by measuring changes in fluorescence intensity caused by addition of the test compound, as compared to the case where the polypeptide of the present invention is administered solely. In these cases, a compound that suppresses an increase of the fluorescence intensity by the polypeptide of the present invention can be selected as a candidate substance capable of altering the binding properties of the protein of the present invention and the polypeptide of the present invention. On the other hand, an agonist can also be screened by monitoring an increase of the fluorescence intensity when a test compound alone is added.

In the cells in which the protein of the present invention is expressed, when a gene of protein such as aequorin, etc. that emits light in response to an increase of intracellular $Ca^{2+}$ ions is co-expressed and aequorin changes to the Ca-bound type by an increase of intracellular $Ca^{2+}$ ion level to emit light. Utilizing this light emission, a compound that affects the binding of the polypeptide of the present invention to the protein of the present invention can be screened by adding the polypeptide of the present invention or the polypeptide of the present invention and a test compound and monitoring that light emission observed by addition of the test compound changes, as compared to the case where the polypeptide of the present invention alone is administered. The method is the same as described above, except that the fluorescent substance is not incorporated into the cells.

(6) It is known that when a receptor agonist is added to a receptor-expressing cell, the level of intracellular inositol triphosphate increases. By monitoring the reaction in the cell expressing the protein of the present invention, which is induced by the polypeptide of the present invention, a compound that affects the binding of the polypeptide of the present invention to the protein of the present invention can be screened. On one day after inoculation of the cells on a 24-well plate, myo-[2-$^3$H]inositol (2.5 microCi/well) is added to each well and incubated for one day in this medium. After thoroughly washing, the polypeptide of the present invention or the polypeptide of the present invention and a test compound is/are added to the cells. The reaction is then terminated by adding 10% perchloric acid. The reaction mixture is neutralized with 1.5 M KOH and 60 mM HEPES solution and then passed through a column packed with 0.5 ml of Ag1×8 resin (Bio-Rad). After washing with 5 mM $Na_2BO_3$ and 60 mM $HCOONH_4$, the radioactivity eluted with 1M $HCOONH_4$ and 0.1M HCOOH is measured with a liquid scintillation counter. When the radioactivity in the medium of the reaction buffer without adding the polypeptide of the present invention is made 0% and the radioactivity in the medium added with the polypeptide of the present invention is made 100%, the effect of a test compound on the binding of the polypeptide of the present invention to the protein of the present invention is calculated. A test compound showing the inositol triphosphate production activity of, e.g., 50% or less can be selected as a candidate substance capable of altering the binding properties of the protein of the present invention and the polypeptide of the present invention. On the other hand, an agonist can be screened similarly by monitoring an increase of the inositol triphosphate production when the test compound alone is added.

(7) A DNA containing TRE (TPA response element) is inserted into a multicloning site upstream a luciferase gene in PicaGene Basic Vector or PicaGene Enhancer Vector (Toyo Ink Mfg. Co., Ltd.), which is made a TRE-reporter gene vector. In a TRE-reporter gene vector-transfected cell, stimulation accompanied by an increase of intracellular $Ca^{2+}$ induces the expression of TRE-mediated luciferase gene and then the production of luciferase protein. That is, by assaying the luciferase activity, changes in calcium ion level in the TRE-reporter gene vector-transfected cell can be detected. Utilizing the TRE-reporter gene vector-transfected the cells in which the protein of the present invention is expressed, a compound that alters the binding of the polypeptide of the present invention to the protein of the present invention can be screened. The screening method is specifically described below.

The TRE-reporter gene-transfected the cells in which the protein of the present invention is expressed are inoculated on a 24-well plate in $5 \times 10^3$ cells/well followed by incubation for 48 hours. After the cells are washed in Hanks buffer (pH 7.4) supplemented with 0.05% BSA and 20 mM HEPES, 10 nM of the polypeptide of the present invention or 10 nM of the polypeptide of the present invention and a test compound is/are added to the cells, followed by reacting at 37° C. for 60 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is measured by a luminometer, a liquid scintillation counter or a top counter. Effects of a compound that alters the binding of the polypeptide of the present invention to the protein of the present invention can be measured by comparing the luminescence amount by luciferase with the case when the polypeptide of the present invention alone is added. In this case, the amount of luminescence increases with an increase in intracellular $Ca^{2+}$ by administration of the polypeptide of the present invention and a compound that suppresses the increase can be selected as a candidate substance capable of altering the binding properties of the protein of the present invention and the polypeptide of the present invention. On the other hand, an agonist can also be screened as well by monitoring an increase of the luminescence in the same way as in the polypeptide of the present invention, when a test compound alone is administered.

In addition to luciferase, alkaline phosphatase, chloramphenicol acetyltransferase or β-galactosidase may be employed as the reporter gene. The enzymatic activity of gene products from these reporter genes can easily be assayed as described below, using assay kits commercially available. The alkaline phosphatase activity, the chloramphenicol acetyltransferase activity and the β-galactosidase activity can be assayed using, e.g., Lumi-Phos 530 manufactured by Wako Pure Chemical Industries, Ltd., FAST CAT chloramphenicol Acetyltransferase Assay Kit manufactured by Wako Pure Chemical Industries, Ltd. and Aurora Gal-XE manufactured by Wako Pure Chemical Industries, Ltd., respectively.

(8) In the cell in which the protein of the present invention is expressed in response to the polypeptide of the present invention, growth is observed by MAP kinase activation. This growth can be assayed by the MAP kinase activity, thymidine uptake or cell counting (MTT, etc.). By utilizing this, a compound that alters the binding of the polypeptide of the present invention to the protein of the present invention can be screened.

The MAP kinase activity can readily be assayed by adding the polypeptide of the present invention or the polypeptide of the present invention and a test compound to the cells, obtaining a MAP kinase fraction from a cell lysate by immunoprecipitation using an anti-MAP kinase antibody and then using, e.g., MAP Kinase Assay Kit manufactured by Wako Pure Chemical Industries, Ltd. and γ-[$^{32}$P]-ATP. The thymidine uptake activity can be assayed by inoculating the cells in which the protein of the present invention is expressed, adding the polypeptide of the present invention or the polypeptide of the present invention and a test compound to the cells, further adding [methyl-3H]-thymidine, causing cell lysis and then counting the radioactivity of the labeled thymidine taken up into the cells with a liquid scintillation counter.

The growth of cells in which the protein of the present invention is expressed can also be determined by inoculating the expressed cells, adding the polypeptide of the present invention or the polypeptide of the present invention and a test compound, further adding MTT (3-(4,5-dimethyl-2-thiazolyl)-2,5-diphenyl-2H-tetrazolium bromide), allowing MTT to be taken up into the cells thereby to convert into MTT formazan, causing cell lysis with isopropanol rendered acidic with hydrochloric acid, and then measuring the absorption at 570 nm.

The method of screening a compound that alters the binding of the polypeptide of the present invention to the protein of the present invention utilizing the labeled thymidine uptake activity is specifically described below.

The cells in which the protein of the present invention is expressed are inoculated on a 24-well plate in 5000 cells/well followed by incubation for one day. Next, the cells are incubated in a serum-free medium for 2 days to bring the cells under starvation. The polypeptide of the present invention or the polypeptide of the present invention and a test compound is/are added to the cells. After incubation for 24 hours, [methyl-3H] thymidine is added in 0.015 MBq/well followed by incubation for 6 hours. After washing the cells with PBS(−), methanol is added to the cells. The mixture is allowed to stand for 10 minutes. Next, 5% trichloroacetic acid is added and the mixture is allowed to stand for 15 minutes. The immobilized cells are washed 4 times with distilled water. After cell lysis with a 0.3 N sodium hydroxide solution, the radioactivity in the lysate is measured with a liquid scintillation counter. Effects of a compound that alters the binding of the polypeptide of the present invention to the protein of the present invention can be determined by comparing with an increase of the radioactivity by thymidine uptake when the polypeptide of the present invention alone is administered. In this case, a compound that suppresses an increase of the radioactivity by administering the polypeptide of the present invention can be selected as a candidate substance capable of altering the binding properties of the protein of the present invention and the polypeptide of the present invention. On the other hand, an agonist can be screened by monitoring an increase of the radioactivity in the same way as in the polypeptide of the present invention when the test compound alone is administered.

(9) When the polypeptide of the present invention is added to the cells in which the protein of the present invention is expressed, K channel is activated so that $K^+$ ions present within the cells are effluxed extracellularly. Since $Rb^+$ ions in the related elements to $K^+$ ions flow out of the cells through the K channel without being distinguished from $K^+$ ions, labeled Rb ($[^{86}Rb]$) is added to the cells to permit intracellular uptake of the isotope. Then, the efflux of $[^{86}Rb]$ that flows out by stimulation of the polypeptide A of the present invention is measured to assay the action of the polypeptide A of the present invention. The method for screening the compound that alters the binding of the polypeptide of the present invention to the protein of the present invention utilizing the $[^{86}Rb]$ efflux activity is specifically described below.

Two days after inoculation on 24 wells, the cells in which the protein of the present invention is expressed are kept warm for 2 hours in a medium supplemented with 1 mCi/ml of $^{86}RbCl$. The medium is thoroughly washed to completely remove $^{86}RbCl$ in the outer liquid. The polypeptide of the present invention or the polypeptide of the present invention and a test compound is/are added to the cells. The outer liquid is recovered 30 minutes later and the radioactivity is counted with a γ counter. Effects of a compound that alters the binding of the polypeptide of the present invention to the protein of the present invention can be assayed by comparing an increase of the radioactivity by $[^{86}Rb]$ efflux with the case when the polypeptide of the present invention alone is administered. In this case, a compound that suppresses an increase of the radioactivity by administration of the polypeptide of the present invention can be selected as a candidate substance capable of altering the binding properties of the protein of the present invention and the polypeptide of the present invention. On the other hand, an agonist can be screened as well by monitoring an increase of the radioactivity in the same way as in the polypeptide of the present invention when the test compound alone is administered.

(10) The activity of the polypeptide of the present invention can be assayed by measuring extracellular pH (acidification rate) which changes in the cells in which the protein of the present invention is expressed, in response to the polypeptide of the present invention, using a Cytosensor device (Molecular Device Co.). The method for screening a compound that alters the binding of the polypeptide of the present invention to the protein of the present invention through the extracellular pH measurement using the Cytosensor device is specifically described below.

The cells where the protein of the present invention is expressed are cultured overnight in a capsule for the Cytosensor device, which is set in a chamber of the device to reflux 0.1% BSA-containing RPMI 1640 medium (manufactured by Molecular Device) for about 2 hours until the extracellular pH becomes stable. After the pH becomes stable, the medium containing the polypeptide of the present invention or the polypeptide of the present invention and a test compound is refluxed onto the cells. The pH changes in the medium caused by the reflux are assayed. Effects of a compound that alters the binding of the polypeptide of the present invention to the protein of the present invention can be assayed by comparing changes of extracellular pH in the cells, in which the protein of the present invention is expressed, with the case when the polypeptide of the present invention is administered solely. In this case, a compound that suppresses changes of extracellular pH by administering the polypeptide of the present invention can be selected as a candidate substance capable of altering the binding properties of the protein of the present invention and the polypeptide of the present invention. On the other hand, an agonist can be screened as well by monitoring changes of extracellular pH in the same way as in the polypeptide of the present invention when the test compound alone is administered.

(11) In *Saccharomyces Cerevisiae*, sex pheromone receptor STe2 of haploid α-mating type (MATα) is coupled to G protein Gpa1 to activate MAP kinase in response to sex pheromone α-mating factor, whereby Far1 (cell-cycle arrest) and transcription activator Ste12 are activated. Ste12 induces the expression of a wide variety of proteins, including FUS1 which is associated with mating. On the other hand, regulator Sst2 functions to inhibit the foregoing process. In this system, an attempt has been made to construct an assay system for the reaction of an agonist with the protein of the present invention, which involves preparing a yeast transfected with a gene encoding the protein of the present invention, activating the intracellular signal transduction system in the yeast by agonist stimulation to the protein of the present invention and using the resulting growth, etc. as an indicator (Pausch, M. H., Trends in Biotechnology, 15, 487-494, 1997). Utilizing this system yeast transfected with the gene encoding the protein of the present invention, the compound that alters the binding properties of the polypeptide of the present invention and the protein of the present invention can be screened.

Ste2 in MATα yeast and a gene encoding Gpa1 are removed and instead, a gene encoding the protein of the present invention and a gene encoding Gpa1-Gai2 fused protein are introduced. A gene encoding Far is removed to cause no cell-cycle arrest and a gene encoding Sst is removed to previously increase the sensitivity in response to the polypeptide of the present invention. Furthermore, FUS1-HIS3 gene, which is FUS1 ligated with histidine biosynthesis gene HIS3, is introduced. The foregoing genetic recombinant engineering can easily be performed, e.g., by the method reported by Price, et al. (Price, L. A. et al., Molecular and Cellular Biology, 15, 6188-6195 (1995)), using a gene encoding the protein of the present invention in place of somatostatin receptor type 2 (SSTR2) gene. The thus constructed transformant yeast is responsive to the polypeptide of the present invention as a ligand to the protein of the present invention with a high sensitivity so that MAP kinase is activated and a histidine biosynthesis enzyme is synthesized. Then, the transformant becomes capable of growing in a histidine-deficient medium. Utilizing this, a response of the yeast wherein the protein of the present invention is expressed can be monitored using growth of the yeast in a histidine-deficient medium as an indicator. The method for screening a compound that alters the binding of the polypeptide of the present invention to the protein of the present invention is described below.

The thus produced yeast as described above, in which the protein of the present invention is expressed, is incubated overnight in complete synthesis liquid medium and then added to a histidine-free, dissolved agar medium in a concentration of $2\times10^4$ cells/ml. The yeast is then plated on a square Petri dish of 9×9 cm. After the agar is solidified, a sterilized filter paper impregnated with the polypeptide of the present invention or the polypeptide of the present invention and a test compound is placed on the agar surface, followed by incubation at 30° C. for 3 days. Effects of a compound that alters the binding of the polypeptide of the present invention to the protein of the present invention can be assayed by comparing the growth of yeast around the filter paper with the case of single administration of the polypeptide of the present invention. In this case, the compound that suppresses the growth of the yeast by administration of the polypeptide of the present invention can be selected as a candidate substance capable of altering the binding properties of the protein of the present invention and the polypeptide of the present invention. On the other hand, an agonist can be screened as well by monitoring the growth of the yeast in the same way as in the polypeptide of the present invention. Furthermore, a compound that alters the binding of the polypeptide of the present invention to the protein of the present invention can also be assayed by previously adding the polypeptide of the present invention to the agar medium, impregnating a sterilized filter paper with a test compound alone, incubating and monitoring that the growth of the yeast over the entire surface of a Petri dish is affected at the periphery of the filter paper.

(12) When gene RNA encoding the protein of the present invention is injected into *Xenopus laevis* oocytes and stimulated by the polypeptide of the present invention, the intracellular $Ca^{2+}$ ion level increases to cause a calcium-activated chloride current, which can be taken as fluctuation in membrane potential (the same applies to the case where fluctuation occurs in K ion level gradient). By monitoring this reaction induced by the polypeptide of the present invention in *Xenopus laevis* oocytes where the gene encoding the protein of the present invention is transfected, a compound that alters the binding properties of the polypeptide of the present invention and the protein of the present invention can be screened.

A female *Xenopus laevis* anesthetized by immersing in ice water is anatomized to withdraw oocytes. The oocyte clusters are treated with collagenase (0.5 mg/ml) dissolved in an MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES; pH 7.4) at 19° C. for 1 to 6 hours at 150 rpm, until the oocytes are loosen. Washing is performed 3 times by replacing the outer liquid with the MBS solution followed by microinjection mRNA (50 ng/50 nl) encoding the protein of the present invention with a micromanipulator. The mRNA encoding the protein of the present invention may be prepared from tissues or cells, or may be transcribed from plasmids in vitro. The oocytes are incubated in the MBS solution at 20° C. for 3 days. The oocytes are placed in a hole of a voltage clamp device, which is continuously perfused with Ringer's solution, and impaled into the cells with glass microelectrodes for voltage clamp and glass microelectrodes for potential recording, in which (−) electrode is placed outside the oocytes. When the holding potential stabilizes, Ringer's solution containing the polypeptide of the present invention or the polypeptide of the present invention and a test compound is perfused to record changes in potential. Effects of the compound that alters the binding properties of the polypeptide of the present invention and the protein of the present invention can be determined by comparing changes in cell membrane potential of the *Xenopus laevis* oocytes wherein the gene encoding the protein of the present invention is transfected, with the case wherein Ringer's solution containing the polypeptide of the present invention alone is perfused. In this case, a compound that suppresses the changes in cell membrane potential by administration of the polypeptide of the present invention can be selected as a candidate substance capable of altering the binding properties of the protein of the present invention and the polypeptide of the present invention. On the other hand, an agonist can be screened as well by monitoring the changes in cell membrane potential in the same way as in the polypeptide of the present invention where the test compound alone is administered.

In this system, the amount of alteration may be increased by introducing poly(A)⁺ RNAs of various G protein genes so that it becomes easier to monitor the reaction. Also, the reaction can be assayed by co-injecting poly(A)⁺ RNAs to a gene for the protein such as aequorin that emits light in the presence of $Ca^{2+}$ and monitoring the light emission, not changes in membrane potential.

(Kit for Screening the Compound or its Salt that Alters the Binding Properties of the Polypeptide of the Present Invention and the Protein of the Present Invention)

The kit for screening the compound or its salt that alters the binding properties of the polypeptide of the present invention and the protein of the present invention comprises the protein of the present invention, a cell containing the protein of the present invention, or a membrane fraction of the cell containing the protein of the present invention, and the polypeptide of the present invention.

Examples of the screening kit of the present invention include the following.

1. Reagent for screening (a) Assay buffer and wash buffer

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(b) Standard Preparation of the Protein of the Present Invention

CHO cells in which the protein of the present invention is expressed are subcultured in a 12-well plate at the rate of $5\times10^5$ cells/well and then cultured at 37° C. under 5% $CO_2$ and 95% air for 2 days.

(c) Labeled Ligand

The polypeptide of the present invention labeled with commercially available [$^3$H], [$^{121}$I], [$^{14}$C], [$^{35}$S], etc.

The labeled peptide is dissolved in a suitable solvent or buffer, and the solution is stored at 4° C. or −20° C., which is diluted to 1 μM with an assay buffer at use.

(d) Standard Ligand Solution

The polypeptide of the present invention is dissolved in PBS supplemented with 0.1% bovine serum albumin (manufactured by Sigma) in a concentration of 1 mM, and the solution is stored at −20° C.

2. Assay Method (a) Cells are cultured in a 12-well tissue culture plate to express the protein of the present invention. After washing the cells twice with 1 ml of the assay buffer, 490 μl of the assay buffer is added to each well.

(b) After 5 μl of a test compound solution of $10^{-3}$ to $10^{-10}$ M is added, 5 μl of a labeled form of the polypeptide of the present invention is added to the system followed by reacting at room temperature for an hour. To determine the amount of the non-specific binding, the polypeptide of the present invention of $10^{-3}$ M is added in an amount of 5 μl, instead of the test compound.

(c) The reaction mixture is removed and washed 3 times with 1 ml each of the wash buffer. The labeled polypeptide of the present invention bound to the cells is dissolved in 0.2N NaOH-1% SDS and mixed with 4 ml of a liquid scintillator A (manufactured by Wako Pure Chemical Industries, Ltd.).

(d) Radioactivity is measured using a liquid scintillation counter (manufactured by Beckmann) and PMB (percent of the maximum binding) is calculated in accordance with the following equation:

Formula:

$$PMB=[(B-NSB)/(B_0-NSB)]\times 100$$

wherein:

PMB: percent of the maximum binding
B: value when a sample is added
NSB: non-specific binding
$B_0$: maximum binding The compound or its salt, which is obtained by the screening method or the screening kit of the present invention, is a compound that alters the binding properties of the polypeptide of the present invention and the protein of the present invention (that inhibits or promotes the binding). Specifically, these compounds are compounds that exhibit the cell stimulating activity mediated by the protein of the present invention (so-called agonists), or compounds that do not exhibit the cell stimulating activity (so-called antagonists). Examples of such compounds include peptides, proteins, non-peptide compounds, synthetic compounds, fermentation products, and the like. These compounds may be novel compounds or publicly known compounds.

In order to assess whether the compound is either an agonist or an antagonist, to the protein of the present invention described above, a specific method for the assessment may be performed in accordance with (i) or (ii) below.

(i) According to the screening methods (1) to (3) described above, the binding assay is carried out to obtain the compound that alters the binding properties of the polypeptide of the present invention and the protein of the present invention (especially, the compound that inhibits the binding). It is then determined if the compound has the above cell-stimulating activity mediated by the protein of the present invention. The compound or its salt having the cell-stimulating activity is an agonist to the protein of the present invention, whereas the compound or its salt having no such an activity is an antagonist to the protein of the present invention.

(ii) (a) A test compound is brought in contact with a cell containing the protein of the present invention and the cell stimulating activity mediated by the protein of the present invention. The compound or its salt having the cell stimulating activity is an agonist.

(b) The cell stimulating activity mediated by the protein of the present invention is assayed in the case where a compound that activates the protein of the present invention (e.g., the polypeptide of the present invention or an agonist to the protein of the present invention, etc.) is brought in contact with a cell containing the protein of the present invention and in the case where a compound that activates the protein of the present invention and a test compound are brought in contact with a cell containing the protein of the present invention, and comparing the properties.

The compound or its salt capable of reducing the cell stimulating activity mediated by the compound that activates the protein of the present invention is an antagonist.

The agonist has the same action as the physiological activity possessed by the polypeptide of the present invention, and is useful as a safe and low-toxic medicament in the same way as in the polypeptide of the present invention.

Conversely, the antagonist can suppress the physiological activity possessed by the polypeptide of the present invention, and is useful as a safe and low-toxic medicament that suppresses the receptor activity.

[2] Medicament Comprising the Polypeptide, etc. of the Present Invention

The polypeptide A1 of the present invention possesses, e.g., a digestive tract contractile activity, smooth muscle contractile activity, hypertensive activity, food intake suppressing activity, prolactin release suppressing activity, etc. and is associated with the phase advances and delays of circadian rhythms. Thus, the polypeptide A1 of the present invention, the polynucleotide encoding the polypeptide A1 of the present invention and the compound or its salt that promotes the activity of the polypeptide A1 of the present invention are useful as low-toxic and safe agents for preventing/treating, for example, hypotension, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, sleeping disorders [e.g., primary insomnia, circadian rhythm disorders (e.g., change in physical conditions caused by three-shift work, time zone change syndrome (jet lag), etc.)], lethargy, sterility, seasonal depression, reproductive dysfunction, endocrine diseases, senile dementia, Alzheimer's disease, various age-related disorders, cerebral circulatory disorder (e.g., apoplexy, etc.), head injury, spinal cord injury, epilepsy, anxiety, depression, manic-depressive disorder, schizophrenia, alcoholism, Parkinson's disease, arteriosclerosis, arrhythmia, premenstrual syndrome, glaucoma, cancer, AIDS, diabetes mellitus, etc., preferably, hypotension, obesity, lethargy, time zone change syndrome, sterility, etc. The antibody to the polypeptide A1 of the present invention and the compound or its salt that inhibits the activity of the polypeptide A1 of the present invention are useful as low-toxic and safe agents for preventing/treating, for example, hypertension, anorexia, menopausal symptoms, insomnia, immune/inflammatory disease (e.g., rheumatoid arthritis, arthritis deformans, etc.), etc., preferably hypertension, anorexia, menopausal symptoms, insomnia, etc.

The polypeptide A2 of the present invention possesses, e.g., a prolactin releasing activity, etc. Thus, the polypeptide A2 of the present invention, the polynucleotide encoding the polypeptide A2 of the present invention and the compound or its salt that promotes the activity of the polypeptide A2 of the present invention are useful as low-toxic and safe agents for preventing/treating, for example, prolactin release deficiency (e.g., ovarian hypofunction, spermatic underdevelopment, menopausal symptoms, etc.), hyperthyroidism, etc., preferably menopausal symptoms, hyperthyroidism, etc. The antibody to the polypeptide A2 of the present invention and the compound or its salt that inhibits the activity of the polypeptide A2 of the present invention are useful as low-toxic and safe agents for preventing/treating, for example, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, hypothyroidism, etc., preferably sterility, hypothyroidism, etc.; (preferably, as a prolactin production suppressing agent).

The polypeptide B of the present invention has a prolactin releasing activity, etc. Thus, the polypeptide B of the present invention, the polynucleotide encoding the polypeptide B of the present invention and the compound or its salt that promotes the activity of the polypeptide B of the present invention are useful as low-toxic and safe agents for preventing/treating, for example, prolactin release deficiency (e.g., ovarian hypofunction, spermatic underdevelopment, menopausal symptoms, etc.), hyperthyroidism, etc., preferably menopausal symptoms, hyperthyroidism, etc. The antibody to the polypeptide B of the present invention and the compound or its salt that inhibits the activity of the polypeptide B of the present invention are useful as low-toxic and safe agents for preventing/treating, for example, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, hypothyroidism, etc., preferably sterility, hypothyroidism, etc.; (preferably, as a prolactin production suppressing agent).

The agonist to the protein of the present invention can be used, for example, as an agent for preventing/treating hypotension; a local vasoconstrictor; a uterine contraction stimulant; an agent for ameliorating and preventing/treating various diseases associated with uterine contractile dysfunction including uterine inertia, atonic bleeding, pre- and post-expulsion of placenta, subinvolution of uterus, induced abortion, induction of delivery, arrest of labor, incompetent cervical as, inversion of the uterus, retained placenta and retained egg membranes, postpartum hemorrhage, female genital prolapse, sterility, maternal care during multiple pregnancy, malpresentation, dysmenorrhea, miscarriage, endometriosis, chronic inflammatory disease of uterus, uterine myoma, uterine abnormalities, uterine adenomyosis, uterocervical laceration, posttraumatic stress disorder, etc. The antagonist of the protein of the present invention is useful as an agent for preventing/treating hypertension, myocardial infarction, acute renal failure, stress-related disorders [e.g., (1) cardiovascular disorders (e.g., angina pectoris, myocardial infarction, arrhythmia, etc.), (2) respiratory disorders (e.g., bronchial asthma, hyperventilation syndrome, etc.), (3) musculoskeletal disorders (e.g., rheumatoid arthritis, lumbago, migraine, tension headache, etc.), (4) diabetes mellitus, menopausal symptoms, hyperthyroidism, chronic pain, immune suppression, alimentary disorders (e.g., gastric ulcer, ulcerative colitis, etc.)], etc.; a uterine contraction suppressing agent; an agent for ameliorating and preventing/treating various disorders associated with excessive uterine contractions, including hypertonic labor, false contractions, prolonged pregnancy, tonic uterine contractions, fetal distress, uterine rupture, cervical laceration, preterm delivery, uterine myoma, uterine abnormalities, uterine adenomyosis, abnormalities in expulsive force, chronic inflammatory disease of uterus, maternal care during multiple pregnancy, malpresentation, Prader-Willi syndrome, dysmenorrhea, etc.

As salts of the polypeptide of the present invention, the compound that promotes or inhibits the activity of the polypeptide of the present invention, the compound obtainable using the screening method or screening kit described above, or the like, for example, pharmaceutically acceptable salts are used. Examples include salts with inorganic bases, salts with organic bases, salts with inorganic acids, salts with organic salts, salts with basic or acidic amino acids, etc.

Preferred examples of the salts with inorganic bases include alkali metal salts such as sodium salts, potassium salts, etc.; alkaline earth metal salts such as calcium salts, magnesium salts, etc.; aluminum salts, ammonium salts, and the like.

Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc.

Preferred examples of the salts with inorganic acids include salts with hydrochloric acid, hydrobromic acid, sulfuric acid, phosphoric acid, etc.

Preferred examples of the salts with organic acids include salts with formic acid, acetic acid, propionic acid, fumaric acid, oxalic acid, tartaric acid, maleic acid, citric acid, succinic acid, malic acid, methanesulfonic acid, benzenesulfonic acid, benzoic acid, etc.

Suitable examples of the salts with basic amino acids include salts with arginine, lysine, ornithine, etc. Preferred examples of the salts with acidic amino acids include salts with aspartic acid, glutamic acid, etc.

When the polypeptide of the present invention, the polynucleotide encoding the polypeptide of the present invention, the compound that promotes or inhibits the polypeptide of the present invention, the antibody to the polypeptide of the present invention, the compound or its salts obtainable using the screening method or screening kit of the present invention are used as the medicaments described above, they can be formulated in a conventional manner. For example, they can be administered orally as tablets coated with sugar or with enteric coating if necessary, capsules, elixirs, microcapsules, etc., or parenterally in the form of injections such as sterile solutions or suspensions in water or in pharmaceutically acceptable solutions other than water. For example, the compound or its salts can be mixed with carriers, flavoring agents, excipients, vehicles, preservatives, stabilizers, binders, etc. in a unit dosage form required for generally accepted pharmaceutical practice to prepare pharmaceutical preparations. The amount of active ingredients in these preparations is adjusted so as to obtain appropriate doses within specified ranges.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of a capsule, liquid carriers such as oils and fats may further be used together with the additives described above. A sterile composition for injection may be formulated in a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol, etc.), a polyalcohol (e.g., propylene glycol, polyethylene glycol, etc.), a nonionic surfactant (e.g., polysorbate 80™, HCO-50, etc.), or the like. Examples of the oily medium include sesame oil, soybean oil, etc., which may also be used in combination with a dissolution aid such as benzyl benzoate, benzyl alcohol, etc.

These preparations may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and thus can be administered to warm-blooded mammal (e.g., human, guinea pig, rat, mouse, swine, sheep, bovine, monkey, dog or fowl), etc.

The dose of the compound or its salt that promotes the activity of the polypeptide A1 of the present invention may vary depending upon conditions, etc. For example, when the compound or its salt is orally administered, it is administered to the patient (as 60 kg body weight) with hypotension generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the patient (as 60 kg body weight) with hypotension in the form of, e.g., an injectable preparation, it is generally advantageous to administer the compound or its salt in a single dose of about 0.01 to about 30 mg, preferably about 0.1 to about 20 mg and more preferably about 0.1 to about 10 mg per day. For other animal species, the corresponding dose as converted per 60 kg weight can be administered.

The dose of the compound or its salt that promotes the activity of the polypeptide A2 of the present invention may vary depending upon conditions, etc. For example, when the compound or its salt is orally administered, it is administered to the patient (as 60 kg body weight) with menopausal symptoms generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the patient (as 60 kg body weight) with menopausal symptoms in the form of, e.g., an injectable preparation, it is generally advantageous to administer the compound or its salt in a single dose of about 0.01 to about 30 mg, preferably about 0.1 to about 20 mg and more preferably about 0.1 to about 10 mg per day. For other animal species, the corresponding dose as converted per 60 kg weight can be administered.

The dose of the compound or its salt that promotes the activity of the polypeptide B of the present invention may vary depending upon conditions, etc. For example, when the compound or its salt is orally administered, it is administered to the patient (as 60 kg body weight) with menopausal symptoms generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the patient (as 60 kg body weight) with menopausal symptoms in the form of, e.g., an injectable preparation, it is generally advantageous to administer the compound or its salt in a single dose of about 0.01 to about 30 mg, preferably about 0.1 to about 20 mg and more preferably about 0.1 to about 10 mg per day. For other animal species, the corresponding dose as converted per 60 kg weight can be administered.

The dose of the compound or its salt that inhibits the activity of the polypeptide A1 of the present invention may vary depending upon conditions, etc. For example, when the compound or its salt is orally administered, it is administered to the patient (as 60 kg body weight) with hypertension generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the patient (as 60 kg body weight) with hypertension in the form of, e.g., an injectable preparation, it is generally advantageous to administer in a single dose of about 0.01 to about 30 mg, preferably about 0.1 to about 20 mg and more preferably about 0.1 to about 10 mg per day. For other animal species, the corresponding dose as converted per 60 kg weight can be administered.

The dose of the compound or its salt that inhibits the activity of the polypeptide A2 of the present invention may vary depending upon conditions, etc. For example, when the compound or its salt is orally administered, it is administered to the patient (as 60 kg body weight) with sterility generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the patient (as 60 kg body weight) with sterility in the form of, e.g., an injectable preparation, it is generally advantageous to administer in a single dose of about 0.01 to about 30 mg, preferably about 0.1 to about 20 mg and more preferably about 0.1 to about 10 mg per day. For other animal species, the corresponding dose as converted per 60 kg weight can be administered.

The dose of the compound or its salt that inhibits the activity of the polypeptide B of the present invention may vary depending upon conditions, etc. For example, when the compound or its salt is orally administered, it is administered to the patient (as 60 kg body weight) with sterility generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the patient (as 60 kg body weight) with sterility in the form of, e.g., an injectable preparation, it is generally advantageous to administer in a single dose of about 0.01 to about 30 mg, preferably about 0.1 to about 20 mg and more preferably about 0.1 to about 10 mg per day. For other animal species, the corresponding dose as converted per 60 kg weight can be administered.

The dose of the compound (especially the antagonist) or its salt, which is obtained by using the screening method or screening kit of the present invention, may vary depending upon conditions, etc. For example, when the compound or its salt is orally administered, it is administered to the adult patient (as 60 kg body weight) with hypertension generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the adult patient (as 60 kg body weight) with hypertension in the form of, e.g., an injectable preparation, it is advantageous to administer the compound or its salt in a single dose of about 0.01 to about 30 mg, preferably about 0.1 to about 20 mg and more preferably about 0.1 to about 10 mg per day. For other animal species, the corresponding dose as converted per 60 kg weight can be administered.

Hereinafter, the medicament comprising the polypeptide of the present invention, the medicament comprising the polynucleotide encoding the polypeptide of the present invention and the medicament comprising the antibody to the polypeptide of the present invention are described more specifically.

(Medicament Comprising the Polypeptide of the Present Invention)

The polypeptide A1 of the present invention possesses, e.g., a digestive tract contractile activity, smooth muscle contractile activity, hypertensive activity, food intake suppressing activity, prolactin release suppressing activity, etc. and is associated with the phase advances and delays of circadian rhythms. Thus, the polypeptide A1 of the present invention is useful as low-toxic and safe agents for preventing/treating, for example, hypotension, obesity (e.g., malignant mastocytosis, exogenous obesity, hyperinsulinemic obesity, hyperplasmic obesity, hypophyseal obesity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), lethargy, time zone change syndrome, sterility, etc.

The polypeptide A2 of the present invention possesses, e.g., a prolactin releasing activity, etc. and is useful as a low-toxic and safe agent for preventing/treating menopausal symptoms, hyperthyroidism, etc.

The polypeptide B of the present invention possesses, e.g., a prolactin releasing activity, etc. and is useful as a low-toxic and safe agent for preventing/treating menopausal symptoms, hyperthyroidism, etc.

The salts of the polypeptide of the present invention include the salts described above and those described above are preferred.

When the polypeptide of the present invention is used in the preventive/therapeutic agent described above, the polypeptide is advantageously used on a purity level of at least 90%, preferably at least 95%, more preferably at least 98% and most preferably at least 99%.

When the polypeptide of the present invention is used as the aforesaid medicament (preventive/therapeutic agent, etc.), the polypeptide can be prepared into pharmaceutical preparations by publicly known methods, including the methods described above.

The polypeptide of the present invention can be administered orally, for example, in the form of tablets which may be sugar coated, if necessary, capsules, elixirs, microcapsules etc., or parenterally in the form of injections such as sterile solutions or suspensions in water or in pharmaceutically acceptable solutions other than water. For example, the polypeptide of the present invention can be mixed with carriers, flavoring agents, excipients, vehicles, preservatives, stabilizers, binders, etc. in a unit dosage form generally accepted. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, a flavoring agent such as peppermint, akamono oil and cherry, etc. When the unit dosage is in the form of a capsule, liquid carriers such as oils and fats may further be used together with the additives described above. A sterile composition for injection may be formulated in a conventional manner used to make pharmaceutical preparations, e.g., by dissolving or suspending the active ingredients in a vehicle such as water for injection with a naturally occurring vegetable oil such as sesame oil and coconut oil, etc. to prepare the pharmaceutical preparations.

Examples of an aqueous medium for injection include physiological saline and an isotonic solution containing glucose and other auxiliary agents (e.g., D-sorbitol, D-mannitol, sodium chloride, etc.), or the like and may be used in combination with an appropriate dissolution aid such as an alcohol (e.g., ethanol, etc.), a polyalcohol (e.g., propylene glycol and polyethylene glycol, etc.), a nonionic surfactant (e.g., polysorbate 80™, HCO-50, etc.), or the like. Examples of the oily medium include sesame oil, soybean oil, etc., which may also be used in combination with a dissolution aid such as benzyl benzoate, benzyl alcohol, etc. The polypeptide may further be formulated together with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the pharmaceutical preparation thus obtained is safe and low toxic, it can be administered to human or other warm-blooded mammal (e.g., mouse, rat, rabbit, sheep, swine, bovine, horse, fowl, cat, dog, monkey, chimpanzee, etc.).

The dose of the polypeptide A1 of the present invention may vary depending upon conditions, etc. For example, when the polypeptide A1 is orally administered, it is administered to the patient (as 60 kg body weight) with hypotension generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. In general, when it is administered to the patient (as 60 kg body weight) with hypotension in the form of, e.g., an injectable preparation, a single dose of about 0.01 to about 30 mg, preferably about 0.1 to about 20 mg and more preferably about 0.1 to about 10 mg is advantageously administered per day. For other animal species, the corresponding dose as converted per 60 kg weight can be administered.

The dose of the polypeptide A2 of the present invention may vary depending upon conditions, etc. For example, when the polypeptide A2 is orally administered, it is administered to the patient (as 60 kg body weight) with menopausal symptoms generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the patient (as 60 kg body weight) with menopausal symptoms in the form of, e.g., an injectable preparation, it is generally advantageous to administer the polypeptide A2 in a single dose of about 0.01 to about 30 mg, preferably about 0.1 to about 20 mg and more preferably about 0.1 to about 10 mg per day. For other animal species, the corresponding dose as converted per 60 kg weight can be administered.

The dose of the polypeptide B of the present invention may vary depending upon conditions, etc. For example, when the polypeptide B is orally administered, it is administered to the patient (as 60 kg body weight) with menopausal symptoms generally in a dose of about 0.1 to 1000 mg, preferably about 1.0 to 300 mg and more preferably about 3.0 to 50 mg. In parenteral administration, its single dose may vary depending upon subject to be administered, conditions, route of administration, etc. When it is administered to the patient (as 60 kg body weight) with menopausal symptoms in the form of, e.g., an injectable preparation, it is generally advantageous to administer the polypeptide B in a single dose of about 0.01 to about 30 mg, preferably about 0.1 to about 20 mg and more preferably about 0.1 to about 10 mg per day. For other animal species, the corresponding dose as converted per 60 kg weight can be administered.

(Medicament Comprising the Polynucleotide Encoding the Polypeptide of the Present Invention)

The polypeptide A1 of the present invention possesses, e.g., a digestive tract contractile activity, smooth muscle contractile activity, hypertensive activity, food intake suppressing activity, prolactin release suppressing activity, etc. and is associated with the phase advances and delays of circadian rhythms. Thus, the polynucleotide encoding the polypeptide A1 of the present invention is useful as a low-toxic and safe agent for preventing/treating, for example, hypotension, obesity, lethargy, time zone change syndrome, sterility, etc.

The polypeptide A2 of the present invention possesses, e.g., a prolactin releasing activity, etc. Thus, the polynucleotide encoding the polypeptide A2 of the present invention is useful as a low-toxic and safe agent for preventing/treating menopausal symptoms, hyperthyroidism, etc.

The polypeptide B of the present invention possesses, e.g., a prolactin releasing activity, etc. Thus, the polynucleotide encoding the polypeptide B of the present invention is useful as a low-toxic and safe agent for preventing/treating menopausal symptoms, hyperthyroidism, etc.

When a patient has a reduced level of, or deficient in the polypeptide of the present invention in his or her body, the polynucleotide of the present invention can serve to fulfill the role of the polypeptide of the present invention sufficiently or properly for the patient, (i) by administering the polynucleotide of the present invention to the patient to express the polypeptide of the present invention in the body, or (ii) by inserting the polynucleotide of the present invention into a cell, expressing the polypeptide of the present invention and then transplanting the cell to the patient, or the like.

Where the polynucleotide of the present invention is used as the preventive/therapeutic agent described above, the polynucleotide can be prepared into pharmaceutical preparations by publicly known methods, including the methods described above, which are provided for administration.

For instance, the polynucleotide may be administered alone; or after the polynucleotide is inserted into an appropriate vector such as retrovirus vector, adenovirus vector, adenovirus-associated virus vector, etc., the product can be administered to human or other warm-blooded animal in a conventional manner. The polynucleotide of the present invention may also be administered as it is, or with adjuvants to assist its uptake by gene gun or through a catheter such as a catheter with a hydrogel. In addition, a vector inserted with the polynucleotide (e.g., DNA) of the present invention can be prepared into pharmaceutical preparations in the same way as in the polypeptide of the present invention described above, and the preparations can be normally used parenterally.

The pharmaceutical preparations thus obtained are safe and low-toxic and can be administered to, e.g., human or other warm-blooded animals (e.g., rats, mice, guinea pigs, rabbits, fowl, sheep, swine, bovine, horses, cats, dogs, monkeys, etc.).

The dose of the polynucleotide comprising the polynucleotide encoding the polypeptide A1 of the present invention may vary depending upon conditions, etc. but generally is about 0.1 to 100 mg per day for the patient (as 60 kg body weight) with hypotension.

The dose of the polynucleotide comprising the polynucleotide encoding the polypeptide A2 of the present invention may vary depending upon conditions, etc. but generally is about 0.1 to 100 mg per day for the patient (as 60 kg body weight) with menopausal symptoms.

The dose of the polynucleotide comprising the polynucleotide encoding the polypeptide B of the present invention may vary depending upon conditions, etc. but generally is about 0.1 to 100 mg per day for the patient (as 60 kg body weight) with menopausal symptoms.

(Medicament Comprising the Antibody to the Polypeptide of the Present Invention)

The polypeptide A1 of the present invention possesses, e.g., a digestive tract contractile activity, smooth muscle contractile activity, hypertensive activity, food intake suppressing activity, prolactin release suppressing activity, etc. and is associated with the phase advances and delays of circadian rhythms. Thus, the antibody to the polypeptide A1 of the present invention is useful as a low-toxic and safe agent for preventing/treating, e.g., hypertension, anorexia, menopausal symptoms, insomnia, etc.

The polypeptide A2 of the present invention has a prolactin releasing activity, etc. Thus, the antibody to the polypeptide A2 of the present invention is useful as a low-toxic and safe agent for preventing/treating, e.g., sterility, hypothyroidism, etc.

The polypeptide B of the present invention has a prolactin releasing activity, etc. Accordingly, the antibody to the polypeptide B of the present invention is useful as a low-toxic and safe agent for preventing/treating, e.g., sterility, hypothyroidism, etc.

Where the antibody (e.g., neutralizing antibody) of the present invention is used as the medicament described above (therapeutic/preventive agent, etc.), the antibody molecule per se may be used, or F(ab')2, Fab' or Fab fractions of the antibody molecule may be used as well.

The agent for preventing/treating the diseases described above, which comprises the antibody of the present invention can be administered orally or parenterally (e.g., intravascularly, subcutaneously, etc.) to human or other mammal (e.g., rat, rabbit, sheep, swine, bovine, cat, dog, monkey, etc.) directly as liquid or in the form of an appropriate pharmaceutical composition. Preferably, the agent can be administered in the form of vaccine in a conventional manner.

The antibody of the present invention may be administered directly as it is or in the form of an appropriate pharmaceutical composition. The pharmaceutical composition can be prepared by publicly known methods, including the method described above. For example, the pharmaceutical composition used for administration may contain the antibody of the present invention or salts thereof, and a pharmacologically acceptable carrier, diluent or excipient. Such a pharmaceutical composition is provided in the dosage form suitable for oral or parenteral administration.

Specifically, the composition for oral administration includes solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and may contain a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration used are injections, suppositories, etc. and the injections may include the dosage form of intravenous, subcutaneous, transcutaneous, intramuscular and drip injections, etc. Such injections are prepared by publicly known methods, e.g., by dissolving, suspending or emulsifying the aforesaid antibody of the present invention or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol or polyethylene glycol), nonionic surfactant [e.g., polysorbate 80, HCO-50 (polyoxyethylene (50 mol) adduct of hydrogenated castor oil)] may be used in combination. For the oily solution, for example, sesame oil, soybean oil and the like are used, and dissolution aids such as benzyl benzoate, benzyl alcohol, etc. may be used in combination. The thus-prepared liquid for injection is normally filled in an appropriate ampoule. The suppository used for rectal administration may be prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

The dose of the antibody to the polypeptide A1 of the present invention varies depending on subject to be administered, target disease, conditions, route for administration, etc.; when it is used for the treatment/prevention of the patient with, e.g., hypertension, the antibody of the present invention is advantageously administered to the patient through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For other parenteral administration and oral administration, the corresponding dose may be administered. When the conditions are extremely serious, the dose may be increased depending on the conditions.

The dose of the antibody to the polypeptide A2 of the present invention varies depending on subject to be administered, target disease, conditions, route for administration, etc.; when it is used for the treatment/prevention of the patient with, e.g., sterility, the antibody of the present invention is advantageously administered to the patient through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For other parenteral administration and oral administration, the corresponding dose may be administered. When the conditions are extremely serious, the dose may be increased depending on the conditions.

The dose of the antibody to the polypeptide B of the present invention varies depending on subject to be administered, target disease, conditions, route for administration, etc.; when it is used for the treatment/prevention of the patient with, e.g., sterility, the antibody of the present invention is advantageously administered to the patient through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to S times, preferably approximately 1 to 3 times, per day. For other parenteral administration and oral administration, the corresponding dose may be administered. When the conditions are extremely serious, the dose may be increased depending on the conditions.

[3] Diagnostic Agent Using the Antibody of the Present Invention

As described above, the polypeptide of the present invention can be quantified with high sensitivity by using the antibody of the present invention. Thus, various diseases associated with the polypeptide of the present invention can be diagnosed using the antibody of the present invention.

Specifically, the polypeptide A1 of the present invention has, for example, a digestive tract contractile activity, smooth muscle contractile activity, hypertensive activity, food intake suppressing activity, prolactin release suppressing activity, etc. and is associated with the phase advances and delays of circadian rhythms. Accordingly, when an increased level of the polypeptide A1 of the present invention is detected using the antibody of the present invention, it can be diagnosed that one suffers from disease, for example, hypertension, anorexia, menopausal symptoms, insomnia, immune/inflammatory disease (e.g., rheumatoid arthritis, arthritis deformans, etc.), etc.; or it is highly likely for one to suffer from these diseases in the future. Also, when a reduced level of the polypeptide A1 of the present invention is detected, it can be diagnosed that one suffers from disease such as hypotension, obesity (e.g., malignant mastocytosis, exogenous obesity, hyperinsulinemic obesity, hyperplasmic obesity, hypophyseal obesity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, sleeping disorders [e.g., primary insomnia, circadian rhythm disorders (e.g., change in physical conditions caused by three-shift work, time zone change syndrome (jet lag), etc.)], lethargy, sterility, seasonal depression, reproductive dysfunction, endocrine diseases, senile dementia, Alzheimer's disease, various age-related disorders, cerebral circulatory disorder (e.g., apoplexy, etc.), head injury, spinal cord injury, epilepsy, anxiety, depression, manic-depressive disorder, schizophrenia, alcoholism, Parkinson's disease, arteriosclerosis, arrhythmia, premenstral syndrome, glaucoma, cancer, AIDS, diabetes mellitus, etc.; or it is highly likely for one to suffer from these diseases in the future.

The polypeptide A2 of the present invention has a prolactin releasing activity, etc. Accordingly, when an increased level of the polypeptide A2 of the present invention is detected using the antibody of the present invention, it can be diagnosed that one suffers from disease, for example, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, hypothyroidism, etc.; or it is highly likely for one to suffer from these diseases in the future. Also, when a reduced level of the polypeptide A2 of the present invention is detected, it can be diagnosed that one suffers from disease, for example, prolactin release deficiency (e.g., ovarian hypofunction, spermatic underdevelopment, menopausal symptoms, etc.), hyperthyroidism, etc.; or it is highly likely for one to suffer from these diseases in the future.

The polypeptide B of the present invention has a prolactin releasing activity, etc. Accordingly, when an increased level of the polypeptide B of the present invention is detected using the antibody of the present invention, it can be diagnosed that one suffers from disease, for example, pituitary tumor, diencephalon tumor, menstrual disorder, autoimmune disease, prolactinoma, sterility, impotence, amenorrhea, lactorrhea, hyperpituitarism, Chiari-Frommel syndrome, Argonz-del Castillo syndrome, Forbes-Albright syndrome, lymphoma, Sheehan's syndrome, spermatogenesis disorder, hypothyroidism, etc.; or it is highly likely for one to suffer from these diseases in the future. Also, when a reduced level of the polypeptide B of the present invention is detected, it can be diagnosed that one suffers from disease, for example, prolactin release deficiency (e.g., ovarian hypofunction, spermatic underdevelopment, menopausal symptoms, etc.), hyperthyroidism, etc.; or it is highly likely for one to suffer from these diseases in the future.

[4] Gene Diagnostic Agent

By using the polynucleotide (DNA) of the present invention, e.g., as a probe, an abnormality (gene abnormality) of the DNA or mRNA encoding the polypeptide of the present invention in human or other warm-blooded animal (e.g., rat, mouse, guinea pig, rabbit, fowl, sheep, swine, bovine, horse, cat, dog, monkey, etc.) can be detected. Therefore, the polynucleotide is useful as a gene diagnostic agent for damages to the DNA or mRNA, its mutation or decreased expression, or increased expression or overexpression of the DNA or mRNA.

The gene diagnosis described above using the DNA of the present invention can be performed by, for example, publicly known Northern hybridization or PCR-SSCP assay (Genomics, 5, 874-879 (1989); Proceedings of the National Academy of Sciences of the United States of America, 86, 2766-2770 (1989)), DNA microarray, etc.

The polypeptide A1 of the present invention possesses, e.g., a digestive tract contractile activity, smooth muscle contractile activity, hypertensive activity, food intake suppressing activity, prolactin release suppressing activity, etc. and is associated with the phase advances and delays of circadian rhythms. Thus, when overexpression of a gene for the polypeptide A1 is detected, it can be diagnosed that one suffers from disease, for example, hypertension, anorexia, menopausal symptoms, insomnia, immune/inflammatory disease (e.g., rheumatoid arthritis, arthritis deformans, etc.), etc., or it is highly likely that one would suffer from these diseases in the future. Also, when a reduced expression of the gene for the polypeptide A1 of the present invention is detected, it can be diagnosed that one suffers from disease, for example, hypotension, obesity (e.g., malignant mastocytosis, exogenous obesity, hyperinsulinemic obesity, hyperplasmic obesity, hypophyseal obesity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, sleeping disorders [e.g., primary insomnia, circadian rhythm disorders (e.g., change in physical conditions caused by three-shift work, time zone change syndrome (jet lag), etc.)], lethargy, sterility, seasonal depression, reproductive dysfunction, endocrine diseases, senile dementia, Alzheimer's disease, various age-related disorders, cerebral circulatory disorder (e.g., apoplexy, etc.), head injury, spinal cord injury, epilepsy, anxiety, depression, manic-depressive disorder, schizophrenia, alcoholism, Parkinson's disease, arteriosclerosis, arrhythmia, premenstral syndrome, glaucoma, cancer, AIDS, diabetes mellitus, etc.; or it is highly likely that one would suffer from these diseases in the future.

The polypeptide A2 of the present invention has a prolactin releasing activity, etc. Thus, when overexpression of a gene for the polypeptide A2 is detected, it can be diagnosed that one suffers from disease, for example, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, hypothyroidism, etc.; or it is highly likely that one would suffer from these diseases in the future. Also, when a reduced expression of the gene for the polypeptide A2 of the present invention is detected, it can be diagnosed that one suffers from disease, for example, prolactin release deficiency (e.g., ovarian hypofunction, spermatic underdevelopment, menopausal symptoms, etc.), hyperthyroidism, etc.; or it is highly likely that one would suffer from these diseases in the future.

The polypeptide B of the present invention has a prolactin releasing activity, etc. Thus, when overexpression of a gene for the polypeptide B is detected, it can be diagnosed that one suffers from disease, for example, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, hypothyroidism, etc.; or it is highly likely that one would suffer from these diseases in the future. Also, when a reduced expression of the gene for the polypeptide B of the present invention is detected, it can be diagnosed that one suffers from disease, for example, prolactin release deficiency (e.g., ovarian hypofunction, spermatic underdevelopment, menopausal symptoms, etc.), hyperthyroidism, etc.; or it is highly likely that one would suffer from these diseases in the future.

[5] Medicament and Diagnostic Agent Comprising the Antisense Polynucleotide

The antisense polynucleotide of the present invention which can bind complementarily to the DNA (hereinafter referred to as "DNA(A1) of the present invention") encoding the polypeptide A1 of the present invention or the protein of the present invention to suppress the expression of the DNA is low-toxic and can suppress the function of the polypeptide A1 of the present invention or DNA(A1) of the present invention in vivo. Thus, the antisense polynucleotide can be used as an agent for ameliorating and preventing/treating diseases, for example, hypertension, myocardial infarction, acute renal failure, stress-related disorders [e.g., (1) cardiovascular disorders (e.g., angina pectoris, myocardial infarction, arrhythmia, etc.), (2) respiratory disorders (e.g., bronchial asthma, hyperventilation syndrome, etc.), (3) musculoskeletal disorders (e.g., rheumatoid arthritis, lumbago, migraine, tension headache, etc.), (4) diabetes mellitus, menopausal symptoms, chronic pain, immune suppression, alimentary disorders (e.g., gastric ulcer, ulcerative colitis, etc.)], etc.; a uterine contraction suppressing agent; an agent for preventing/treating various disorders associated with excessive uterine contractions, including hypertonic labor, false contractions, prolonged pregnancy, tonic uterine contractions, fetal distress, uterine rupture, cervical laceration, preterm delivery, uterine myoma, uterine abnormalities, uterine adenomyosis, abnormalities in expulsive force, chronic inflammatory disease of uterus, maternal care during multiple pregnancy, malpresentation, Prader-Willi syndrome, dysmenorrhea, etc.; an eating (appetite) stimulant; anorexia; insomnia; immune/inflammatory disease (e.g., rheumatoid arthritis, arthritis deformans, etc., preferably, as an agent for preventing/treating hypertension, anorexia, menopausal symptoms, insomnia, immune/inflammatory disease, etc., and more preferably, hypertension, anorexia, menopausal symptoms, insomnia, etc.

The antisense polynucleotide of the present invention which can bind complementarily to the DNA (hereinafter referred to as "DNA(A2) of the present invention") encoding the polypeptide A2 of the present invention to suppress the expression of the DNA is low-toxic and can suppress the function of the polypeptide A2 of the present invention or DNA(A2) of the present invention in vivo. Thus, the antisense polynucleotide can be used as an agent for preventing/treating, for example, sterility, hypothyroidism, etc.

The antisense polynucleotide of the present invention which can bind complementarily to the DNA (hereinafter referred to as "DNA(B) of the present invention") encoding the polypeptide B of the present invention to suppress the expression of the DNA is low-toxic and can suppress the function of the polypeptide B of the present invention or DNA(B) of the present invention in vivo. Thus, the antisense polynucleotide can be used as an agent for preventing/treating, e.g., sterility, hypothyroidism, etc.

When the antisense polynucleotide described above is used as the therapeutic/prophylactic agent described above, it can be prepared into pharmaceutical preparations by publicly known methods, which are provided for administration.

For example, when the antisense polynucleotide is used, the antisense polynucleotide may be administered alone; or after the antisense polynucleotide is inserted into an appropriate vector such as retrovirus vector, adenovirus vector, adenovirus-associated virus vector, etc., the product can be administered to human or other warm-blooded animal (e.g., rat, rabbit, sheep, swine, bovine, cat, dog, monkey, etc.) in a conventional manner. The antisense polynucleotide may also be administered as it is, or with adjuvants to assist its uptake by gene gun or through a catheter such as a catheter with a hydrogel.

A dose of the antisense polynucleotide may vary depending on target disease, subject to be administered, route for administration, etc. For example, where the antisense polynucleotide of the present invention is topically administered to the kidney for the purpose of treating hypertension, the antisense polynucleotide is generally administered to an adult (60 kg body weight) in a daily dose of about 0.1 to 100 mg.

In addition, the antisense polynucleotide may also be used as an oligonucleotide probe for diagnosis to examine the presence of the DNA of the present invention in tissues or cells and states of its expression: Diagnosis using the antisense polynucleotide can be performed in the same way as in the gene diagnostic agent described above.

(RNAi, Ribozyme)

The present invention further provides the following features:
(1) a double-stranded RNA comprising a part of RNA encoding the polypeptide A1 of the present invention;
(2) a medicament comprising the double-stranded RNA according to (1);
(3) a ribozyme comprising a part of RNA encoding the polypeptide A1 of the present invention;
(4) a medicament comprising the ribozyme according to (3);
(5) a double-stranded RNA comprising a part of RNA encoding the polypeptide A2 of the present invention;
(6) a medicament comprising the double-stranded RNA according to (5);
(7) a ribozyme comprising a part of RNA encoding the polypeptide A2 of the present invention;
(8) a medicament comprising the ribozyme according to (7);
(9) a double-stranded RNA comprising a part of RNA encoding the polypeptide B of the present invention;
(10) a medicament comprising the double-stranded RNA according to (9);
(11) a ribozyme comprising a part of RNA encoding the polypeptide B of the present invention; and,
(12) a medicament comprising the ribozyme according to (11);

These double-stranded RNAs (RNAi; RNA interference method), ribozymes, etc. can suppress the expression of the polynucleotide (e.g., DNA) of the present invention in the same way as in the antisense polynucleotide of the present invention, and can inhibit the activity or function of the polypeptide of the present invention or the polynucleotide (e.g., DNA) of the present invention.

Accordingly, the double-stranded RNA described in (1) above and the ribozyme described in (3) above can be used as an agent for preventing/treating diseases, for example, hypertension, myocardial infarction, acute renal failure, stress-related disorders [e.g., (1) cardiovascular disorders (e.g., angina pectoris, myocardial infarction, arrhythmia, etc.), (2) respiratory disorders (e.g., bronchial asthma, hyperventilation syndrome, etc.), (3) musculoskeletal disorders (e.g., rheumatoid arthritis, lumbago, migraine, tension headache, etc.), (4) diabetes mellitus, menopausal symptoms, chronic pain, immune suppression, alimentary disorders (e.g., gastric ulcer, ulcerative colitis, etc.)], etc.; a uterine contraction suppressing agent; an agent for ameliorating and preventing/treating various disorders associated with excessive uterine contractions, including hypertonic labor, false contractions, prolonged pregnancy, tonic uterine contractions, fetal distress, uterine rupture, cervical laceration, preterm delivery, uterine myoma, uterine abnormalities, uterine adenomyosis, abnormalities in expulsive force, chronic inflammatory disease of uterus, maternal care during multiple pregnancy, malpresentation, Prader-Willi syndrome, dysmenorrhea, etc.; an eating (appetite) stimulant; anorexia; insomnia; immune/inflammatory disease (e.g., rheumatoid arthritis, arthritis deformans, etc., preferably, as an agent for preventing/treating hypertension, anorexia, menopausal symptoms, insomnia, immune/inflammatory disease, etc., and more preferably, hypertension, anorexia, menopausal symptoms, insomnia, etc.

Furthermore, the double-stranded RNA described in (5) above and the ribozyme described in (7) above can be used as an agent for preventing/treating, e.g., sterility, hypothyroidism, etc.; (preferably, as a prolactin production suppressing agent), etc.

Moreover, the double-stranded RNA described in (9) above and the ribozyme described in (11) above can be used as an agent for preventing/treating, e.g., sterility, hypothyroidism, etc.; (preferably, as a prolactin production suppressing agent), etc.

The double-stranded RNA can be designed based on a sequence of the polynucleotide of the present invention and manufactured by modifications of publicly known methods (e.g., Nature, 411, 494, 2001).

The ribozyme can be designed based on a sequence of the polynucleotide of the present invention and manufactured by modifications of publicly known methods (e.g., TRENDS in Molecular Medicine, 7, 221, 2001). For example, the ribozyme can be manufactured by ligating a publicly known ribozyme to a part of the RNA encoding the peptide of the present invention. A part of the RNA encoding the peptide of the present invention includes a portion proximal to a cleavage site on the RNA of the present invention, which may be cleaved by a publicly known ribozyme (RNA fragment).

Where the double-stranded RNA or ribozyme described above is used as the preventive/therapeutic agents described above, the double-stranded RNA or ribozyme is prepared into a pharmaceutical preparation in the same way as in the antisense polynucleotide, and the preparation can be provided for administration.

[6] DNA Transgenic Animal

The present invention provides a non-human mammal bearing the DNA encoding the polypeptide of the present invention which is exogenous (hereinafter briefly referred to as the exogenous DNA of the present invention) or its variant DNA (sometimes briefly referred to as the exogenous variant DNA of the present invention).

That is, the present invention provides:
(1) a non-human mammal bearing the exogenous DNA of the present invention or its variant DNA;
(2) the mammal according to (1), wherein the non-human mammal is a rodent;
(3) the mammal according to (2), wherein the rodent is mouse or rat; and,
(4) a recombinant vector containing the exogenous DNA of the present invention or its variant DNA and capable of expressing in a mammal.

The non-human mammal bearing the exogenous DNA of the present invention or its variant DNA (hereinafter briefly referred to as the DNA transgenic animal of the present invention) can be produced by transferring a desired DNA into an unfertilized egg, a fertilized egg, a spermatozoon, a germinal cell containing a primordial germinal cell thereof, etc., preferably in the embryogenic stage in the development of a non-human mammal (more preferably in the single cell or fertilized cell stage and generally before the 8-cell phase), by means, such as the calcium phosphate method, the electric pulse method, the lipofection method, the agglutination method, the microinjection method, the particle gun method, the DEAE-dextran method, etc. Also, it is possible to transfer the exogenous DNA of the present invention into a somatic cell, a living organ, a tissue cell, etc. by the DNA transfer, and utilize the transformant for cell culture, tissue culture, etc. In addition, these cells may be fused with the above-described germinal cell by a publicly known cell fusion method to prepare the DNA transgenic animal of the present invention.

Examples of the non-human mammals that can be used include bovine, swine, sheep, goat, rabbits, dogs, cats, guinea pigs, hamsters, mice, rats, etc. Above all, preferred are rodents, especially mice (e.g., C57Bl/6 strain, DBA2 strain, etc. for a pure line and for a cross line, B6C3F$_1$ strain, BDF$_1$ strain B6D2F$_1$ strain, BALB/c strain, ICR strain, etc.), rats (Wistar, SD, etc.) or the like, since they are relatively short in ontogeny and life cycle from a standpoint of producing model animals for human disease.

"Mammal" in a recombinant vector that can be expressed in the mammal includes the aforesaid non-human mammal and human.

The exogenous DNA of the present invention refers to the DNA of the present invention that is once isolated/extracted from a mammal, not the DNA of the present invention inherently possessed by a non-human mammal.

The mutant DNA of the present invention includes mutants resulting from variation (e.g., mutation, etc.) in the base sequence of the original DNA of the present invention, specifically DNAs resulting from base addition, deletion, substitution with other bases, etc. and further includes abnormal DNA.

The abnormal DNA is intended to mean the DNA that expresses the abnormal polypeptide of the present invention and exemplified by such a DNA that expresses a polypeptide capable of suppressing the functions of the normal polypeptide of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the polypeptide of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include 1) promoters for DNA derived from viruses (e.g., simian virus, cytomegalovirus, Moloney leukemia virus, JC virus, breast cancer virus, poliovirus, etc.), and 2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), peptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among them, cytomegalovirus promoters, human peptide elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus, and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal polypeptide of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using complementary DNA prepared by a publicly known method from RNA of liver, kidney, thyroid cell or fibroblast origin as a starting material. Also, an exogenous abnormal DNA can be obtained using complementary DNA prepared by a publicly known method from RNA of human fibroblast origin as a starting material. Alternatively, the translational region for a normal polypeptide translational region obtained by the cell or tissue described above can be made variant by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transferred at the fertilized egg cell stage in a manner such that the DNA is certainly present in all the germinal cells and somatic cells of the target mammal. The fact that the exogenous DNA of the present invention is present in the germinal cells of the animal prepared by DNA transfer means that all offspring of the prepared animal will maintain the exogenous DNA of the present invention in all of the germinal cells and somatic cells thereof the offspring of the animal that inherits the exogenous DNA of the present invention also have the exogenous DNA of the present invention in all of the germinal cells and somatic cells thereof.

The non-human mammal in which the normal exogenous DNA of the present invention has been transferred can be passaged as the DNA-bearing animal under ordinary rearing environment, by confirming that the exogenous DNA is stably retained by crossing.

By transfer of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfer means that the DNA of the present invention is excessively present in all of the germinal cells and somatic cells thereof the offspring of the animal that inherits the exogenous DNA of the present invention have excessively the DNA of the present invention in all of the germinal cells and somatic cells thereof.

It is possible to obtain homozygous animals having the transferred DNA in both homologous chromosomes and breed male and female of the animal so that all the progeny have this DNA in excess.

In a non-human mammal bearing the normal DNA of the present invention, the normal DNA of the present invention is expressed to a high level, and may eventually develop the hyperfunction of the polypeptide of the present invention by promoting the functions of endogenous normal DNA. Therefore, the animal can be utilized as a pathologic model animal for such a disease. Specifically, using the normal DNA transgenic animal of the present invention, it becomes possible to elucidate the hyperfunction by the polypeptide of the present invention and to clarify the pathological mechanism of the disease associated with the polypeptide of the present invention and to determine how to treat the disease.

Furthermore, since a mammal transfected with the exogenous normal DNA of the present invention exhibits an increasing symptom of the polypeptide of the present invention, the animal is usable for screening of preventive/therapeutic agents for the disease associated with the polypeptide of the present invention. For example, a mammal transfected with the exogenous DNA encoding the polypeptide A1 of the present invention (hereinafter briefly referred to as the exogenous DNA (A1) of the present invention) shows an increasing symptom of the polypeptide A1 of the present invention, and is thus available also for a test of screening agents for preventing/treating the diseases associated with the polypeptide A1 of the present invention (e.g., hypertension, anorexia, menopausal symptoms, insomnia, etc.). A mammal transfected with the exogenous DNA encoding the polypeptide A2 of the present invention (hereinafter briefly referred to as the exogenous DNA (A2) of the present invention) shows an increasing symptom of the polypeptide A2 of the present invention, and is thus available also for a test of screening agents for preventing/treating the diseases associated with the polypeptide A2 of the present invention (e.g., sterility, hypothyroidism, etc.). A mammal transfected with the exogenous DNA encoding the polypeptide B of the present invention (hereinafter briefly referred to as the exogenous DNA (B) of the present invention) shows an increasing symptom of the polypeptide B of the present invention, and is thus available also for a test of screening agents for preventing/treating the diseases associated with the polypeptide B of the present invention (e.g., sterility, hypothyroidism, etc.).

On the other hand, non-human mammal having the exogenous abnormal DNA of the present invention can be passaged under normal breeding conditions as the DNA-bearing animal by confirming the stable retaining of the exogenous DNA via crossing. In addition, the objective exogenous DNA can be utilized as a starting material by inserting the DNA into the plasmid described above. The DNA construct with a promoter can be prepared using conventional DNA engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring passaged the exogenous DNA of the present invention contains the abnormal DNA of the present invention in all of the germinal and somatic cells. A homozygous animal having the introduced DNA on both of homologous chromosomes can be acquired and then by mating these male and female animals, all the offspring can be bred to have the DNA.

Since the non-human mammal having the abnormal DNA of the present invention expresses the abnormal DNA of the present invention at a high level, the animal may cause the function inactive type inadaptability of the polypeptide of the present invention by inhibiting the functions of the endogenous normal DNA, and can be utilized as its disease model animal. For example, using the abnormal DNA-transferred animal of the present invention, it is possible to elucidate the mechanism of the function inactive type inadaptability of the polypeptide of the present invention and to study a method for treatment of this disease.

More specifically, the transgenic animal of the present invention expressing the abnormal DNA of the present invention to a high level is also expected to serve as an experimental model for the elucidation of the mechanism of the functional inhibition (dominant negative effect) of a normal polypeptide by the abnormal polypeptide of the present invention in the function inactive type inadaptability of the polypeptide of the present invention.

A mammal transfected with the abnormal exogenous DNA of the present invention has a symptom of the function inactive type inadaptability of the polypeptide of the present invention, and is thus available also for screening test of an agent for preventing/treating the function inactive type inadaptability of the polypeptide of the present invention. For example, a mammal transfected with exogenous abnormal DNA (hereinafter briefly referred to as the exogenous abnormal DNA(A1) of the present invention) in the DNA encoding the polypeptide A1 of the present invention has a symptom of the function inactive type inadaptability of the polypeptide A1 of the present invention and is thus available also for screening test of an agent for preventing/treating disorders in the function inactive type inadaptability of the polypeptide A1 of the present invention (e.g., hypotension, obesity, lethargy, time zone change syndrome, sterility, etc.). A mammal transfected with exogenous abnormal DNA (hereinafter briefly referred to as the exogenous abnormal DNA(A2) of the present invention) in the DNA encoding the polypeptide A2 of the present invention has a symptom of the function inactive type inadaptability of the polypeptide A2 of the present invention and is thus available also for screening test of an agent for preventing/treating disorders in the function inactive type inadaptability of the polypeptide A2 of the present invention (e.g., menopausal symptoms, hyperthyroidism, etc.). A mammal transfected with exogenous abnormal DNA (hereinafter briefly referred to as the exogenous abnormal DNA(B) of the present invention) in the DNA encoding the polypeptide B of the present invention has a symptom of the function inactive type inadaptability of the polypeptide B of the present invention and is thus available also for screening test of an agent for preventing/treating disorders in the function inactive type inadaptability of the polypeptide B of the present invention (e.g., menopausal symptoms, hyperthyroidism, etc.).

Other potential applications of two kinds of the transgenic animals described above include:
1) use as a cell source for tissue culture;
2) elucidation of the association with a peptide that is specifically expressed or activated by the polypeptide of the present invention, through direct analysis of DNA or RNA in tissue of the DNA transgenic animal of the present invention or by analysis of the peptide tissue expressed by the DNA;
3) research in the function of cells derived from tissues that are cultured usually only with difficulty, using cells of tissue bearing the DNA cultured by a standard tissue culture technique;
4) screening for a drug that enhances the functions of cells using the cells described in 3) above; and,
5) isolation and purification of the variant polypeptide of the present invention and preparation of an antibody thereto.

Furthermore, clinical conditions of a disease associated with the polypeptide of the present invention, including the function inactive type inadaptability of the polypeptide of the present invention can be determined using the DNA transgenic animal of the present invention. Also, pathological findings on each organ in a disease model associated with the polypeptide of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a polypeptidase such as trypsin, etc., followed by establishing the line of culturing or cultured cells. Furthermore, the DNA transgenic animal of the present invention can serve as identification of cells capable of producing the polypeptide of the present invention, and as studies on association with apoptosis, differentiation or propagation or on the mechanism of signal transduction in these properties to inspect any abnormality therein. Thus the DNA transgenic animal of the present invention can provide an effective research material for the polypeptide of the present invention and for elucidating the function and effect thereof.

To develop pharmaceuticals for the treatment of diseases associated with the polypeptide of the present invention, including the function inactive type inadaptability of the polypeptide of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the polypeptide of the present invention, using the DNA transgenic animal of the present invention or a vector capable of expressing the exogenous DNA of the present invention.

[7] Knockout Animal

The present invention provides a non-human mammal embryonic stem cell bearing the DNA of the present invention inactivated and a non-human mammal deficient in expressing the DNA of the present invention.

Thus, the present invention provides:
1) a non-human embryonic stem cell in which the DNA of the present invention is inactivated;
2) the embryonic stem cell according to 1), wherein the DNA is inactivated by introducing a reporter gene (e.g., β-galactosidase gene derived from *Escherichia coli*);
3) the embryonic stem cell according to 1), which is resistant to neomycin;
4) the embryonic stem cell according to 1), wherein the non-human mammal is a rodent;
5) the embryonic stem cell according to 4), wherein the rodent is mouse;
6) a non-human mammal deficient in expressing the DNA of the present invention, wherein the DNA is inactivated;
7) the non-human mammal according to 6), wherein the DNA is inactivated by inserting a reporter gene (e.g., β-galactosidase derived from *Escherichia coli*) therein and the reporter gene is capable of being expressed under control of a promoter for the DNA of the present invention;
8) the non-human mammal according to 6), which is a rodent;
9) the non-human mammal according to 8), wherein the rodent is mouse; and,
10) a method of screening a compound or its salt that promotes or inhibits the promoter activity to the DNA of the present invention, which comprises administering a test compound to the mammal according to 7) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the polypeptide A of the present invention (hereinafter sometimes referred to as the knockout DNA of the present invention) by substantially inactivating the activities of the polypeptide A of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., polyA additional signal, etc.) in the intron between exons to, thus inhibit the synthesis of complete messenger RNA and eventually destroy the gene (hereinafter simply referred to as targeting vector). The thus-obtained ES cells to the Southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the BDF$_1$ mouse (F$_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The BDF$_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is desirable to identify sexes as soon as possible also in order to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1-10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells be monitored at passage and cells found to be morphologically abnormal in culture, if any, be abandoned.

By allowing ES cells to reach a high density in mono-layers or to form cell aggregates in suspension under appropriate conditions, it is possible to spontaneously differentiate them to various cell types, for example, pariental and visceral muscles, cardiac muscle, or the like (M. J. Evans and M. H. Kaufman, Nature, 292, 154, 1981; G R. Martin, Proc. Natl. Acad. Sci. U.S.A., 78, 7634, 1981; T. C. Doetschman et al., Journal of Embryology Experimental Morphology, 87, 27, 1985). The cells deficient in expression of the DNA of the present invention, which are obtainable from the differentiated ES cells of the present invention, are useful for studying the functions of the polypeptide A of the present invention cytologically or molecular biologically.

The non-human mammal deficient in expression of the DNA of the present invention can be identified from a normal animal by measuring the amount of mRNA in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The knockout cells with the DNA of the present invention disrupted can be identified by Southern hybridization analysis with a DNA fragment on or near the DNA of the present invention as a probe, or by PCR analysis using a DNA sequence on the targeting vector and another DNA sequence which is not included in the targeting vector as primers. When non-human mammalian embryonic stem cells are used, a cell line wherein the DNA of the present invention is inactivated by homologous recombination is cloned; the resulting cloned cell line is injected to, e.g., a non-human mammalian embryo or blastocyte, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the polypeptide A of the present invention. The individuals deficient in homozygous expression of the polypeptide A of the present invention can be obtained from offspring of the intercross between the heterozygotes.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell in which the DNA of the present invention is inactivated is very useful for preparing a non-human mammal deficient in expression of the DNA of the present invention.

Since the non-human mammal in which the DNA of the present invention is inactivated lacks various biological activities derived from the polypeptide A of the present invention, such an animal can be a disease model suspected of inactivated biological activities of the polypeptide A of the present invention and thus, offers an effective study to investigate causes for and therapy for these diseases.

[7a] Method for Screening Compounds Having Therapeutic/Prophylactic Effects on Diseases Caused by Deficiency, Damages, Etc. of the DNA of the Present Invention The non-human mammal deficient in expression of the DNA of the present invention can be employed for the screening of compounds having therapeutic/prophylactic effects for diseases caused by deficiency, damages, etc. of the DNA of the present invention.

That is, the present invention provides a method for screening of a compound or its salt having therapeutic/preventive effects for diseases caused by deficiency, damages, etc. of the DNA of the present invention, which comprises administering a test compound to the non-human mammal deficient in expression of the DNA of the present invention and monitoring/measuring a change occurred in the animal.

As the non-human mammal deficient in expression of the DNA of the present invention, which can be employed for the screening method, the same examples as given hereinabove apply.

Examples of the test compounds include peptides, proteins, antibodies, non-peptide compounds, synthetic compounds, fermentation products, cell extracts, plant extracts, animal tissue extracts, blood plasma, and the like and these compounds may be novel compounds or publicly known compounds.

Specifically, the non-human mammal deficient in the expression of the DNA of the present invention is treated with a test compound, comparison is made with an intact animal for control and changes in each organ, tissue, disease conditions, etc. of the animal is used as an index to assess therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, an amount of a test compound administered can be selected depending on administration route, property of the test compound, and the like.

For example, when a compound having therapeutic/prophylactic effects on diseases such as obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, etc. is screened using the non-human mammal deficient in the expression of the DNA of the present invention wherein the DNA encoding the polypeptide A1 of the present invention is inactivated, the non-human mammal deficient in expression of the DNA of the present invention is subjected to a sugar loading treatment. Then, a test compound is administered before or after the sugar loading treatment and, blood sugar level, body weight change, etc. of the animal is measured with passage of time.

In the screening method above, when a test compound is given to an animal to be tested and found to reduce the blood sugar level of the animal to at least about 10%, preferably at least about 30% and more preferably at least about 50%, the test compound can be selected as a compound having therapeutic/prophylactic effects on the diseases described above.

Furthermore, when a compound having therapeutic/prophylactic effects on diseases such as prolactin release deficiency (e.g., ovarian hypofunction, spermatic underdevelopment, menopausal symptoms, etc.), hyperthyroidism, etc. is screened using the non-human mammal deficient in the expression of the DNA of the present invention wherein the DNA encoding the polypeptide A2 of the present invention is inactivated, the non-human mammal deficient in expression of the DNA of the present invention is given to the non-human mammal deficient in the expression of the DNA of the present invention. Then, differences in development of prolactin release deficiency (e.g., ovarian hypofunction, spermatic underdevelopment, menopausal symptoms, etc.), hyperthyroidism, etc. or differences in blood prolactin level, etc. from the group administered with no test compound are monitored with passage of time.

In the screening method above, when a test compound is given to an animal to be tested and found to reduce the blood prolactin level of the animal to at least about 10%, preferably at least about 30% and more preferably at least about 50%, the test compound can be selected as a compound having therapeutic/prophylactic effects on the diseases described above.

Also, when a compound having therapeutic/prophylactic effects on diseases such as prolactin release deficiency (e.g., ovarian hypofunction, spermatic underdevelopment, menopausal symptoms, etc.), hyperthyroidism, etc. is screened using the non-human mammal deficient in the expression of the DNA of the present invention wherein the DNA encoding the polypeptide B of the present invention is inactivated, the non-human mammal deficient in expression of the DNA of the present invention is administered to the non-human mammal deficient in the expression of the DNA of the present invention. Then, differences in development of prolactin release deficiency (e.g., ovarian hypofunction, spermatic underdevelopment, menopausal symptoms, etc.), hyperthyroidism, etc. or differences in blood prolactin level, etc. from the group administered with no test compound are monitored with passage of time.

In the screening method above, when a test compound is given to an animal to be tested and found to reduce the blood prolactin level of the animal to at least about 10%, preferably at least about 30% and more preferably at least about 50%, the test compound can be selected as a compound having therapeutic/prophylactic effects on the diseases described above.

The compound obtained using the screening method above is a compound selected from the test compounds described above and has therapeutic/prophylactic effects on the diseases caused by deficiency, damages, etc. of the polypeptide A of the present invention and can thus be used as a medicament such as a safe and low-toxic agent for treating/preventing these diseases. In addition, compounds derived from the compound obtained using the screening can also be used as well.

The compound obtained by the screening above may form its salts, and salts with physiologically acceptable acids (e.g., inorganic acids or organic acids) or bases (e.g., alkali metal salts), etc. can be used as salts of the compound, with physiologically acceptable acid addition salts being particularly preferred. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), and the like.

A medicament comprising the compound obtained by the above screening method or its salts may be manufactured in the same way as in the manufacturing of the medicament comprising the polypeptide A of the present invention described above.

The pharmaceutical preparation thus obtained is safe and low toxic, and can be administered to human or other mammal (e.g., rat, mouse, guinea pig, rabbit, sheep, swine, bovine, horse, cat, dog, monkey, etc.).

The dose of the compound or its salt to be administered varies depending upon target disease, subject to be administered, route of administration, etc. For example, when the compound is orally administered, the compound is generally administered to the adult patient (as 60 kg body weight) with obesity in a daily dose of about 0.1 to 100 mg, preferably about 1.0 to 50 mg, more preferably about 1.0 to 20 mg. For parenteral administration, a single dose of the compound varies depending upon subject to be administered, target disease, etc. When the compound is administered to the adult patient (as 60 kg body weight) with obesity in the form of, e.g., an injectable preparation, it is generally advantageous to administer the compound intravenously in a daily dose of about 0.01 to 30 mg, preferably about 0.1 to 20 mg, more preferably about 0.1 to 10 mg. For other animal species, the corresponding dose as converted per 60 kg weight can be administered.

[7b] Method for Screening a Compound that Promotes or Inhibits the Activity of a Promoter to the DNA of the Present Invention The present invention provides the method for screening a compound or its salt that promotes or inhibits the activities of a promoter to the DNA of the present invention, which comprises administering a test compound to a non-human mammal deficient in expression of the DNA of the present invention and detecting expression of the reporter gene.

In the screening method described above, the non-human mammal deficient in expression of the DNA of the present invention is selected from the aforesaid non-human mammal deficient in expression of the DNA of the present invention, as an animal in which the DNA of the present invention is inactivated by introducing a reporter gene and the reporter gene can be expressed under control of a promoter to the DNA of the present invention.

The same examples of the test compound apply to specific compounds used for the screening.

As the reporter gene, the same specific examples described above apply, and β-galactosidase (lacZ), soluble alkaline phosphatase gene, luciferase gene and the like are preferably employed.

Since a reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the polypeptide A of the present invention is substituted with, e.g., β-galactosidase gene (lacZ) derived from *Escherichia coli*, β-galactosidase is expressed in a tissue where the polypeptide A of the present invention should originally be expressed, instead of the polypeptide A of the present invention. Thus, the state of expression of the polypeptide A of the present invention can be readily monitored in vivo of an animal by staining with a reagent, e.g., 5-bromo-4-chloro-3-indolyl-β-galactopyranoside (X-gal), which is substrate for β-galactosidase. Specifically, a mouse deficient in the polypeptide A of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/ PBS solution, the color formed is monitored. Alternatively, mRNA encoding lacZ may be detected in a conventional manner.

The compound or its salt obtained using the screening method supra is a compound, which is selected from the test compounds described above and promotes or inhibits the promoter activity to the DNA of the present invention.

The compound obtained by the screening method above may be used in the form of salts with physiologically acceptable acids (e.g., inorganic acids, etc.) or bases (e.g., organic acids, etc.), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), and the like.

The compound or its salt that promotes the promoter activity to the DNA encoding the polypeptide A1 of the present invention can promote the expression of the polypeptide A1 of the present invention to promote the function of said peptide, and is thus useful as a medicament such as an agent for preventing/treating, for example, hypotension, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, sleeping disorders [e.g., primary insomnia, circadian rhythm disorders (e.g., change in physical conditions caused by three-shift work, time zone change syndrome (jet lag), etc.)], lethargy, sterility, seasonal depression, reproductive dysfunction, endocrine diseases, senile dementia, Alzheimer's disease, various age-related disorders, cerebral circulatory disorder (e.g., apoplexy, etc.), head injury, spinal cord injury, epilepsy, anxiety, depression, manic-depressive disorder, schizophrenia, alcoholism, Parkinson's disease, arteriosclerosis, arrhythmia, premenstral syndrome, glaucoma, cancer, AIDS, diabetes mellitus, etc.

The compound or its salt that promotes the promoter activity to the DNA encoding the polypeptide A2 of the present invention can promote the expression of the polypeptide A2 of the present invention to promote the function of said peptide, and is thus useful as a medicament such as an agent for preventing/treating, e.g., prolactin release deficiency (e.g., ovarian hypofunction, spermatic underdevelopment, menopausal symptoms, etc.), hyperthyroidism, etc.

The compound or its salt that promotes the promoter activity to the DNA encoding the polypeptide B of the present invention can promote the expression of the polypeptide B of the present invention to promote the function of said peptide, and is thus useful as a medicament such as an agent for preventing/treating, e.g., prolactin release deficiency (e.g., ovarian hypofunction, spermatic underdevelopment, menopausal symptoms, etc.), hyperthyroidism, etc.

Furthermore, the compound or its salt that inhibits the promoter activity to the DNA encoding the polypeptide A1 of the present invention can inhibit the expression of the polypeptide A1 of the present invention to inhibit the function of said peptide, and is thus useful as an eating (appetite) stimulant; as a medicament such as a safe and low-toxic agent for preventing/treating, e.g., hypertension, anorexia, menopausal symptoms, insomnia, immune/inflammatory disease (e.g., rheumatoid arthritis, arthritis deformans, etc.), etc.

Also, the compound or its salt that inhibits the promoter activity to the DNA encoding the polypeptide A2 of the present invention can inhibit the expression of the polypeptide A2 of the present invention to inhibit the function of said peptide, and is thus useful as a medicament such as a safe and low-toxic agent for preventing/treating, e.g., pituitary tumor, diencephalon tumor, menstrual disorder, autoimmune disease, prolactinoma, sterility, impotence, amenorrhea, lactorrhea, hyperpituitarism, Chiari-Frommel syndrome, Argonz-del Castillo syndrome, Forbes-Albright syndrome, lymphoma, Sheehan's syndrome, spermatogenesis disorder, hypothyroidism, etc.; (preferably, as a prolactin production suppressing agent), etc.

Moreover, the compound or its salt that inhibits the promoter activity to the DNA encoding the polypeptide B of the present invention can inhibit the expression of the polypeptide B of the present invention to inhibit the function of said peptide, and is thus useful as a medicament such as a safe and low-toxic agent for preventing/treating, e.g., pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, hypothyroidism, etc.; (preferably, as a prolactin production suppressing agent), etc.

In addition, compound derived from the compounds obtained by the screening above may be employed as well.

A medicament comprising the compound or its salt obtained by the screening method supra may be manufactured in a manner similar to the method for preparing the medicament comprising the polypeptide A of the present invention or its salt described above.

The pharmaceutical preparation thus obtained is safe and low toxic, and can be administered to human or other mammal (e.g., rat, mouse, guinea pig, rabbit, sheep, swine, bovine, horse, cat, dog, monkey, etc.).

The dose of the compound or its salt varies depending on target disease, subject to be administered, route for administration, etc.; for example, when the compound that promotes the promoter activity to the DNA of the present invention is orally administered, the dose is normally about 0.1 to about 100 mg, preferably about 1.0 to about 50 mg, more preferably about 1.0 to about 20 mg per day for the adult patient (as 60 kg body weight) with obesity. In parenteral administration, a single dose of the compound varies depending on subject to be administered, target disease, etc. but when the compound that promotes the promoter activity to the DNA of the present invention is administered to the adult patient (as 60 kg body weight) with obesity in the form of, e.g., injectable preparation, it is advantageous to administer the compound intravenously at a single dose of about 0.01 to about 30 mg, preferably about 0.1 to about 20 mg and more preferably about 0.1 to about 10 mg per day. For other animal species, the corresponding dose as converted per 60 kg weight can be administered.

On the other hand, when the compound that inhibits the promoter activity to the DNA of the present invention is orally administered, the dose is normally about 0.1 to about 100 mg, preferably about 1.0 to about 50 mg, more preferably about 1.0 to about 20 mg per day for the adult patient (as 60 kg body weight) with anorexia. In parenteral administration, a single dose of the compound varies depending on subject to be administered, target disease, etc. When the compound that inhibits the promoter activity to the DNA of the present invention is administered in the form of, e.g., injectable preparation, it is advantageous to administer the compound intravenously to the adult patient (as 60 kg body weight) with anorexia at a single dose of about 0.01 to about 30 mg, preferably about 0.1 to about 20 mg, more preferably about 0.1 to about 10 mg per day. For other animal species, the corresponding dose as converted per 60 kg weight can be administered.

As described above, the non-human mammal deficient in expression of the DNA of the present invention is extremely useful for screening the compound or its salt that promotes or inhibits the activity of a promoter to the DNA of the present invention and can greatly contribute to the elucidation of causes for various diseases suspected of deficiency in expression of the DNA of the present invention and for the development of prophylactic/therapeutic agent for these diseases.

In addition, a so-called transgenic animal (gene transferred animal) can be prepared by using the DNA containing a promoter region of the polypeptide of the present invention, ligating genes encoding various proteins downstream and injecting the same into oocytes of an animal. It is then possible to synthesize the polypeptide therein specifically and study its activity in vivo. When an appropriate reporter gene is ligated to the promoter site above and a cell line that express the gene is established, the resulting system can be utilized as the survey system for a low molecular compound having the action of specifically promoting or inhibiting the in vivo productivity of the protein per se of the present invention.

Throughout the specification and drawings, where bases, amino acids, etc. are shown by their codes, these codes are denoted in accordance with the IUPAC-IUB Commission on Biochemical Nomenclature or by the common codes in the art, examples of which are given below. For amino acids that may have the optical isomer, L form is presented unless otherwise indicated.

DNA: deoxyribonucleic acid
cDNA complementary deoxyribonucleic acid
A: adenine
T: thymine
G: guanine
C: cytosine
Y: thymine or cytosine
N: thymine, cytosine, adenine or guanine
R: adenine or guanine
M: cytosine or adenine
W: thymine or adenine
S: cytosine or guanine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
TFA: trifluoroacetic acid
EIA: enzyme immunoassay
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
H is or H: histidine
Phe or F: phenylalanine
Tyr or Y: tyrosine
Trp or W: tryptophan
Pro or P: proline
Asn or N: asparagine
Gln or Q: glutamine
pGlu pyroglutamic acid
Me: methyl group
Et: ethyl group
Bu: butyl group
Ph: phenyl group
TC: thiazolidine-4(R)-carboxamido group
Bom: benzyloxymethyl
NMP: N-methylpyrrolidone
PAM: phenylacetamidomethyl Substituents, protecting groups and reagents frequently used in this specification are presented as the codes below.
Tos p-toluenesulfonyl
HONB: 1-hydroxy-5-norbornene-2,3-dicarboxylmide
Bzl: benzyl
Z: benzyloxycarbonyl
Br—Z: 2-bromobenzyl oxycarbonyl
Cl—Z: 2-chlorobenzyloxycarbonyl
Boc: t-butoxycarbonyl
HOBt: 1-hydroxybenztriazole
DCC: N,N'-dicyclohexylcarbodiimide
TFA: trifluoroacetic acid
Fmoc: N-9-fluorenyl methoxycarbonyl
DNP: dinitrophenol
Bum: t-butoxymethyl
Trt: trityl
BSA bovine serum albumin
CHAPS 3-[(3-cholamidopropyl)dimethylammonio]-1-propane sulfonate
PMSF: phenylmethylsulfonyl fluoride
E64: (L-3-trans-carboxiran-2-carbonyl) L-leucyl-agmatin
GDP: guanosine-5'-diphosphate
MEMα: Minimum Essential Medium alpha
Fura-2AM: pentacetoxymethyl 1-[6-amino-2-(5-carboxy-2-oxazolyl)-5-benzofuranyloxy]-2-(2-amino-5-methylphenoxy)-ethane-N,N,N',N'-tetraacetate
HBSS: Hanks' balanced salt
Fluo-3AM: pentacetoxymethyl 1-[2-amino-5-(2,7-dichloro-6-hydroxy-3-oxy-9-xanthenyl)phenoxy]-2-(2-amino-5-methylphenoxy)ethane-N,N,N',N'-tetraacetate
HEPES: 2-[4-(2-hydroxyethyl)-1-piperazinyl]ethanesulfonic acid
MeBzl: 4-methylbenzyl
NMP: N-methylpyrrolidone The sequence identification numbers in the sequence listing of the specification indicate the following sequences.
[SEQ ID NO: 1]
This shows the amino acid sequence of human neuromedin S.
[SEQ ID NO: 2]
This shows the amino acid sequence of rat neuromedin S.
[SEQ ID NO: 3]
This shows the amino acid sequence of mouse neuromedin S.
[SEQ ID NO: 4]
This shows the amino acid sequence of human neuromedin S precursor protein.

[SEQ ID NO: 5]
This shows the amino acid sequence of rat neuromedin S precursor protein.
[SEQ ID NO: 6]
This shows the amino acid sequence of mouse neuromedin S precursor protein.
[SEQ ID NO: 7]
This shows the amino acid sequence of human neuromedin S N-terminal peptide-34.
[SEQ ID NO: 8]
This shows the amino acid sequence of human neuromedin S N-terminal peptide-37.
[SEQ ID NO: 9]
This shows the amino acid sequence of rat neuromedin S N-terminal peptide-34.
[SEQ ID NO: 10]
This shows the amino acid sequence of rat neuromedin S N-terminal peptide-37.
[SEQ ID NO: 11]
This shows the amino acid sequence of mouse neuromedin S N-terminal peptide-34.
[SEQ ID NO: 12]
This shows the amino acid sequence of mouse neuromedin S N-terminal peptide-37.
[SEQ ID NO: 13]
This shows the base sequence of DNA encoding human neuromedin S.
[SEQ ID NO: 14]
This shows the base sequence of DNA encoding rat neuromedin S.
[SEQ ID NO: 15]
This shows the base sequence of DNA encoding mouse neuromedin S.
[SEQ ID NO: 16]
This shows the base sequence of DNA encoding human neuromedin S precursor protein.
[SEQ ID NO: 17]
This shows the base sequence of DNA encoding rat neuromedin S precursor protein.
[SEQ ID NO: 18]
This shows the base sequence of DNA encoding mouse neuromedin S precursor protein.
[SEQ ID NO: 19]
This shows the base sequence of DNA encoding human neuromedin S N-terminal peptide-34.
[SEQ ID NO: 20]
This shows the base sequence of DNA encoding human neuromedin S N-terminal peptide-37.
[SEQ ID NO: 21]
This shows the base sequence of DNA encoding rat neuromedin S N-terminal peptide-34.
[SEQ ID NO: 22]
This shows the base sequence of DNA encoding rat neuromedin S N-terminal peptide-37.
[SEQ ID NO: 23]
This shows the base sequence of DNA encoding mouse neuromedin S N-terminal peptide-34.
[SEQ ID NO: 24]
This shows the base sequence of DNA encoding mouse neuromedin S N-terminal peptide-37.
[SEQ ID NO: 25]
This shows the amino acid sequence of human TGR1.
[SEQ ID NO: 26]
This shows the base sequence of DNA encoding human TGR1.
[SEQ ID NO: 27]
This shows the amino acid sequence of rat TGR1.
[SEQ ID NO: 28]
This shows the base sequence of DNA encoding rat TGR1.
[SEQ ID NO: 29]
This shows the amino acid sequence of mouse TGR1.
[SEQ ID NO: 30]
This shows the base sequence of DNA encoding mouse TGR1.
[SEQ ID NO: 31]
This shows the amino acid sequence of human FM-3.
[SEQ ID NO: 32]
This shows the base sequence of DNA encoding human FM-3.
[SEQ ID NO: 33]
This shows the amino acid sequence of rat FM-3.
[SEQ ID NO: 34]
This shows the base sequence of DNA encoding rat FM-3.
[SEQ ID NO: 35]
This shows the amino acid sequence of mouse FM-3.
[SEQ ID NO: 36]
This shows the base sequence of DNA encoding mouse FM-3.
[SEQ ID NO: 37]
This shows the amino acid sequence of DNA encoding human neuromedin U N-terminal peptide-33.
[SEQ ID NO: 38]
This shows the amino acid sequence of DNA encoding human neuromedin U N-terminal peptide-36.
[SEQ ID NO: 39]
This shows the amino acid sequence of DNA encoding rat neuromedin U N-terminal peptide-33.
[SEQ ID NO: 40]
This shows the amino acid sequence of DNA encoding rat neuromedin U N-terminal peptide-36.
[SEQ ID NO: 41]
This shows the amino acid sequence of DNA encoding mouse neuromedin U N-terminal peptide-33.
[SEQ ID NO: 42]
This shows the amino acid sequence of DNA encoding mouse neuromedin U N-terminal peptide-36.
[SEQ ID NO: 43]
This shows the base sequence of primer 1 used for PCR in EXAMPLE 1 below.
[SEQ ID NO: 44]
This shows the base sequence of primer 2 used for PCR in EXAMPLE 1 below.
[SEQ ID NO: 45]
This shows the base sequence of DNA containing DNA encoding human neuromedin S precursor protein obtained in PCR in EXAMPLE 1 below.
[SEQ ID NO: 46]
This shows the base sequence of primer 3 used for PCR in EXAMPLE 2 below.
[SEQ ID NO: 47]
This shows the base sequence of primer 4 used for PCR in EXAMPLE 2 below.
[SEQ ID NO: 48]
This shows the base sequence of DNA containing DNA encoding rat neuromedin S precursor protein obtained by PCR in EXAMPLE 2 below.
[SEQ ID NO: 49]
This shows the base sequence of primer 5 used for PCR in EXAMPLE 3 below.
[SEQ ID NO: 50]
This shows the base sequence of primer 6 used for PCR in EXAMPLE 3 below.

[SEQ ID NO: 51]

This shows the base sequence of DNA containing DNA encoding mouse neuromedin S precursor protein obtained by PCR in EXAMPLE 3 below.

[SEQ ID NO: 52]

This shows the base sequence of primer used for RT-PCR in EXAMPLE 10 below.

[SEQ ID NO: 53]

This shows the base sequence of primer used for RT-PCR in EXAMPLE 10 below.

[SEQ ID NO: 54]

This shows the base sequence of oligonucleotide used as a probe for the in situ hybridization in EXAMPLE 11 below.

EXAMPLES

The present invention will be described in more detail by referring to EXAMPLES below but is not deemed to be limited thereto.

Neuromedin S, neuromedin S N-terminal peptide and neuromedin U N-terminal peptide are sometimes referred to as NMS, NSNP and NUNP, respectively.

Example 1

Cloning of Gene Encoding Human Neuromedin S Precursor Protein

Using as a template human whole brain-derived Marathon Ready cDNA (Clontech), PCR was carried out using Pyrobest DNA Polymerase (TaKaRa) as well as primer 1 (SEQ ID NO: 43) and primer 2 (SEQ ID NO: 44). As a result, the base sequence shown by SEQ ID NO: 45 was obtained.

In the base sequence represented by SEQ ID NO: 45, a translation frame from initiation codon ATG to termination codon TGA was present. The amino acid sequence of a protein translated from this translation frame is shown by SEQ ID NO: 4. In SEQ ID NO: 4, the sequence of Lys-Arg, from which precursor protein a physiologically active peptide is supposed to be excised (Rouille, Y., et al., Frontiers in Neuroendocrinology, 16, 322, 1995), the peptide sequence represented by SEQ ID NO: 1, which is similar to neuromedin U (Minamino, N., et al., Biochem. Biophys. Res. Commun., 130, 1078, 1985), and the peptide sequences represented by SEQ ID NO: 7 and SEQ ID NO: 8 were present. The presence of the amidation signal Gly-Arg sequence at the carboxyl terminus of SEQ: 1 (Rouille, Y, et al., Frontiers in Neuroendocrinology, 16, 322, 1995) suggested that the carboxyl terminal amino acid Asn in SEQ ID NO: 1 would be in the form of an amide. This peptide sequence represented by SEQ ID NO: 1 was named human neuromedin S (sometimes referred to as human NMS in the specification). The peptide sequences represented by SEQ ID NO: 7 and SEQ ID NO: 8 were named human neuromedin S N-terminal peptide-34 (sometimes referred to as human NSNP-34 in the specification) and human neuromedin S N-terminal peptide-37 (sometimes referred to as human NSNP-37 in the specification), respectively.

Example 2

Cloning of Gene Encoding Rat Neuromedin S Precursor Protein

Using as a template rat whole brain-derived Marathon Ready cDNA (Clontech), PCR was carried out using Pyrobest DNA Polymerase (TaKaRa) as well as primer 3 (SEQ ID NO: 46) and primer 4 (SEQ ID NO: 47). As a result, the base sequence represented by SEQ ID NO: 48 was obtained.

In the base sequence represented by SEQ ID NO: 48, a translation frame from initiation codon ATG to termination codon TAG was present. The amino acid sequence of a protein translated from this translation frame is represented by SEQ ID NO: 5. In SEQ ID NO: 5, the sequence of Lys-Arg, from which precursor protein a physiologically active peptide is supposed to be excised (Rouille, Y, et al., Frontiers in Neuroendocrinology, 16, 322, 1995), the peptide sequence represented by SEQ ID NO: 2, which is similar to neuromedin U (Minamino, N., et al., Biochem. Biophys. Res. Commun., 130, 1078, 1985), and the peptide sequences represented by SEQ ID NO: 9 and SEQ ID NO: 10 were present. The presence of the amidation signal Gly-Arg sequence at the carboxyl terminus of SEQ: 2 (Rouille, Y, et al., Frontiers in Neuroendocrinology, 16, 322, 1995) suggested that the carboxyl terminal amino acid Asn in SEQ ID NO: 2 would be in the form of an amide. This peptide sequence represented by SEQ ID NO: 2 was named rat neuromedin S (sometimes referred to as rat NMS in the specification). The peptide sequences represented by SEQ ID NO: 9 and SEQ ID NO: 10 were named rat neuromedin S N-terminal peptide-34 (sometimes referred to as rat NSNP-34 in the specification) and rat neuromedin S N-terminal peptide-37 (sometimes referred to as rat NSNP-37 in the specification), respectively.

Example 3

Cloning of Gene Encoding Mouse Neuromedin S Precursor Protein

Using as a template cDAN prepared from mouse hypothalamus-derived mRNA, PCR was carried out using Pyrobest DNA Polymerase (TaKaRa), primer 5 (SEQ ID NO: 49) and primer 6 (SEQ ID NO: 50). As a result, the base sequence represented by SEQ ID NO: 51 was obtained.

In the base sequence represented by SEQ ID NO: 51, a translation frame from initiation codon ATG to termination codon TAG was present. The amino acid sequence of a protein translated from this translation frame is represented by SEQ ID NO: 6. In SEQ ID NO: 6, the sequence of Lys-Arg, from which precursor protein a physiologically active peptide is supposed to be excised (Rouille, Y., et al., Frontiers in Neuroendocrinology, 16, 322, 1995), the peptide sequence represented by SEQ ID NO: 3, which is similar to neuromedin U (Minamino, N., et al., Biochem. Biophys. Res. Commun., 130, 1078, 1985), and then the peptide sequences represented by SEQ ID NO: 11 and SEQ ID NO: 12 were present. The presence of the amidation signal Gly-Arg sequence at the carboxyl terminus of SEQ: 3 (Rouille, Y, et al., Frontiers in Neuroendocrinology, 16, 322, 1995) suggested that the carboxyl terminal amino acid Asn in SEQ ID NO: 3 would be in the form of an amide. This peptide sequence represented by SEQ ID NO: 3 was named mouse neuromedin S (sometimes referred to as mouse NMS in the specification). The peptide sequences represented by SEQ ID NO: 11 and SEQ ID NO: 12 were named mouse neuromedin S N-terminal peptide-34 (sometimes referred to as mouse NSNP-34 in the specification) and mouse neuromedin S N-terminal peptide-37 (sometimes referred to as mouse NSNP-37 in the specification), respectively.

Example 4

Preparation of Cho Cells Expressing Human FM-3 or Human TGR1

Human FM-3 (GenBank accession number BC036543; the 209th to 1420th bases) and TGR1 (GenBank accession number AF242874; the 1st to 1240th bases) were cloned into pcDNA3.1 vector (Invitrogen) and then transfected into CHO cells. The stably expressing cell line showing the most significant change in intracellular Ca ion level induced by human neuromedin U was used for experiments.

Example 5

Intracellular Ca Ion Level Increasing Activity of CHO Cells Expressing Human FM-3 or Human TGR1 by NMS The calcium-mobilization assay (Kojima, M., et al., Nature, 402, 656, 1999) was performed on the FLIPR system (Molecular Device) and the maximum value of changes in fluorescence level was made an activity value. A sample was dissolved in assay buffer supplemented with 1% BSA. As a result, human NMS concentration-dependently showed a specific and strong increase in intracellular Ca ion levels, as compared to human FM-3 or human TGR1-expressed cells, indicating that the $EC_{50}$ was $6.5 \times 10^{-11}$ M (FM-3) and $9.1 \times 10^{-11}$ M (TGR1), respectively. Similar results were obtained when rat NMS was used.

Example 6

Receptor Binding Activity of Radiolabeled [$^{125}$I-Tyr$^0$]-NMS in the Membrane Fraction of CHO Cells Expressing Human FM-3 or Human TGR1

The receptor binding test was conducted by an improvement of the Gottschall, et al. method (Gottschall, P. E., et al., Endocrinology, 127, 272, 1990). A crude cell membrane fraction was prepared from human FM-3 or human TGR1-expressed CHO cells. Also, human NMS ([Tyr$^0$]-NMS) added with Tyr at the N terminus was radioactively labeled with $^{125}$I and then purified on HPLC. The crude cell membrane fraction (10 μg) and the radiolabeled peptide (50 pM) were reacted at room temperature for 2 hours in a buffer supplemented with 0.05% CHAPS and 1% BSA in the presence of a competitive peptide. The reaction product was filtered to separate the bound from the unbound radiolabeled peptide. The radioactivity was measured with a TopCount liquid scintillation counter (Packard). As a result, human NMS showed affinity of $IC_{50}=1.2\times10^{-9}$ M to human FM-3 and affinity of $IC_{50}=1.0\times10^{-10}$ M to human TGR1.

The foregoing results reveal that NMS is an endogenous ligand for FM-3 or TGR1.

Example 7

Contractile Activity of NMS on the Chick Rectum

According to the Currie et al. method (Currie, M. G, et al., Science, 221, 71, 1983), fresh chick rectum was preincubated at 37° C. in 3 ml of Krebs-Henseleit solution and a solution of rat NMS prepared by the procedure described in EXAMPLE 14 and dissolved in physiological saline was given. Contraction of the rectum was then measured. As a result, NMS showed a significant contractile activity on the chick rectum at a dose of 10 pmol.

Example 8

Hypertensive Activity by Transvenous Administration of NMS to Rat

Following the method of Minamino, et al. (Minamino, N., et al., Biochem. Biophys. Res. Commun., 130, 1078, 1985), a catheter was placed in the carotid artery of Sprague-Dawley rats anesthetized with pentobarbital (50 mg/kg) to monitor arterial pressure continuously. Rat NMS prepared by the procedure described in EXAMPLE 14 was dissolved in 0.1 ml of physiological saline, which was administered through the catheter placed in the carotid artery. As a result, NMS significantly increased the blood pressure of rats at a dose of 3 nmol/kg by transvenous administration.

Example 9

Effect on Feed Intake by Central Administration of NMS

A catheter was placed in the lateral ventricle of Wistar rats (male, 8 weeks old) and housed under controlled conditions with free access to their diet, while they were accustomed to experimental procedures (22°, light-on from 7:00 to 19:00). Rat NMS prepared by the procedure described in EXAMPLE 14 was dissolved in 10 μl of physiological saline, which was administered into the lateral ventricle through the catheter. (1) For feed intake during the dark phase, NMS was administered at 18:00 and their feed intake was measured during 19:00 to 7:00. In addition, (2) NMS was administered to 14 hour-fasted rats at 9:00 and immediately thereafter the feed intake was measured for 2 hours. As a result, (1) NMS significantly suppressed the feed intake dose-dependently during the dark phase and its effect showed the maximum at 1 nmol. (2) With respect to the 2 hour feed intake of fasted rats, NMS significantly suppressed the feed intake at 0.5 nmol.

Example 10

Analysis of Tissue Distribution of NMS in Rats by RT-PCR

Total RNA was obtained from each tissue of Wistar rats of 8 weeks old. Each part of the brain was obtained by the method of Murakami and Takahashi (Murakami, N. and Takahashi, K., Brain Res., 276, 297, 1983). The RNA obtained was treated with DNase and subjected to reverse transcription using SuperScript II (Invitrogen). Quantitative PCR was carried out using LightCycler-FastStart DNA Master SYBR Green I kit (Roche) and LightCycler System (Roche). Primers used for the quantification are 5'-CTCATCTGTGGTCTGCAAAGAG-3' (SEQ ID NO: 52) and 5'-GCATACAGAAGCAGTAGATGAC-3' (SEQ ID NO: 53). Rat NMScDNA of known quantity was used to prepare the standard curve. The mRNA expression level of rat GAPDH was also determined and used as an internal standard.

As a result, rat NMS mRNA was strongly expressed in the central nervous system, spleen and testis, whereas the expression was at a low level in the pituitary or small intestine. In the central nervous system, the expression was especially strong in the hypothalamus, in which the mRNA was almost specifically expressed in the suprachiasmatic nucleus.

Example 11

Analysis of Expression Distribution by In Situ Hybridization and Change in Expression Level in the Suprachiasmatic Nucleus According to the procedure previously reported (Ozaki, Y., et al., Endocrinology, 143, 4320, 2002), a coronal section slice of 12 μm from rat whole brain was processed for in situ hybridization using $^{35}$S-labeled oligonucleotide probe (5'-

TGAGGAGGGGATCTGTAGCATACAGAAGCA-3') (SEQ ID NO: 54). After washing, the product was developed by autoradiography. The radioactivity was quantitatively determined with an MCID imaging analyzer (Imaging Research) using $^{14}$C as the standard. The site where NMS was expressed was analyzed in the coronal and sagittal sections using rat whole brain and as a result, specific expression in the suprachiasmatic nucleus was observed, which coincided with the results of expression analysis by real time PCR. Expression of rat NMS mRNA was noted at the ventrolateral area of the suprachiasmatic nucleus.

Since the suprachiasmatic nucleus is involved in regulation of circadian rhythms, the expression rhythm of NMS was quantitatively analyzed. As a result, the expression rhythm of NMS which was the strongest at ZT11 and weak at ZT17 was observed with rats maintained under light/dark conditions (light-on from 7:00 to 19:00) (Zeitgeber time, ZT; ZT0, light-on; ZT12, light-off). This expression rhythm disappeared with rats housed for 2 days under constant dark conditions.

Example 12

Phase Shift of Circadian Rhythms in Spontaneous Locomotor Activity by NMS Through Intracerebroventricular Administration Male Wistar rats (300-350 g) were used for the experiment of circadian rhythm phase shift. Intracerebroventricular administration was performed in accordance with the method of Ida et al. (Ida, T., et al., (1999) Brain Res., 821, 526, 1999). The spontaneous locomotor activity was measured by the method of Nakahara et al. (Nakahara, K., et al., Biochem. Biophys. Res. Commun., 318, 156, 2004). The phase shift of spontaneous locomotor activity rhythm was calculated based on the distance between the lines drawn by plotting a delay in time of daily onset of spontaneous locomotor activity for at least 10 days before and after the intracerebroventricular administration of NMS or physiological saline. The onset time of spontaneous locomotor activity was designated as CT12 (circadian time 12). Phase-response data were evaluated using one-way ANOVA followed by Scheffe's multiple comparisons test. In immunostaining for c-Fos protein, rats were maintained under constant dark conditions for 2 weeks and intracerebroventricular administration of 1 nmol of either rat NMS prepared by the procedure described in EXAMPLE 14 and dissolved in physiological saline or physiological saline was performed at CT6. At 90 minutes after the administration, rats were perfused with 2% paraformaldehyde. Immunostaining for c-Fos protein was performed according to the method of Date et al. (Date, Y, et al., Proc. Natl. Acad. Sci. USA, 96, 748, 1999). The intra-suprachiasmatic nucleus perfusion was performed by an improvement of the Piggins et al. method (Piggins, H. D., et al., J. Neurosci., 15, 5612, 1995). Rats were allowed to free run under constant dark conditions for 2 weeks. Each rat was then implanted with a 26-gauge stainless steel guide cannula in the stereotaxic coordinates by Paxinos and Watson (Paxinos, G. and Watson, C., The rat brain in stereotaxic coordinates, Academic Press, New York, USA, 1998) to reach the suprachiasmatic nucleus. Rat NMS prepared by the procedure described in EXAMPLE 14 was dissolved in 1 µl of physiological saline and injected using a 31 gauge stainless steel injector, which was inserted to extend 1 mm below the end of the guide cannula. The spontaneous locomotor activity was recorded for 2 weeks before and after the administration, respectively, according to the method of Nakahara et al. (Nakahara, K., et al., Biochem. Biophys. Res. Commun., 318, 156, 2004). At the conclusion of the experiment, the exact location of the cannula was determined histologically as follows. Rats received 1 µl of India ink to mark the administered site and were then decapitated. The brain was immediately frozen and cut on a cryostat into 20 µm coronal sections, followed by staining with Crystal Violet. The sections were analyzed by comparing to the corresponding rat brain atlas of Paxinos and Watson (Paxinos, G. and Watson, C., The rat brain in stereotaxic coordinates, Academic Press, New York, USA, 1998). When data obtained for the location was more than 200 µm away from the external border of the suprachiasmatic nucleus, the data was excluded from further analysis.

In the suprachiasmatic nucleus, TGR1 mRNA was more abundantly expressed than FM-3 mRNA but two receptors for NMS were expressed. Therefore, effects of NMS on the circadian rhythms of spontaneous locomotor activity by intracerebroventricular administration were examined in rats maintained under constant dark conditions. Administration of 1 nmol of rat NMS at CT3-9 gave advances in the phase of spontaneous locomotor activity, whereas administration at CT22-24 caused delays in the phase. No phase shift was observed at any other time. The phase response curves by NMS changed significantly (ANOVA, $F(14, 28)=2.549$, $P<0.05$). These results were dependent on both phase and dose. Administration of physiological saline did not cause any change in the phase under the same conditions. The length of circadian rhythm was not affected at any time by intracerebroventricular administration of NMS. In addition, the expression of c-Fos protein (a marker for neuron activation) increased in the suprachiasmatic nucleus after intracerebroventricular administration of NMS, as compared to control rats administered with physiological saline. In particular, the c-Fos protein was expressed at the ventrolateral area of the suprachiasmatic nucleus. For further examination of the effects of NMS on the function of suprachiasmatic nucleus, NMS was directly microinjected into the suprachiasmatic nucleus. NMS administered into the nucleus induced phase advances and delays at CT6 and CT23 in the circadian rhythms of spontaneous locomotor activity, respectively, in the same way as in the intracerebroventricular administration. Administration of physiological saline gave no effect. These data suggested that endogenous NMS exhibits strong effects on the function of suprachiasmatic nucleus.

Example 13

Prolactin Releasing Activity of NUNP and NSNP

Changes in prolactin blood level by central administration were monitored. Central administration to conscious rats was performed in the same way as in EXAMPLE 9. The animal received rat NUNP-36 or rat NSNP-37 prepared by the procedure of EXAMPLE 14 and dissolved in physiological saline and then decapitated, followed by blood collection in 20 minutes or blood collection via the tail vein at each time after peptide administration. Prolactin was measured using RIA kit (Amersham). A direct effect on pituitary anterior cells was also examined. The pituitary anterior cells were prepared from Wistar rats (5 week old, male), incubated in a 96-well plate for 2 days and used for the experiment. After rat NUNP-36 or rat NSNP-37 was added, the culture supernatant was recovered 30 minutes after and the prolactin level was measured.

Twenty minutes after central administration of 1 nmol of rat NUNP-36 or rat NSNP-37, blood was collected and the hormone level in blood was measured. As a result, rat NUNP- 36 significantly increased the prolactin level in blood, as compared to the physiological saline group (saline, 7.35±1.53 ng/ml; NUNP 1 nmol, 68.74±10.4 ng/ml). Rat NUNP-36 also significantly increased the prolactin level, though weak (27.34±5.63 ng/ml). On the other hand, thyroid-stimulating hormone level in blood decreased significantly by administration of rat NUNP-36 or rat NSNP-37 (saline, 7.37±0.85 ng/ml; NUNP 1 nmol, 4.92±0.22 ng/ml; NSNP 1 nmol, 5.37±0.51 ng/ml). Furthermore, a significant increase of follicle-stimulating hormone level in blood was noted by administration of rat NUNP-36 (saline, 8.08±1.10 ng/ml; NUNP 1 nmol, 12.26±0.95 ng/ml; NSNP 1 nmol, 10.64±0.72 ng/ml). In other blood hormone (growth hormone, luteinizing hormone, corticosterone) levels, there was a tendency of increasing growth hormone level but any significant change was not noted.

Since a marked prolactin level in blood was noted with centrally administered rat NUNP-36, a dose and time dependency was studied. As a result, a significant increase of prolactin level was observed since 10 minutes after administration at 1 nmol and 0.2 nmol and the level reached the peak in 20 minutes.

It was further studied to see if it was a direct or indirect effect on the hypophysis, using the primary culture system for anterior pituitary cells. Prolactin in the culture supernatant increased TRH level-dependently but no change was noted with rat NUNP-36 at all. For this reason, it was speculated that the increased prolactin level in blood by centrally administered rat NUNP-36 would act on the regulation system of prolactin release in the brain.

Example 14

Synthesis of NMS, NSNP and NUNP

Synthesis of human, rat and mouse neuromedin S (SEQ ID NOS: 1, 2 and 3), human, rat and mouse neuromedin S N-terminal peptide-34 (SEQ ID NOS: 7, 9 and 11), human, rat and mouse neuromedin S N-terminal peptide-37 (SEQ ID NOS: 8, 10 and 12), human, rat and mouse neuromedin U N-terminal peptide-33 (SEQ ID NOS: 37, 39 and 41), and human, rat and mouse neuromedin U N-terminal peptide-36 (SEQ ID NOS: 38, 40 and 42), described in this EXAMPLE, was carried out by the Fmoc solid phase synthesis using a 431A peptide synthesizer (Applied Biosystems), according to the protocol attached. After completion of the synthesis, the resin was washed in methanol, dried and stirred in an appropriate amount of deblocking mixture (composition: crystalline phenol, 1.5 g; water, 1 ml; thioanisole, 1 ml; 1,2-ethanedithiol, 0.5 ml; TFA, 20 ml) for 3 hours thereby to split off the protecting group. After washing with diethyl ether, the synthesized compound was dissolved in an appropriate volume of 0.1% TFA and the solution was applied to SPW-C-ODS column chromatography (Chemco) to remove contaminants. Roughly purified synthetic peptide was purified to a single peak by reverse phase HPLC using μBONDASHERE 15μ $C_{18}$-300 Å. Structure of the synthetic peptide finally obtained was identified using MALDI-TOF MS (Voyager-DE Pro, Applied) and a peptide sequencer (494cLC, Applied Biosystems).

Example 15

Prolactin Release Suppressing Activity by NMS

Changes in prolactin blood level by central administration of NMS were monitored. Central administration to conscious rats was performed as in EXAMPLE 9. Blood was collected by decapitation 20 minutes after peptide administration. Prolactin was assayed using RIA kit (Amersham).

After 1 nmol of rat NMS prepared by the procedure described in EXAMPLE 14 and dissolved in physiological saline was centrally administered, blood hormone levels were determined. As a result, the blood prolactin level significantly decreased in the NMS group as compared to the physiological saline group (saline, 13.1±1.8 ng/ml; NMS1 nmol, 3.6±1.2 ng/ml, $p<0.0001$). The results showed that NMS suppressed the release of prolactin by central administration.

INDUSTRIAL APPLICABILITY (1) (i) The polypeptide comprising the same or substantially the same amino acid sequence as the amino acid sequence represented by SEQ ID NO: 1, SEQ ID NO: 2, SEQ ID NO: 3, SEQ ID NO: 4, SEQ ID NO: 5 or SEQ ID NO: 6, or its partial peptide or its amide, or a salt thereof, (ii) the polynucleotide comprising a polynucleotide encoding the aforesaid polypeptide or its partial peptide, and (iii) the compound or its salt that promotes the activity of the aforesaid polypeptide, its partial peptide or its amide, or a salt thereof, possess, e.g., a digestive tract contractile activity, smooth muscle contractile activity, hypertensive activity, food intake suppressing activity, prolactin release suppressing activity, etc., are associated with phase advances and delays in the circadian rhythms and thus useful for preventing/treating, e.g., hypotension, obesity, lethargy, time zone change syndrome, sterility, etc.

(2) (i) The antibody to the polypeptide comprising the same or substantially the same amino acid sequence as the amino acid sequence represented by SEQ ID NO: 1, SEQ ID NO: 2, SEQ ID NO: 3, SEQ ID NO: 4, SEQ ID NO: 5 or SEQ ID NO: 6, or its partial peptide or its amide, or a salt thereof, (ii) the antisense polynucleotide comprising the entire base sequence complementary or substantially complementary to a polynucleotide comprising the polynucleotide encoding the aforesaid polypeptide or its partial peptide, or a part of the base sequence, and (iii) the compound or its salt that inhibits the activity of the aforesaid polypeptide, its partial peptide or its amide, or a salt thereof, are useful for preventing/treating, e.g., hypertension, anorexia, menopausal symptoms, insomnia, etc.

(3) (i) The polypeptide comprising the same or substantially the same amino acid sequence as the amino acid sequence represented by SEQ ID NO: 7, SEQ ID NO: 8, SEQ ID NO: 9, SEQ ID NO: 10, SEQ ID NO: 11 or SEQ ID NO: 12, or its partial peptide, or a salt thereof, (ii) the polynucleotide comprising a polynucleotide encoding the aforesaid polypeptide or its partial peptide, and (iii) the compound or its salt that promotes the activity of the aforesaid polypeptide, or its partial peptide, or a salt thereof, have the prolactin releasing activity, etc. and are useful for preventing/treating, e.g., menopausal symptoms, hyperthyroidism, etc.

(4) (i) The antibody to the polypeptide comprising the same or substantially the same amino acid sequence as the amino acid sequence represented by SEQ ID NO: 7, SEQ ID NO: 8, SEQ ID NO: 9, SEQ ID NO: 10, SEQ ID NO: 11 or SEQ ID NO: 12, or its partial peptide, or a salt thereof, (ii) the antisense polynucleotide comprising the entire base sequence complementary or substantially complementary to a polynucleotide comprising the polynucleotide encoding the aforesaid polypeptide or its partial peptide, or a part of the base sequence, and (iii) the compound or its salt that inhibits the activity of the aforesaid polypeptide, its partial peptide or its amide, or a salt thereof, are useful for preventing/treating, e.g., sterility, hypothyroidism, etc.

(5) (i) The polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof, (ii) the polynucleotide comprising a polynucleotide encoding the aforesaid polypeptide or its partial peptide, and (iii) the compound or its salt that promotes the activity of the aforesaid polypeptide, or its partial peptide, or a salt thereof, have the prolactin releasing activity, etc. and are useful for preventing/treating, e.g., menopausal symptoms, hyperthyroidism, etc.

(6) (i) The antibody to the polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof, (ii) the antisense polynucleotide comprising the entire base sequence complementary or substantially complementary to a polynucleotide comprising the polynucleotide encoding the aforesaid polypeptide or its partial peptide, or a part of the base sequence, and (iii) the compound or its salt that inhibits the activity of the aforesaid polypeptide, its partial peptide, or a salt thereof, are useful for preventing/treating, e.g., sterility, hypothyroidism, etc.

(7) (i) The polypeptide comprising the same or substantially the same amino acid sequence as the amino acid sequence represented by SEQ ID NO: 1, SEQ ID NO: 2, SEQ ID NO: 3, SEQ ID NO: 4, SEQ ID NO: 5 or SEQ ID NO: 6, its partial peptide or its amide, or a salt thereof, and/or (ii) the protein comprising the same or substantially the same amino acid sequence as the amino acid sequence represented by SEQ ID NO: 25, SEQ ID NO: 27 or SEQ ID NO: 29, its partial peptide, or a salt thereof, and/or (iii) the protein comprising the same or substantially the same amino acid sequence as the amino acid sequence represented by SEQ ID NO: 31, SEQ ID NO: 33 or SEQ ID NO: 35, its partial peptide, or a salt thereof, are useful for screening agents for preventing/treating, e.g., hypotension, obesity, lethargy, time zone change syndrome, sterility, hypertension, anorexia, menopausal symptoms, insomnia, etc.

(8) The polypeptide comprising the same or substantially the same amino acid sequence as the amino acid sequence represented by SEQ ID NO: 7, SEQ ID NO: 8, SEQ ID NO: 9, SEQ ID NO: 10, SEQ ID NO: 11 or SEQ ID NO: 12, or its partial peptide, or a salt thereof, is useful for preventing/treating, e.g., menopausal symptoms, hyperthyroidism, sterility, hypothyroidism, etc.

(9) (i) The polypeptide comprising the same or substantially the same amino acid sequence as the amino acid sequence represented by SEQ ID NO: 37, SEQ ID NO: 38, SEQ ID NO: 39, SEQ ID NO: 40, SEQ ID NO: 41 or SEQ ID NO: 42, or its partial peptide, or a salt thereof, is useful for screening agents for the prevention/treatment of, e.g., menopausal symptoms, hyperthyroidism, sterility, hypothyroidism, etc.

The invention claimed is:

1. An isolated polypeptide, which comprises the amino acid sequence represented by SEQ ID NO: 1, SEQ ID NO: 2 or SEQ ID NO: 3, or its amide, or a salt thereof.

2. An isolated polypeptide, which comprises an amino acid sequence at least 90% identical to the amino acid sequence represented by SEQ ID NO: 1, SEQ ID NO: 2 or SEQ ID NO: 3, and has a signal transduction action, or its amide, or a salt thereof.

3. An isolated polypeptide, which comprises an amino acid sequence at least 95% identical to the amino acid sequence represented by SEQ ID NO: 1, SEQ ID NO: 2 or SEQ ID NO: 3, and has a signal transduction action, or its amide, or a salt thereof.

4. An isolated polypeptide, which consists of the amino acid sequence represented by SEQ ID NO: 1, or its amide, or a salt thereof.

5. A medicament comprising the polypeptide according to claim 1, or its amide, or a salt thereof.

6. A medicament comprising the polypeptide according to claim 2, or its amide, or a salt thereof.

7. A medicament comprising the polypeptide according to claim 3, or its amide, or a salt thereof.

8. A medicament comprising the polypeptide according to claim 4, or its amide, or a salt thereof.

* * * * *

SEQUENCE LISTING

```
<160> NUMBER OF SEQ ID NOS: 54

<210> SEQ ID NO 1
<211> LENGTH: 33
<212> TYPE: PRT
<213> ORGANISM: Homo sapiens

<400> SEQUENCE: 1

Ile Leu Gln Arg Gly Ser Gly Thr Ala Ala Val Asp Phe Thr Lys Lys
                5                   10                  15

Asp His Thr Ala Thr Trp Gly Arg Pro Phe Phe Leu Phe Arg Pro Arg
            20                  25                  30

Asn

<210> SEQ ID NO 2
<211> LENGTH: 36
<212> TYPE: PRT
<213> ORGANISM: Rattus norvegicus

<400> SEQUENCE: 2

Leu Pro Arg Leu Leu His Thr Asp Ser Arg Met Ala Thr Ile Asp Phe
                5                   10                  15

Pro Lys Lys Asp Pro Thr Thr Ser Leu Gly Arg Pro Phe Phe Leu Phe
            20                  25                  30

Arg Pro Arg Asn
        35

<210> SEQ ID NO 3
<211> LENGTH: 36
<212> TYPE: PRT
<213> ORGANISM: Mus musculus
```

-continued

<400> SEQUENCE: 3

Leu Pro Arg Leu Leu Arg Leu Asp Ser Arg Met Ala Thr Val Asp Phe
                 5                  10                  15

Pro Lys Lys Asp Pro Thr Thr Ser Leu Gly Arg Pro Phe Phe Leu Phe
             20                  25                  30

Arg Pro Arg Asn
             35

<210> SEQ ID NO 4
<211> LENGTH: 153
<212> TYPE: PRT
<213> ORGANISM: Homo sapiens

<400> SEQUENCE: 4

Met Lys His Leu Arg Pro Gln Phe Pro Leu Ile Leu Ala Ile Tyr Cys
                 5                  10                  15

Phe Cys Met Leu Gln Ile Pro Ser Ser Gly Phe Pro Gln Pro Leu Ala
             20                  25                  30

Asp Pro Ser Asp Gly Leu Asp Ile Val Gln Leu Glu Gln Leu Ala Tyr
         35                  40                  45

Cys Leu Ser Gln Trp Ala Pro Leu Ser Arg Gln Pro Lys Asp Asn Gln
 50                  55                  60

Asp Ile Tyr Lys Arg Phe Leu Phe His Tyr Ser Arg Thr Gln Glu Ala
 65                  70                  75                  80

Thr His Pro Val Lys Thr Gly Phe Pro Val His Pro Leu Met His
                 85                  90                  95

Leu Ala Ala Lys Leu Ala Asn Arg Arg Met Lys Arg Ile Leu Gln Arg
            100                 105                 110

Gly Ser Gly Thr Ala Ala Val Asp Phe Thr Lys Lys Asp His Thr Ala
        115                 120                 125

Thr Trp Gly Arg Pro Phe Phe Leu Phe Arg Pro Arg Asn Gly Arg Asn
    130                 135                 140

Ile Glu Asp Glu Ala Gln Ile Gln Trp
145                 150

<210> SEQ ID NO 5
<211> LENGTH: 152
<212> TYPE: PRT
<213> ORGANISM: Rattus norvegicus

<400> SEQUENCE: 5

Met Lys His Pro Phe Pro Gln Phe Pro Pro Ile Leu Val Ile Tyr Cys
                 5                  10                  15

Phe Cys Met Leu Gln Ile Pro Ser Ser Gly Ala Ser Pro Pro Leu Ala
             20                  25                  30

Gly Pro Pro Asp Gly Leu Asp Ala Val Asp Pro Glu Arg Leu Ala His
         35                  40                  45

Phe Leu Asn Gln Arg Glu Thr Cys Ser Asn Gln Pro Lys Glu Ser Arg
 50                  55                  60

Asp Val Tyr Lys Arg Phe Leu Phe His Tyr Ser Arg Ala Trp Lys Ser
 65                  70                  75                  80

Thr His Pro Val Asn Ser Glu Phe Ala Pro Val His Pro Leu Met Arg
                 85                  90                  95

Leu Ala Ala Lys Leu Pro Ser Arg Arg Met Lys Arg Leu Pro Arg Leu
            100                 105                 110

Leu His Thr Asp Ser Arg Met Ala Thr Ile Asp Phe Pro Lys Lys Asp
        115                 120                 125

Pro Thr Thr Ser Leu Gly Arg Pro Phe Phe Leu Phe Arg Pro Arg Asn
            130                 135                 140

Gly Arg Tyr Thr Asp Lys Val Gln
145                 150

<210> SEQ ID NO 6
<211> LENGTH: 153
<212> TYPE: PRT
<213> ORGANISM: Mus musculus

<400> SEQUENCE: 6

Met Lys His Pro Leu Pro His Tyr Ser Pro Ile Leu Phe Ile Tyr Cys
                5                   10                  15

Phe Cys Met Leu Gln Ile Pro Ser Ser Gly Ala Ser Pro Pro Leu Ala
            20                  25                  30

Asp Ser Pro Asp Gly Leu Asp Ile Val Asp Pro Glu Arg Leu Ala Tyr
        35                  40                  45

Phe Leu Lys Gln Arg Glu Ile His Ser Asn Gln Pro Lys Glu Asn Gln
    50                  55                  60

Asp Val Tyr Lys Arg Phe Leu Phe His Tyr Ser Arg Thr Arg Lys Pro
65                  70                  75                  80

Thr His Pro Val Ser Ala Glu Phe Ala Pro Val His Pro Leu Met Arg
                85                  90                  95

Leu Ala Ala Lys Leu Ala Ser Arg Arg Met Lys Arg Leu Pro Arg Leu
            100                 105                 110

Leu Arg Leu Asp Ser Arg Met Ala Thr Val Asp Phe Pro Lys Lys Asp
        115                 120                 125

Pro Thr Thr Ser Leu Gly Arg Pro Phe Phe Leu Phe Arg Pro Arg Asn
    130                 135                 140

Gly Arg Tyr Thr Asp Asn Asn Phe Gln
145                 150

<210> SEQ ID NO 7
<211> LENGTH: 34
<212> TYPE: PRT
<213> ORGANISM: Homo sapiens

<400> SEQUENCE: 7

Phe Leu Phe His Tyr Ser Arg Thr Gln Glu Ala Thr His Pro Val Lys
                5                   10                  15

Thr Gly Phe Pro Pro Val His Pro Leu Met His Leu Ala Ala Lys Leu
            20                  25                  30

Ala Asn

<210> SEQ ID NO 8
<211> LENGTH: 37
<212> TYPE: PRT
<213> ORGANISM: Homo sapiens

<400> SEQUENCE: 8

Phe Leu Phe His Tyr Ser Arg Thr Gln Glu Ala Thr His Pro Val Lys
                5                   10                  15

Thr Gly Phe Pro Pro Val His Pro Leu Met His Leu Ala Ala Lys Leu
            20                  25                  30

Ala Asn Arg Arg Met
            35

<210> SEQ ID NO 9

```
<211> LENGTH: 34
<212> TYPE: PRT
<213> ORGANISM: Rattus norvegicus

<400> SEQUENCE: 9

Phe Leu Phe His Tyr Ser Arg Ala Trp Lys Ser Thr His Pro Val Asn
                 5                  10                  15

Ser Glu Phe Ala Pro Val His Pro Leu Met Arg Leu Ala Ala Lys Leu
             20                  25                  30

Pro Ser

<210> SEQ ID NO 10
<211> LENGTH: 37
<212> TYPE: PRT
<213> ORGANISM: Rattus norvegicus

<400> SEQUENCE: 10

Phe Leu Phe His Tyr Ser Arg Ala Trp Lys Ser Thr His Pro Val Asn
                 5                  10                  15

Ser Glu Phe Ala Pro Val His Pro Leu Met Arg Leu Ala Ala Lys Leu
             20                  25                  30

Pro Ser Arg Arg Met
         35

<210> SEQ ID NO 11
<211> LENGTH: 34
<212> TYPE: PRT
<213> ORGANISM: Mus musculus

<400> SEQUENCE: 11

Phe Leu Phe His Tyr Ser Arg Thr Arg Lys Pro Thr His Pro Val Ser
                 5                  10                  15

Ala Glu Phe Ala Pro Val His Pro Leu Met Arg Leu Ala Ala Lys Leu
             20                  25                  30

Ala Ser

<210> SEQ ID NO 12
<211> LENGTH: 37
<212> TYPE: PRT
<213> ORGANISM: Mus musculus

<400> SEQUENCE: 12

Phe Leu Phe His Tyr Ser Arg Thr Arg Lys Pro Thr His Pro Val Ser
                 5                  10                  15

Ala Glu Phe Ala Pro Val His Pro Leu Met Arg Leu Ala Ala Lys Leu
             20                  25                  30

Ala Ser Arg Arg Met
         35

<210> SEQ ID NO 13
<211> LENGTH: 99
<212> TYPE: DNA
<213> ORGANISM: Homo sapiens

<400> SEQUENCE: 13
attctgcagc gaggctcggg gactgctgca gtggacttca ccaagaagga tcacactgcg    60
acctggggac gacccttttt cctttcagg cccaggaat                           99

<210> SEQ ID NO 14
<211> LENGTH: 108
<212> TYPE: DNA
```

<213> ORGANISM: Rattus norvegicus

<400> SEQUENCE: 14

| ctaccgcgat tgctgcacac agattccagg atggctacta tagacttccc taagaaggat | 60 |
| cctaccacca gcttggggcg gccatttttc cttttcaggc ctaggaat | 108 |

<210> SEQ ID NO 15
<211> LENGTH: 108
<212> TYPE: DNA
<213> ORGANISM: Mus musculus

<400> SEQUENCE: 15

| ctgccgcgat tgctgcgcct cgattccagg atggctactg tggacttccc taagaaggat | 60 |
| cctactacca gcctggggag gccatttttc cttttcaggc ctaggaat | 108 |

<210> SEQ ID NO 16
<211> LENGTH: 459
<212> TYPE: DNA
<213> ORGANISM: Homo sapiens

<400> SEQUENCE: 16

| atgaaacatc ttcgtcccca gttccctctc atcttggcca tctactgctt ctgcatgcta | 60 |
| cagattccct cctcaggatt tcctcaacct ttagctgatc cttcagatgg cttggatatt | 120 |
| gtgcagcttg agcagctggc atattgtctg agtcagtggg cacctctttc tcgccaacct | 180 |
| aaggataatc aagacatata caaaaggttt ttgtttcact actccagaac tcaggaggca | 240 |
| acacatccag ttaaaactgg gtttcctcca gtgcatcctc taatgcacct ggctgccaag | 300 |
| ctcgccaaca gcggatgaa gagaattctg cagcgaggct cggggactgc tgcagtggac | 360 |
| ttcaccaaga aggatcacac tgcgacctgg ggacgaccct tttccttttt caggcccagg | 420 |
| aatggaagaa acattgaaga tgaggcccag attcagtgg | 459 |

<210> SEQ ID NO 17
<211> LENGTH: 456
<212> TYPE: DNA
<213> ORGANISM: Rattus norvegicus

<400> SEQUENCE: 17

| atgaaacatc cgttccctca gttccctcca atcctggtca tctactgctt ctgtatgcta | 60 |
| cagatcccct cctcaggagc ttctccacct ttagctggtc ctcctgatgg tttggatgct | 120 |
| gtggacccag agcgactggc acactttctg aaccagaggg aaacatgttc taaccaacct | 180 |
| aaggaaagcc gggatgtata caaaaggttt ttatttcact actcccgagc ttggaagtcg | 240 |
| acacatccag ttaactccga gtttgctccc gtccatccat tgatgcgcct ggccgccaag | 300 |
| cttcccagca gaaggatgaa aagactaccg cgattgctgc acacagattc caggatggct | 360 |
| actatagact tccctaagaa ggatcctacc accagcttgg ggcggccatt tttcctttc | 420 |
| aggcctagga atggaagata cactgacaaa gtccag | 456 |

<210> SEQ ID NO 18
<211> LENGTH: 459
<212> TYPE: DNA
<213> ORGANISM: Mus musculus

<400> SEQUENCE: 18

| atgaaacacc cgctccccca ctattctcca atcctgttca tctactgctt ctgtatgcta | 60 |
| cagattccct cctcaggagc ttccccacct ttagctgatt ctcccgacgg cttggatatt | 120 |

| | |
|---|---|
| gtggatcctg agcgactggc atactttctg aagcagaggg aaatacattc taaccaacct | 180 |
| aaggaaaacc aggatgtata caaaaggttt ttatttcact actccagaac tcggaaacca | 240 |
| acacatccag ttagcgctga gtttgctccg gtccatccat tgatgcgcct ggctgccaag | 300 |
| ctcgccagca gaaggatgaa aagactgccg cgattgctgc gcctcgattc caggatggct | 360 |
| actgtggact tccctaagaa ggatcctact accagcctgg ggaggccatt tttccttttc | 420 |
| aggcctagga atggaagata caccgacaac aacttccag | 459 |

```
<210> SEQ ID NO 19
<211> LENGTH: 102
<212> TYPE: DNA
<213> ORGANISM: Homo sapiens

<400> SEQUENCE: 19
```

| | |
|---|---|
| tttttgtttc actactccag aactcaggag gcaacacatc cagttaaaac tgggtttcct | 60 |
| ccagtgcatc ctctaatgca cctggctgcc aagctcgcca ac | 102 |

```
<210> SEQ ID NO 20
<211> LENGTH: 111
<212> TYPE: DNA
<213> ORGANISM: Homo sapiens

<400> SEQUENCE: 20
```

| | |
|---|---|
| tttttgtttc actactccag aactcaggag gcaacacatc cagttaaaac tgggtttcct | 60 |
| ccagtgcatc ctctaatgca cctggctgcc aagctcgcca acaggcggat g | 111 |

```
<210> SEQ ID NO 21
<211> LENGTH: 102
<212> TYPE: DNA
<213> ORGANISM: Rattus norvegicus

<400> SEQUENCE: 21
```

| | |
|---|---|
| tttttatttc actactcccg agcttggaag tcgacacatc cagttaactc cgagtttgct | 60 |
| cccgtccatc cattgatgcg cctggccgcc aagcttccca gc | 102 |

```
<210> SEQ ID NO 22
<211> LENGTH: 111
<212> TYPE: DNA
<213> ORGANISM: Rattus norvegicus

<400> SEQUENCE: 22
```

| | |
|---|---|
| tttttatttc actactcccg agcttggaag tcgacacatc cagttaactc cgagtttgct | 60 |
| cccgtccatc cattgatgcg cctggccgcc aagcttccca gcagaaggat g | 111 |

```
<210> SEQ ID NO 23
<211> LENGTH: 102
<212> TYPE: DNA
<213> ORGANISM: Mus musculus

<400> SEQUENCE: 23
```

| | |
|---|---|
| tttttatttc actactccag aactcggaaa ccaacacatc cagttagcgc tgagtttgct | 60 |
| ccggtccatc cattgatgcg cctggctgcc aagctcgcca gc | 102 |

```
<210> SEQ ID NO 24
<211> LENGTH: 111
<212> TYPE: DNA
<213> ORGANISM: Mus musculus

<400> SEQUENCE: 24
```

```
tttttatttc actactccag aactcggaaa ccaacacatc cagttagcgc tgagtttgct        60
ccggtccatc cattgatgcg cctggctgcc aagctcgcca gcagaaggat g               111
```

<210> SEQ ID NO 25
<211> LENGTH: 415
<212> TYPE: PRT
<213> ORGANISM: Homo sapiens

<400> SEQUENCE: 25

```
Met Ser Gly Met Glu Lys Leu Gln Asn Ala Ser Trp Ile Tyr Gln Gln
1               5                   10                  15

Lys Leu Glu Asp Pro Phe Gln Lys His Leu Asn Ser Thr Glu Tyr
            20                  25                  30

Leu Ala Phe Leu Cys Gly Pro Arg Arg Ser His Phe Phe Leu Pro Val
        35                  40                  45

Ser Val Val Tyr Val Pro Ile Phe Val Gly Val Ile Gly Asn Val
    50                  55                  60

Leu Val Cys Leu Val Ile Leu Gln His Gln Ala Met Lys Thr Pro Thr
65                  70                  75                  80

Asn Tyr Tyr Leu Phe Ser Leu Ala Val Ser Asp Leu Val Leu Leu
            85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
            180                 185                 190

Pro Asn Gly Ser Leu Val Pro Gly Ser Ala Thr Cys Thr Val Ile Lys
        195                 200                 205

Pro Met Trp Ile Tyr Asn Phe Ile Ile Gln Val Thr Ser Phe Leu Phe
    210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Phe Val
            260                 265                 270

Leu Val Leu Val Phe Ala Ile Cys Trp Ala Pro Phe His Ile Asp Arg
        275                 280                 285

Leu Phe Phe Ser Phe Val Glu Glu Trp Ser Glu Ser Leu Ala Ala Val
    290                 295                 300

Phe Asn Leu Val His Val Val Ser Gly Val Phe Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
            340                 345                 350

His Asp Pro Gln Leu Pro Pro Ala Gln Arg Asn Ile Phe Leu Thr Glu
        355                 360                 365
```

```
Cys His Phe Val Glu Leu Thr Glu Asp Ile Gly Pro Gln Phe Pro Cys
    370                 375                 380

Gln Ser Ser Met His Asn Ser His Leu Pro Thr Ala Leu Ser Ser Glu
385                 390                 395                 400

Gln Met Ser Arg Thr Asn Tyr Gln Ser Phe His Phe Asn Lys Thr
                405                 410                 415

<210> SEQ ID NO 26
<211> LENGTH: 1245
<212> TYPE: DNA
<213> ORGANISM: Homo sapiens

<400> SEQUENCE: 26
atgtcaggga tggaaaaact tcagaatgct tcctggatct accagcagaa actagaagat      60
ccattccaga aacacctgaa cagcaccgag gagtatctgg ccttcctctg cggacctcgg     120
cgcagccact tcttcctccc cgtgtctgtg gtgtatgtgc caattttgt ggtgggggtc      180
attggcaatg tcctggtgtg cctggtgatt ctgcagcacc aggctatgaa gacgcccacc     240
aactactacc tcttcagcct ggcggtctct gacctcctgg tcctgctcct tggaatgccc     300
ctggaggtct atgagatgtg gcgcaactac ccttttcttgt tcgggcccgt gggctgctac     360
ttcaagacgg ccctctttga gaccgtgtgc ttcgcctcca cctcagcat caccaccgtc      420
agcgtggagc gctacgtggc catcctacac ccgttccgcg ccaaactgca gagcacccgg     480
cgccgggccc tcaggatcct cggcatcgtc tggggcttct ccgtgctctt ctccctgccc     540
aacaccagca tccatggcat caagttccac tacttcccca tgggtccct ggtcccaggt      600
tcggccacct gtacggtcat caagcccatg tggatctaca atttcatcat ccaggtcacc     660
tccttcctat tctacctcct ccccatgact gtcatcagtg tcctctacta cctcatggca     720
ctcagactaa agaaagacaa atctcttgag gcagatgaag ggaatgcaaa tattcaaaga     780
ccctgcagaa aatcagtcaa caagatgctg tttgtcttgg tcttagtgtt tgctatctgt     840
tgggcccgt tccacattga ccgactcttc ttcagcttg tggaggagtg gagtgaatcc       900
ctggctgctg tgttcaacct cgtccatgtg gtgtcaggtc tcttcttcta cctgagctca     960
gctgtcaacc ccattatcta taacctactg tctcgccgct tccaggcagc attccagaat    1020
gtgatctctt ctttccacaa acagtggcac tcccagcatg acccacagtt gcccacctgcc   1080
cagcggaaca tcttcctgac agaatgccac tttgtggagc tgaccgaaga tataggtccc    1140
caattcccat gtcagtcatc catgcacaac tctcacctcc caacagccct ctctagtgaa    1200
cagatgtcaa gaacaaacta tcaaagcttc cactttaaca aaacc                    1245

<210> SEQ ID NO 27
<211> LENGTH: 395
<212> TYPE: PRT
<213> ORGANISM: Rattus norvegicus

<400> SEQUENCE: 27

Met Gly Lys Leu Glu Asn Ala Ser Trp Ile His Asp Pro Leu Met Lys
1               5                   10                  15

Tyr Leu Asn Ser Thr Glu Glu Tyr Leu Ala His Leu Cys Gly Pro Lys
                20                  25                  30

Arg Ser Asp Leu Ser Leu Pro Val Ser Val Ala Tyr Ala Leu Ile Phe
            35                  40                  45

Leu Val Gly Val Met Gly Asn Leu Leu Val Cys Met Val Ile Val Arg
        50                  55                  60
```

| | | | | | | | | | | | | | | |
|---|---|---|---|---|---|---|---|---|---|---|---|---|---|---|
|His|Gln|Thr|Leu|Lys|Thr|Pro|Thr|Asn|Tyr|Tyr|Leu|Phe|Ser|Leu|Ala|
|65| | | |70| | | |75| | | |80| | |

Val Ser Asp Leu Leu Val Leu Leu Gly Met Pro Leu Glu Ile Tyr
            85                  90                  95

Glu Met Trp His Asn Tyr Pro Phe Leu Phe Gly Pro Val Gly Cys Tyr
            100                 105                 110

Phe Lys Thr Ala Leu Phe Glu Thr Val Cys Phe Ala Ser Ile Leu Ser
            115                 120                 125

Val Thr Thr Val Ser Val Glu Arg Tyr Val Ala Ile Val His Pro Phe
130             135                 140

Arg Ala Lys Leu Glu Ser Thr Arg Arg Ala Leu Arg Ile Leu Ser
145             150                 155                 160

Leu Val Trp Ser Phe Ser Val Val Phe Ser Leu Pro Asn Thr Ser Ile
            165                 170                 175

His Gly Ile Lys Phe Gln His Phe Pro Asn Gly Ser Ser Val Pro Gly
            180                 185                 190

Ser Ala Thr Cys Thr Val Thr Lys Pro Met Trp Val Tyr Asn Leu Ile
            195                 200                 205

Ile Gln Ala Thr Ser Phe Leu Phe Tyr Ile Leu Pro Met Thr Leu Ile
210             215                 220

Ser Val Leu Tyr Tyr Leu Met Gly Leu Arg Leu Lys Arg Asp Glu Ser
225             230                 235                 240

Leu Glu Ala Asn Lys Val Ala Val Asn Ile His Arg Pro Ser Arg Lys
                245                 250                 255

Ser Val Thr Lys Met Leu Phe Val Leu Val Leu Val Phe Ala Ile Cys
            260                 265                 270

Trp Thr Pro Phe His Val Asp Arg Leu Phe Phe Ser Phe Val Glu Glu
            275                 280                 285

Trp Thr Glu Ser Leu Ala Ala Val Phe Asn Leu Ile His Val Val Ser
290             295                 300

Gly Val Phe Phe Tyr Leu Ser Ser Ala Val Asn Pro Ile Ile Tyr Asn
305             310                 315                 320

Leu Leu Ser Arg Arg Phe Arg Ala Ala Phe Arg Asn Val Ser Pro
            325                 330                 335

Thr Cys Lys Trp Cys His Pro Arg His Gln Pro Gln Gly Pro Pro Ala
            340                 345                 350

Gln Lys Ile Ile Phe Leu Thr Glu Cys His Leu Met Glu Leu Thr Glu
            355                 360                 365

Asp Ala Gly Pro Gln Phe Pro Gly Gln Ser Ser Ile His Asn Thr Asn
370             375                 380

Leu Thr Met Ala Pro Cys Ala Gly Glu Val Pro
385             390                 395

<210> SEQ ID NO 28
<211> LENGTH: 1185
<212> TYPE: DNA
<213> ORGANISM: Rattus norvegicus

<400> SEQUENCE: 28

| | |
|---|---|
|atgggaaaac ttgaaaatgc ttcctggatc cacgatccac tcatgaagta cttgaacagc|60|
|acagaggagt acttggccca cctgtgtgga cccaagcgca gtgacctatc ccttccggtg|120|
|tctgtggcct atgcgctgat cttcctggtg ggggtaatgg gcaatcttct ggtgtgcatg|180|
|gtgattgtcc gacatcagac tttgaagaca cccaccaact actatctctt cagcttggca|240|
|gtctcagatc tgctggtcct gctcttgggg atgcctctgg aaatctacga gatgtggcac|300|

```
aattacccttt tcctgttcgg gcctgtggga tgctacttca agacagccct cttcgagact   360
gtgtgctttg cctccattct cagtgtcacc acggttagcg tagagcgcta tgtggccatt   420 gtccacccttt tccgagccaa gctggagagc acgcggcgac gggccctcag gatcctcagc   480
ctagtctgga gcttctctgt ggtcttttct ttgcccaata ccagcatcca tggcatcaag   540
ttccagcact ttcccaacgg gtcctccgta cctggctcag ccacctgcac agtcaccaaa   600
cccatgtggg tgtataactt gatcatccaa gctaccagct tcctcttcta catcctccca   660
atgaccctca tcagcgtcct ctactacctc atggggctca ggctgaagag agatgaatcc   720
cttgaggcga acaaagtggc tgtgaatatt cacagaccct ctagaaagtc agtcaccaag   780
atgctgtttg tcttggtcct cgtgtttgcc atctgctgga cccccttcca tgtggaccgg   840
ctcttcttca gctttgtgga agagtggaca gagtccctgg ctgctgtgtt caacctcatc   900
catgtggtat caggtgtctt cttttatctg agctccgcgg tcaacccat tatctataac    960 ctcctgtctc ggcgcttccg ggcggccttt cgaaatgttg tctcccctac ctgcaaatgg  1020
tgccatcccc ggcatcagcc acagggacct ccagcccaga agatcatctt cttgacagaa  1080
tgtcacctca tggagctgac agaggatgca ggccccagt tccctggtca gtcatccatc   1140
cacaacacca accttaccat ggcccccctgt gcgggagagg tacca                 1185
```

<210> SEQ ID NO 29
<211> LENGTH: 395
<212> TYPE: PRT
<213> ORGANISM: Mus musculus

<400> SEQUENCE: 29

```
Met Gly Lys Leu Glu Asn Ala Ser Trp Ile His Asp Ser Leu Met Lys
                  5                  10                  15

Tyr Leu Asn Ser Thr Glu Glu Tyr Leu Ala Tyr Leu Cys Gly Pro Lys
              20                  25                  30

Arg Ser Asp Leu Ser Leu Pro Val Ser Val Val Tyr Ala Leu Ile Phe
          35                  40                  45

Val Val Gly Val Ile Gly Asn Leu Leu Val Cys Leu Val Ile Ala Arg
      50                  55                  60

His Gln Thr Leu Lys Thr Pro Thr Asn Tyr Tyr Leu Phe Ser Leu Ala
  65                  70                  75                  80

Val Ser Asp Leu Leu Val Leu Leu Gly Met Pro Leu Glu Val Tyr
                  85                  90                  95

Glu Leu Trp His Asn Tyr Pro Phe Leu Phe Gly Pro Val Gly Cys Tyr
             100                 105                 110

Phe Lys Thr Ala Leu Phe Glu Thr Val Cys Phe Ala Ser Ile Leu Ser
         115                 120                 125

Val Thr Thr Val Ser Ile Glu Arg Tyr Val Ala Ile His Pro Phe
     130                 135                 140

Arg Ala Lys Leu Glu Ser Thr Arg Arg Ala Leu Arg Ile Leu Ser
145                 150                 155                 160

Leu Val Trp Ser Phe Ser Val Val Phe Ser Leu Pro Asn Thr Ser Ile
                 165                 170                 175

His Gly Ile Lys Phe Gln Gln Phe Pro Asn Gly Ser Ser Val Pro Gly
             180                 185                 190

Ser Ala Thr Cys Thr Val Thr Lys Pro Met Trp Val Tyr Asn Phe Ile
         195                 200                 205

Ile Gln Ala Thr Ser Phe Leu Phe Tyr Ile Leu Pro Met Thr Leu Ile
     210                 215                 220
```

```
Ser Val Leu Tyr Tyr Leu Met Gly Leu Arg Leu Lys Arg Asp Glu Ser
225                 230                 235                 240

Leu Glu Ala Asp Lys Val Thr Val Asn Ile His Arg Pro Ser Arg Lys
            245                 250                 255

Ser Val Thr Lys Met Leu Phe Val Leu Val Leu Val Phe Ala Ile Cys
        260                 265                 270

Trp Thr Pro Phe His Val Asp Arg Leu Phe Phe Ser Phe Val Asp Glu
    275                 280                 285

Trp Thr Glu Ser Leu Ala Ala Val Phe Asn Leu Ile His Val Val Ser
    290                 295                 300

Gly Val Phe Phe Tyr Leu Ser Ser Ala Val Asn Pro Ile Ile Tyr Asn
305                 310                 315                 320

Leu Leu Ser Arg Arg Phe Arg Ala Ala Phe Arg Asn Val Val Ser Pro
                325                 330                 335

Ser Cys Lys Trp Cys His Pro Gln His Arg Pro Gln Gly Pro Pro Ala
            340                 345                 350

Gln Lys Val Ile Phe Leu Thr Glu Cys His Leu Val Glu Leu Thr Glu
        355                 360                 365

Asp Ala Gly Pro Gln Phe Pro Cys Gln Ser Ser Ile His Asn Thr Gln
    370                 375                 380

Leu Thr Thr Val Pro Cys Val Glu Glu Val Pro
385                 390                 395

<210> SEQ ID NO 30
<211> LENGTH: 1185
<212> TYPE: DNA
<213> ORGANISM: Mus musculus

<400> SEQUENCE: 30
atgggaaaac ttgaaaatgc ttcctggatc cacgattctc tcatgaagta cttgaacagc      60
acagaggagt acttggccta cctgtgtgga cccaagcgca gtgacctatc ccttccagtg     120
tctgtggtct atgcgctgat cttcgtggtg ggggtgatag gcaatcttct ggtgtgcctg     180
gtgattgccc gacatcagac tttgaagaca cccaccaact actatctctt cagcttggca     240
gtctcagact tgctggtcct gctcttaggt atgccactgg aggtctacga gttgtggcac     300
aattatccct tcctgtttgg gccggtggga tgctacttca agacagccct cttcgagact     360
gtgtgctttg cctccattct cagtgtcacc acggttagca ttgagcgcta cgtggccatt     420
gtccatccat tccgagccaa gctggagagc acacggcgac gggccctcag gatcctcagc     480
ctagtctgga gcttctctgt ggtctttttct tgcccaaca ccagcatcca tggcatcaag     540
ttccagcagt ttcccaacgg gtcctccgtg cccggctctg ccacctgcac agtcaccaaa     600
cccatgtggg tgtataactt catcatccaa gctacctcct tcctcttcta catcctcccg     660
atgaccctca tcagcgtcct ctactatctc atggggctca ggctgaagag agatgaatct     720
cttgaggcag acaaagtgac tgtgaatatt cacagaccct ccagaaaatc agtcaccaag     780
atgctgtttg tcttggtcct cgtgtttgct atctgttgga ccccttttcca tgtggacagg     840 ctcttcttca gctttgtgga cgagtggact gagtccctgg ctgctgtgtt caacctcatc     900
cacgtggtat caggtgtctt tttctatctg agctccgctg tcaacccat tatatataac     960 ctcctgtctc ggcgcttccg ggcggccttt cggaatgttg tctctccttc ctgcaaatgg    1020
tgccatcccc agcatcgccc acaggggcct ccagcccaga aggttatctt cttgacagaa    1080
tgccaccttg tggagctgac agaggatgcg ggccccagt tcccttgtca gtcatccatc    1140
```
cacaacaccc aacttaccac cgtcccctgt gttgaagagg tacca             1185

<210> SEQ ID NO 31
<211> LENGTH: 426
<212> TYPE: PRT
<213> ORGANISM: Homo sapiens

<400> SEQUENCE: 31

Met Thr Pro Leu Cys Leu Asn Cys Ser Val Leu Pro Gly Asp Leu Tyr
                 5                  10                  15

Pro Gly Gly Ala Arg Asn Pro Met Ala Cys Asn Gly Ser Ala Ala Arg
             20                  25                  30

Gly His Phe Asp Pro Glu Asp Leu Asn Leu Thr Asp Glu Ala Leu Arg
         35                  40                  45

Leu Lys Tyr Leu Gly Pro Gln Gln Thr Glu Leu Phe Met Pro Ile Cys
     50                  55                  60

Ala Thr Tyr Leu Leu Ile Phe Val Val Gly Ala Val Gly Asn Gly Leu
 65                  70                  75                  80

Thr Cys Leu Val Ile Leu Arg His Lys Ala Met Arg Thr Pro Thr Asn
                 85                  90                  95

Tyr Tyr Leu Phe Ser Leu Ala Val Ser Asp Leu Leu Val Leu Leu Val
            100                 105                 110

Gly Leu Pro Leu Glu Leu Tyr Glu Met Trp His Asn Tyr Pro Phe Leu
        115                 120                 125

Leu Gly Val Gly Gly Cys Tyr Phe Arg Thr Leu Leu Phe Glu Met Val
    130                 135                 140

Cys Leu Ala Ser Val Leu Asn Val Thr Ala Leu Ser Val Glu Arg Tyr
145                 150                 155                 160

Val Ala Val Val His Pro Leu Gln Ala Arg Ser Met Val Thr Arg Ala
                165                 170                 175

His Val Arg Arg Val Leu Gly Ala Val Trp Gly Leu Ala Met Leu Cys
            180                 185                 190

Ser Leu Pro Asn Thr Ser Leu His Gly Ile Gln Gln Leu His Val Pro
        195                 200                 205

Cys Arg Gly Pro Val Pro Asp Ser Ala Val Cys Met Leu Val Arg Pro
    210                 215                 220

Arg Ala Leu Tyr Asn Met Val Val Gln Thr Thr Ala Leu Leu Phe Phe
225                 230                 235                 240

Cys Leu Pro Met Ala Ile Met Ser Val Leu Tyr Leu Leu Ile Gly Leu
                245                 250                 255

Arg Leu Arg Arg Glu Arg Leu Leu Met Gln Glu Ala Lys Gly Arg
            260                 265                 270

Gly Ser Ala Ala Ala Arg Ser Arg Tyr Thr Cys Arg Leu Gln Gln His
        275                 280                 285

Asp Arg Gly Arg Arg Gln Val Thr Lys Met Leu Phe Val Leu Val Val
    290                 295                 300

Val Phe Gly Ile Cys Trp Ala Pro Phe His Ala Asp Arg Val Met Trp
305                 310                 315                 320

Ser Val Val Ser Gln Trp Thr Asp Gly Leu His Leu Ala Phe Gln His
                325                 330                 335

Val His Val Ile Ser Gly Ile Phe Phe Tyr Leu Gly Ser Ala Ala Asn
            340                 345                 350

Pro Val Leu Tyr Ser Leu Met Ser Ser Arg Phe Arg Glu Thr Phe Gln
        355                 360                 365

Glu Ala Leu Cys Leu Gly Ala Cys Cys His Arg Leu Arg Pro Arg His

```
                    370                 375                 380
Ser Ser His Ser Leu Ser Arg Met Thr Thr Gly Ser Thr Leu Cys Asp
385                 390                 395                 400

Val Gly Ser Leu Gly Ser Trp Val His Pro Leu Ala Gly Asn Asp Gly
                405                 410                 415

Pro Glu Ala Gln Gln Glu Thr Asp Pro Ser
                420                 425

<210> SEQ ID NO 32
<211> LENGTH: 1278
<212> TYPE: DNA
<213> ORGANISM: Homo sapiens

<400> SEQUENCE: 32
atgactcctc tctgcctcaa ttgctctgtc ctccctggag acctgtaccc agggggtgca      60
aggaacccca tggcttgcaa tggcagtgcg gccagggggc actttgaccc tgaggacttg     120
aacctgactg acgaggcact gagactcaag tacctgggc cccagcagac agagctgttc      180
atgcccatct gtgccacata cctgctgatc ttcgtggtgg cgctgtggg caatgggctg      240 acctgtctgg tcatcctgcg ccacaaggcc atgcgcacgc taccaactact ctacctcttc    300 agcctggccg tgtcggacct gctggtgctg ctggtgggcc tgcccctgga gctctatgag     360
atgtggcaca actacccctt cctgctgggc gttggtggct gctatttccg cacgctactg     420
tttgagatgg tctgcctggc ctcagtgctc aacgtcactg ccctgagcgt ggaacgctat     480
gtggccgtgg tgcacccact ccaggccagg tccatggtga cgcgggccca tgtgcgccga     540
gtgcttgggg ccgtctgggg tcttgccatg ctctgctccc tgcccaacac cagcctgcac     600
ggcatccagc agctgcacgt gccctgccgg ggcccagtgc agactcagc tgtttgcatg     660 ctggtccgcc cacgggccct ctacaacatg gtagtgcaga ccaccgcgct gctcttcttc     720
tgcctgccca tggccatcat gagcgtgctc tacctgctca ttgggctgcg actgcggcgg     780
gagaggctgc tgctcatgca ggaggccaag gcagggggct ctgcagcagc caggtccaga     840
tacacctgca ggctccagca gcacgatcgg ggccggagac aagtgaccaa gatgctgttt     900
gtcctggtcg tggtgtttgg catctgctgg gccccgttcc acgccgaccg cgtcatgtgg     960
agcgtcgtgt cacagtggac agatggcctg cacctggcct tccagcacgt gcacgtcatc    1020
tccggcatct tcttctacct gggctcggcg gccaaccccg tgctctatag cctcatgtcc    1080
agccgcttcc gagagacctt ccaggaggcc ctgtgcctcg ggccgctg ccatcgcctc      1140 agaccccgcc acagctccca cagcctcagc aggatgacca caggcagcac cctgtgtgat    1200
gtgggctccc tggcagctg ggtccacccc ctggctggga cgatggccc agaggcgcag     1260 caagagaccg atccatcc                                                  1278

<210> SEQ ID NO 33
<211> LENGTH: 412
<212> TYPE: PRT
<213> ORGANISM: Rattus norvegicus

<400> SEQUENCE: 33

Met Leu Ser Pro Asn Ala Ser Thr Gly Leu Leu Ser Cys Asn Asp Ser
                5                   10                  15

Glu Phe Lys Glu His Phe Asp Leu Glu Asp Leu Asn Leu Thr His Glu
                20                  25                  30

Asp Leu Arg Leu Lys Tyr Leu Gly Pro Gln Gln Val Lys Gln Phe Leu
                35                  40                  45
```

```
Pro Ile Cys Val Thr Tyr Leu Leu Ile Phe Val Val Gly Thr Leu Gly
        50                  55                  60
Asn Gly Leu Thr Cys Thr Val Ile Leu Arg Gln Lys Ala Met His Thr
 65                  70                  75                  80
Pro Thr Asn Phe Tyr Leu Phe Ser Leu Ala Val Ser Asp Leu Leu Val
                 85                  90                  95
Leu Leu Val Gly Leu Pro Leu Glu Leu Tyr Glu Met Gln His Asn Tyr
            100                 105                 110
Pro Phe Gln Leu Gly Ala Gly Cys Tyr Phe Arg Ile Leu Leu Leu
            115                 120                 125
Glu Thr Val Cys Leu Ala Ser Val Leu Asn Val Thr Ala Leu Ser Val
130                 135                 140
Glu Arg Tyr Val Ala Val Val His Pro Leu Gln Ala Lys Ser Val Met
145                 150                 155                 160
Thr Arg Thr His Val Arg Arg Met Leu Gly Ala Ile Trp Val Phe Ala
                165                 170                 175
Ile Leu Phe Ser Leu Pro Asn Thr Ser Leu His Gly Leu Ser Pro Leu
                180                 185                 190
Tyr Val Pro Cys Arg Gly Pro Val Pro Asp Ser Val Thr Cys Thr Leu
            195                 200                 205
Val Arg Pro Gln Phe Phe Tyr Lys Leu Val Ile Gln Thr Thr Ile Leu
            210                 215                 220
Leu Phe Phe Cys Leu Pro Met Val Thr Ile Ser Val Leu Tyr Leu Leu
225                 230                 235                 240
Ile Gly Leu Arg Leu Arg Arg Glu Arg Met Leu Leu Gln Glu Glu Val
                245                 250                 255
Lys Gly Arg Ile Ser Ala Ala Ala Arg Gln Ala Ser His Arg Ser Ile
                260                 265                 270
Gln Leu Arg Asp Arg Glu Arg Gln Val Thr Lys Met Leu Ile Ala
            275                 280                 285
Leu Val Ile Val Phe Gly Thr Cys Trp Val Pro Phe His Ala Asp Arg
            290                 295                 300
Leu Met Trp Ser Met Val Ser His Trp Thr Asp Gly Leu Arg Leu Ala
305                 310                 315                 320
Phe Gln Ser Val His Leu Ala Ser Gly Val Phe Leu Tyr Leu Gly Ser
                325                 330                 335
Ala Ala Asn Pro Glu Leu Tyr Asn Leu Met Ser Thr Arg Phe Arg Glu
            340                 345                 350
Ser Phe Arg Glu Thr Leu Gly Leu Gly Thr Arg Cys Cys His Arg His
            355                 360                 365
Gln Pro Arg His Asp Ser His Ser His Leu Arg Leu Thr Thr Val Ser
            370                 375                 380
Thr Leu Cys Asp Arg Asn Ser Arg Asp Val Pro Leu Ala Glu Asn Arg
385                 390                 395                 400
Asp Pro Gly Cys Glu Gln Glu Thr Asp Pro Pro Glu
                405                 410

<210> SEQ ID NO 34
<211> LENGTH: 1236
<212> TYPE: DNA
<213> ORGANISM: Rattus norvegicus

<400> SEQUENCE: 34
atgctctccc caaatgcttc aacgggcctc ttgtcctgca atgacagtga gttcaaggag      60
cactttgacc ttgaggacct gaaccttact catgaggacc tgaggctgaa gtacttgggg     120
```

```
ccacagcagg taaaacaatt tttgcccatc tgtgtcacgt acctgttgat cttcgtagtg      180
ggcactctgg gcaacgggtt gacctgcacc gtcatcctgc gccagaaggc aatgcacacg      240
cccaccaact tctacctctt cagtctcgcg gtgtccgatt tgctggtgct cctggtgggc      300
ttgcccctgg aactttatga gatgcagcac aattacccat ccagctgggt gcaggtggc      360 tgttacttcc ggatactgct tttggagact gtctgcctgg cttcagtgct caatgtcaca      420
gccctaagtg tggagcgtta tgtggccgtg gtgcacccac tccaagccaa gtctgtgatg      480
acacggaccc atgtgcgccg catgttggga gccatctggg tcttcgctat tctcttctct      540
ctgcccaaca ccagcttaca tggcctcagt ccactctatg taccctgccg ggggccggtg      600
cccgattcag ttacgtgtac gctggtgcgt ccccagttct tctacaagtt ggtaatacag      660
acgaccatac tgctcttctt ctgtctgccc atggtcacca tcagtgtgct gtacctgctc      720
attgggctga gctgcgcgag ggagaggatg ttgctccaag aggaggtcaa gggcaggata      780
tctgcagcag ccaggcaggc ctcccacaga agtattcagc ttcgagatag ggaacgcaga      840
caggtgacca agatgctaat tgctctggtt atagtatttg gcacctgctg ggttccattc      900
catgctgacc gtctcatgtg gagtatggtg tcccattgga ctgacggcct cgcctggcc      960 ttccagtctg tgcaccttgc ttctggtgtc ttcttgtacc tcggctcagc ggctaacccg     1020
gagctctaca acctcatgtc cactcgcttc cgagagtcct tccggaaaac cctgggcctt     1080
gggacacggt gctgtcatcg ccaccaaccg cgtcacgact cccatagcca ccttaggttg     1140
accacagtca gcaccctgtg tgacaggaac agcaggggatg tacccctggc tgagaacagg     1200
gatccagggt gtgagcaaga gacagaccct cctgaa                              1236
```

<210> SEQ ID NO 35
<211> LENGTH: 405
<212> TYPE: PRT
<213> ORGANISM: Mus musculus

<400> SEQUENCE: 35

```
Met Val Cys Asn Ile Ser Glu Phe Lys Trp Pro Tyr Gln Pro Glu Asp
                5                  10                  15

Leu Asn Leu Thr Asp Glu Ala Leu Arg Leu Lys Tyr Leu Gly Pro Gln
            20                  25                  30

Gln Met Lys Gln Phe Val Pro Ile Cys Val Thr Tyr Leu Leu Ile Phe
        35                  40                  45

Val Val Gly Thr Leu Gly Asn Gly Leu Thr Cys Thr Val Ile Leu Arg
    50                  55                  60

Asn Lys Thr Met Arg Thr Pro Thr Asn Phe Tyr Leu Phe Ser Leu Ala
65                  70                  75                  80

Val Ser Asp Met Leu Val Leu Val Gly Leu Pro Leu Glu Leu Tyr
                85                  90                  95

Glu Met Gln Gln Asn Tyr Pro Phe Gln Leu Gly Ala Ser Ala Cys Tyr
            100                 105                 110

Phe Arg Ile Leu Leu Leu Glu Thr Val Cys Leu Ala Ser Val Leu Asn
        115                 120                 125

Val Thr Ala Leu Ser Val Glu Arg Tyr Val Ala Val Arg Pro Leu
    130                 135                 140

Gln Ala Lys Ser Val Met Thr Arg Ala His Val Arg Arg Met Val Gly
145                 150                 155                 160

Ala Ile Trp Val Leu Ala Thr Leu Phe Ser Leu Pro Asn Thr Ser Leu
                165                 170                 175
```

```
His Gly Leu Ser Gln Leu Thr Val Pro Cys Arg Gly Pro Val Pro Asp
            180                 185                 190

Ser Ala Ile Cys Ser Leu Val Gly Pro Met Asp Phe Tyr Lys Leu Val
        195                 200                 205

Val Leu Thr Thr Ala Leu Leu Phe Phe Cys Leu Pro Met Val Thr Ile
    210                 215                 220

Ser Val Leu Tyr Leu Leu Ile Gly Leu Arg Leu Arg Arg Glu Arg Met
225                 230                 235                 240

Leu Leu Gln Val Glu Val Lys Gly Arg Lys Thr Ala Ala Thr Gln Glu
                245                 250                 255

Thr Ser His Arg Arg Ile Gln Leu Gln Asp Arg Gly Arg Gln Val
            260                 265                 270

Thr Lys Met Leu Phe Ala Leu Val Val Val Phe Gly Ile Cys Trp Ala
        275                 280                 285

Pro Phe His Ala Asp Arg Ile Met Trp Ser Leu Val Tyr Gly His Ser
    290                 295                 300

Thr Glu Gly Leu His Leu Ala Tyr Gln Cys Val His Ile Ala Ser Gly
305                 310                 315                 320

Ile Phe Phe Tyr Leu Gly Ser Ala Ala Asn Pro Val Leu Tyr Ser Leu
                325                 330                 335

Met Ser Thr Arg Phe Arg Glu Thr Phe Leu Gln Ala Leu Gly Leu Gly
            340                 345                 350

Thr Gln Cys Cys His Arg Arg Gln Pro Tyr His Gly Ser His Asn His
        355                 360                 365

Ile Arg Leu Thr Thr Gly Ser Thr Leu Cys Asp Val Gly His Arg Asn
    370                 375                 380

Ser Arg Asp Glu Pro Leu Ala Val Asn Glu Asp Pro Gly Cys Gln Gln
385                 390                 395                 400

Glu Thr Asp Pro Ser
                405

<210> SEQ ID NO 36
<211> LENGTH: 1215
<212> TYPE: DNA
<213> ORGANISM: Mus musculus

<400> SEQUENCE: 36
ctggtctgca atatcagtga gttcaagtgg ccctatcaac ctgaggatct gaaccttacc      60
gatgaggccc tgaggctgaa gtatttgggg ccacagcaga tgaaacagtt tgtccccatc    120
tgtgtcacgt acctgctgat cttcgtggtg ggcactctgg caacgggct gacctgcacc     180 gtcatcctgc gcaacaagac tatgcgcacg cccaccaact tctacctctt cagcctcgct    240
gtgtccgata tgctggtgct cctggtgggc ttgcctctgg agctttatga gatgcagcaa    300
aattacccgt tccagctggg tgcgagtgcc tgctacttcc gaatactgct cttagagacc    360
gtctgcctag cttcagtgct caatgtcaca gccctgagtg tggagcgtta tgtggccgtg    420
gtgcgcccac tccaagccaa gtctgtgatg acacggggcc catgtgcgcc catggtgggg    480
gccatctggg tcctcgctac tctcttctct ctgcccaaca ccagcctgca tggcctcagt    540
caactaactg tgccctgccg ggggccggtg cccgactcag ctatatgttc gctggtgggt    600
cccatggact tctacaagtt ggtggtactg actaccgcac tgctcttctt ctgtctgccc    660
atggtcacca tcagtgtgct gtatctgctc attgggctgc ggctgcggag ggagaggatg    720
ttgctccaag tggaggtcaa gggcaggaaa accgcagcaa cccaggagac ctcccacaga    780
aggattcagc tgcaagatag ggacggagac aggtgaccaga gatgctgtt tgcactggtt    840
```

```
gtggtattcg gcatctgctg ggctccattc catgctgacc gtatcatgtg gagcctggtg    900
tatggacact caacggaagg cctgcacctg gcctaccagt gtgtccacat tgcctctggc    960
atcttcttct atctcggctc agcagccaac ccggtgctct acagcctcat gtctactcgc   1020
ttccgagaga ccttcctgca agccctgggc cttggaaccc agtgctgtca tcgccgccaa   1080
ccctatcatg gctcccataa ccacatcagg ttgaccacag gcagcaccct gtgtgacgtg   1140
ggccacagga acagcaggga cgaacctctg gctgtgaatg aggatccagg gtgtcagcaa   1200
gagacagacc cctcc                                                    1215
```

```
<210> SEQ ID NO 37
<211> LENGTH: 33
<212> TYPE: PRT
<213> ORGANISM: Homo sapiens

<400> SEQUENCE: 37

Phe Leu Phe His Tyr Ser Lys Thr Gln Lys Leu Gly Asn Ser Asn Val
 1               5                  10                  15

Val Ser Ser Val Val His Pro Leu Leu Gln Leu Val Pro His Leu His
                20                  25                  30

Glu

<210> SEQ ID NO 38
<211> LENGTH: 36
<212> TYPE: PRT
<213> ORGANISM: Homo sapiens

<400> SEQUENCE: 38

Phe Leu Phe His Tyr Ser Lys Thr Gln Lys Leu Gly Asn Ser Asn Val
 1               5                  10                  15

Val Ser Ser Val Val His Pro Leu Leu Gln Leu Val Pro His Leu His
                20                  25                  30

Glu Arg Arg Met
        35

<210> SEQ ID NO 39
<211> LENGTH: 33
<212> TYPE: PRT
<213> ORGANISM: Rattus norvegicus

<400> SEQUENCE: 39

Phe Leu Phe His Tyr Ser Lys Thr Gln Lys Leu Gly Asn Ser Asn Val
 1               5                  10                  15

Val Ser Ser Val Val His Pro Leu Leu Gln Leu Val Pro Gln Leu His
                20                  25                  30

Glu

<210> SEQ ID NO 40
<211> LENGTH: 36
<212> TYPE: PRT
<213> ORGANISM: Rattus norvegicus

<400> SEQUENCE: 40

Phe Leu Phe His Tyr Ser Lys Thr Gln Lys Leu Gly Asn Ser Asn Val
 1               5                  10                  15

Val Ser Ser Val Val His Pro Leu Leu Gln Leu Val Pro Gln Leu His
                20                  25                  30

Glu Arg Arg Met
        35
```

<210> SEQ ID NO 41
<211> LENGTH: 33
<212> TYPE: PRT
<213> ORGANISM: Mus musculus

<400> SEQUENCE: 41

Phe Leu Phe His Tyr Ser Lys Thr Gln Lys Leu Gly Asn Ser Asn Val
 1               5                  10                  15
Val Ser Ser Val Val His Pro Leu Leu Gln Leu Val Pro Gln Leu His
             20                  25                  30
Glu

<210> SEQ ID NO 42
<211> LENGTH: 36
<212> TYPE: PRT
<213> ORGANISM: Mus musculus

<400> SEQUENCE: 42

Phe Leu Phe His Tyr Ser Lys Thr Gln Lys Leu Gly Asn Ser Asn Val
 1               5                  10                  15
Val Ser Ser Val Val His Pro Leu Leu Gln Leu Val Pro Gln Leu His
             20                  25                  30
Glu Arg Arg Met
         35

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
tggccagcaa ggagaaacca gac                                         23

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
cagatccagc tttctttcac c                                           21

<210> SEQ ID NO 45
<211> LENGTH: 508
<212> TYPE: DNA
<213> ORGANISM: Homo sapiens

<400> SEQUENCE: 45
tggccagcaa ggagaaacca gactctcaca atgaaacatc ttcgtcccca gttccctctc     60
atcttggcca tctactgctt ctgcatgcta cagattccct cctcaggatt tcctcaacct    120
ttagctgatc cttcagatgg cttggatatt gtgcagcttg agcagctggc atattgtctg    180
agtcagtggg cacctctttc tcgccaacct aaggataatc aagacatata caaaaggttt    240
ttgtttcact actccagaac tcaggaggca acacatccag ttaaaactgg gtttcctcca    300
gtgcatcctc taatgcacct ggctgccaag ctcgccaaca ggcggatgaa gagaattctg    360
cagcgaggct cggggactgc tgcagtggac ttcaccaaga aggatcacac tgcgacctgg    420

```
ggacgaccct ttttcctttt caggcccagg aatggaagaa acattgaaga tgaggcccag    480
attcagtggt gaaagaaagc tggatctg                                      508
```

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46

```
ctcatctgtg gtctgcaaag ag                                             22
```

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47

```
ctccaaagat gcacactgtc tt                                             22
```

<210> SEQ ID NO 48
<211> LENGTH: 540
<212> TYPE: DNA
<213> ORGANISM: Rattus norvegicus

<400> SEQUENCE: 48

```
ctcatctgtg gtctgcaaag agaagccaga gcttgaagat gaaacatccg ttccctcagt    60
tccctccaat cctggtcatc tactgcttct gtatgctaca gatcccctcc tcaggagctt   120
ctccaccttt agctggtcct cctgatggtt tggatgctgt ggacccagag cgactggcac   180
actttctgaa ccagagggaa acatgttcta accaacctaa ggaaagccgg gatgtataca   240
aaaggttttt atttcactac tcccgagctt ggaagtcgac acatccagtt aactccgagt   300
ttgctcccgt ccatccattg atgcgcctgg ccgccaagct tcccagcaga aggatgaaaa   360
gactaccgcg attgctgcac acagattcca ggatggctac tatagacttc cctaagaagg   420
atcctaccac cagcttgggg cggccatttt tccttttcag gcctaggaat ggaagataca   480
ctgacaaagt ccagtagacg gcaagaatcc tatgtcacaa gacagtgtgc atctttggag   540
```

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49

```
ctgtggtctg caaagagaat cc                                             22
```

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50

```
ctccaaggc gcacaccgtc tg                                              22
```

<210> SEQ ID NO 51

```
<211> LENGTH: 538
<212> TYPE: DNA
<213> ORGANISM: Mus musculus

<400> SEQUENCE: 51
ctgtggtctg caaagagaat ccagagcttg aagatgaaac acccgctccc ccactattct      60
ccaatcctgt tcatctactg cttctgtatg ctacagattc cctcctcagg agcttcccca     120
cctttagctg attctcccga cggcttggat attgtggatc ctgagcgact ggcatacttt     180
ctgaagcaga gggaaataca ttctaaccaa cctaaggaaa accaggatgt atacaaaagg     240
tttttatttc actactccag aactcggaaa ccaacacatc cagttagcgc tgagtttgct     300
ccggtccatc cattgatgcg cctggctgcc aagctcgcca gcagaaggat gaaaagactg     360
ccgcgattgc tgcgcctcga ttccaggatg gctactgtgg acttccctaa gaaggatcct     420
actaccagcc tggggaggcc attttttcctt ttcaggccta ggaatggaag atacaccgac     480
aacaacttcc agtagacagc aagagtccca tgtcaccaga cggtgtgcgc ctttggag       538

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
ctcatctgtg gtctgcaaag ag                                               22

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
gcatacagaa gcagtagatg ac                                               22

<210> SEQ ID NO 54
<211> LENGTH: 30
<212> TYPE: DNA
<213> ORGANISM: Artificial Sequence
<220> FEATURE:
<223> OTHER INFORMATION: Probe

<400> SEQUENCE: 54
tgaggagggg atctgtagca tacagaagca                                       30
```